United States Patent
Clary et al.

(10) Patent No.: US 12,252,688 B2
(45) Date of Patent: Mar. 18, 2025

(54) STABLE INOCULANT COMPOSITIONS COMPRISING PARAFFIN OILS/WAXES

(71) Applicant: NOVOZYMES BIOAG A/S, Bagsvaerd (DK)

(72) Inventors: Dan Clary, Wake Forest, NC (US); Ben Doughan, Roanoke, VA (US)

(73) Assignee: NOVOZYMES BIOAG A/S, Bagsvaerd (DK)

( * ) Notice: Subject to any disclaimer, the term of this patent is extended or adjusted under 35 U.S.C. 154(b) by 0 days.

(21) Appl. No.: 16/615,944

(22) PCT Filed: May 24, 2018

(86) PCT No.: PCT/US2018/034381
§ 371 (c)(1),
(2) Date: Nov. 22, 2019

(87) PCT Pub. No.: WO2018/218016
PCT Pub. Date: Nov. 29, 2018

(65) Prior Publication Data
US 2020/0093125 A1   Mar. 26, 2020

Related U.S. Application Data

(60) Provisional application No. 62/511,434, filed on May 26, 2017.

(51) Int. Cl.
*C12N 1/20* (2006.01)
*A01N 27/00* (2006.01)
(Continued)

(52) U.S. Cl.
CPC .............. *C12N 1/20* (2013.01); *A01N 27/00* (2013.01); *A01N 63/20* (2020.01); *A01N 63/23* (2020.01);
(Continued)

(58) Field of Classification Search
None
See application file for complete search history.

(56) References Cited

U.S. PATENT DOCUMENTS 5,484,464 A   1/1996   Gleddie
5,586,411 A   12/1996  Gleddie
(Continued)

FOREIGN PATENT DOCUMENTS

CN   101709277 A   *   5/2010
CN   102987055 A   *   3/2013
(Continued)

OTHER PUBLICATIONS

Oregel-Zamudio, Ernesto et al.( Effect of candelilla wax edible coatings combined with biocontrol bacteria on strawberry quality during the shelf-life, Scientia Horticulturae (Amsterdam, Netherlands, (2017), 214, 273-279). (Year: 2017).*
(Continued)

*Primary Examiner* — Alton N Pryor
(74) *Attorney, Agent, or Firm* — Adam Rucker

(57) ABSTRACT

The present disclosure provides inoculant compositions and methods for enhancing the survival and/or stability of microbial cells and/or spores in an inoculant composition. In some embodiments, inoculant compositions of the present disclosure comprise microbial cells and/or spores in a carrier comprising one or more paraffin oils and/or waxes.

20 Claims, 2 Drawing Sheets

(51) Int. Cl.
*A01N 63/20* (2020.01)
*A01N 63/23* (2020.01)
*A01N 63/25* (2020.01)
*A01N 63/27* (2020.01)
*A01N 63/28* (2020.01)
*A01N 63/34* (2020.01)
*A01N 63/36* (2020.01)
*A01N 63/38* (2020.01)

(52) U.S. Cl.
CPC ............. *A01N 63/25* (2020.01); *A01N 63/27* (2020.01); *A01N 63/28* (2020.01); *A01N 63/34* (2020.01); *A01N 63/36* (2020.01); *A01N 63/38* (2020.01)

(56) References Cited

U.S. PATENT DOCUMENTS

| | | | |
|---|---|---|---|
| 5,695,541 | A | 12/1997 | Kosanke |
| 5,780,023 | A * | 7/1998 | McLaughlin .......... C12N 11/02 435/938 |
| 5,804,208 | A | 9/1998 | Andersch |
| 5,916,029 | A | 6/1999 | Smith |
| 6,569,425 | B2 | 5/2003 | Drahos |
| 6,808,917 | B1 | 10/2004 | Johnson |
| 6,824,772 | B2 | 11/2004 | Drahos |
| 7,429,477 | B2 | 9/2008 | Johnson |
| 8,011,132 | B2 | 9/2011 | Pearce |
| 8,148,138 | B2 | 4/2012 | Johnson |
| 8,278,247 | B2 | 10/2012 | Hnatowich |
| 8,445,256 | B2 | 5/2013 | Woods |
| 8,883,679 | B2 | 11/2014 | Woods |
| 8,921,089 | B2 | 12/2014 | Kang |
| 8,999,698 | B2 | 4/2015 | Kang |
| 9,017,442 | B2 | 4/2015 | Johnson |
| 9,090,884 | B2 | 7/2015 | Harman |
| 9,101,088 | B2 | 8/2015 | Hnatowich |
| 9,234,251 | B2 | 1/2016 | Snyder |
| 9,340,464 | B2 | 5/2016 | Hnatowich |
| 2014/0342905 | A1 | 11/2014 | Bullis |
| 2020/0315183 | A1* | 10/2020 | Clary ....................... C12N 1/14 |
| 2021/0219554 | A1* | 7/2021 | Greenshields ......... A01N 25/30 |

FOREIGN PATENT DOCUMENTS

| | | | |
|---|---|---|---|
| CN | 103283948 A | * | 9/2013 |
| CN | 103404703 A | * | 11/2013 |
| CN | 103787758 A | * | 5/2014 |
| CN | 104628485 A | * | 5/2015 |
| JP | 45021632 B | * | 7/1970 |
| WO | 2013/090628 A1 | | 6/2013 |
| WO | 2017/044545 A1 | | 3/2017 |
| WO | WO-2017044473 A1 | * | 3/2017 ............. A01N 43/16 |

OTHER PUBLICATIONS

Takahashi ( Mechanism of development of tuberculin allergy and its relation to acquired immunity with regard to the constituents of tubercle bacillus, Japanese Journal of Tuberculosis (1967), 14(3-4), 67-95). (Year: 1967).*

Bashan et al, 2014, Plant and soil 378(1), 1-33.

* cited by examiner

STABLE INOCULANT COMPOSITIONS COMPRISING PARAFFIN OILS/WAXES

NAMES OF PARTIES TO A JOINT RESEARCH AGREEMENT

The inventive concepts described herein were developed as part of a joint research agreement between Monsanto Company and Novozymes BioAg A/S. The activities giving rise to the claimed invention were undertaken within the scope of the joint research agreement, said agreement having been in effect on or before the date the claimed invention was made.

CROSS-REFERENCE TO RELATED APPLICATION

This application is a 35 U.S.C. 371 national application of international application no. PCT/US2018/034381 filed May 24, 2018, which claims priority or the benefit under 35 U.S.C. 119 of U.S. provisional application No. 62/511,434 filed May 26, 2017, the contents of which are fully incorporated herein by reference.

FIELD OF THE INVENTION

The present disclosure relates to compositions and methods for enhancing the stability and survival of microbial cells and/or spores in inoculant compositions.

BACKGROUND

Inoculant compositions comprising agriculturally beneficial microorganisms are known in the art. See, e.g., U.S. Pat. Nos. 5,484,464; 5,586,411; 5,695,541; 5,804,208; 5,916,029; 6,569,425; 6,808,917; 6,824,772; 7,429,477; 8,148,138; 8,278,247; 8,445,256; 8,883,679; 8,921,089; 8,999,698; 9,017,442; 9,101,088; 9,234,251; 9,340,464.

Because the effectiveness of such inoculant compositions generally depends on the ability of the microorganisms therein to survive and propagate following application, much effort has been made to increase the stability of agriculturally beneficial microorganisms in inoculant compositions. See, e.g., U.S. Pat. Nos. 8,011,132 and 9,090,884.

Nevertheless, there remains a need for improved compositions and methods for enhancing the stability and survival of microorganisms in inoculant compositions.

SUMMARY OF THE CLAIMED INVENTION

The present disclosure provides novel and inventive uses for paraffin oils and waxes.

A first aspect of the present disclosure is use of one or more paraffin oils and/or waxes for stabilizing microbial cells/spores.

A second aspect of the present disclosure is a liquid inoculant composition comprising one or more paraffin oils and/or waxes. In some embodiments, the inoculant composition comprises one or more dispersants.

A third aspect of the present disclosure is a plant seed coated with an inoculant comprising microbial cells/spores and one or more paraffin oils and/or waxes.

A fourth aspect of the present disclosure is a kit comprising coated plant seed housed in a container.

A fifth aspect of the present disclosure is a method of applying a liquid inoculant composition comprising microbial cells/spores and one or more paraffin oils and/or waxes to a plant propagation material (e.g., seed) and/or a plant that grows from said plant propagation material.

A sixth aspect of the present disclosure is a method of applying a liquid inoculant composition comprising microbial cells/spores and one or more paraffin oils and/or waxes to a plant growth medium (e.g., soil).

DETAILED DESCRIPTION

Figure 1:
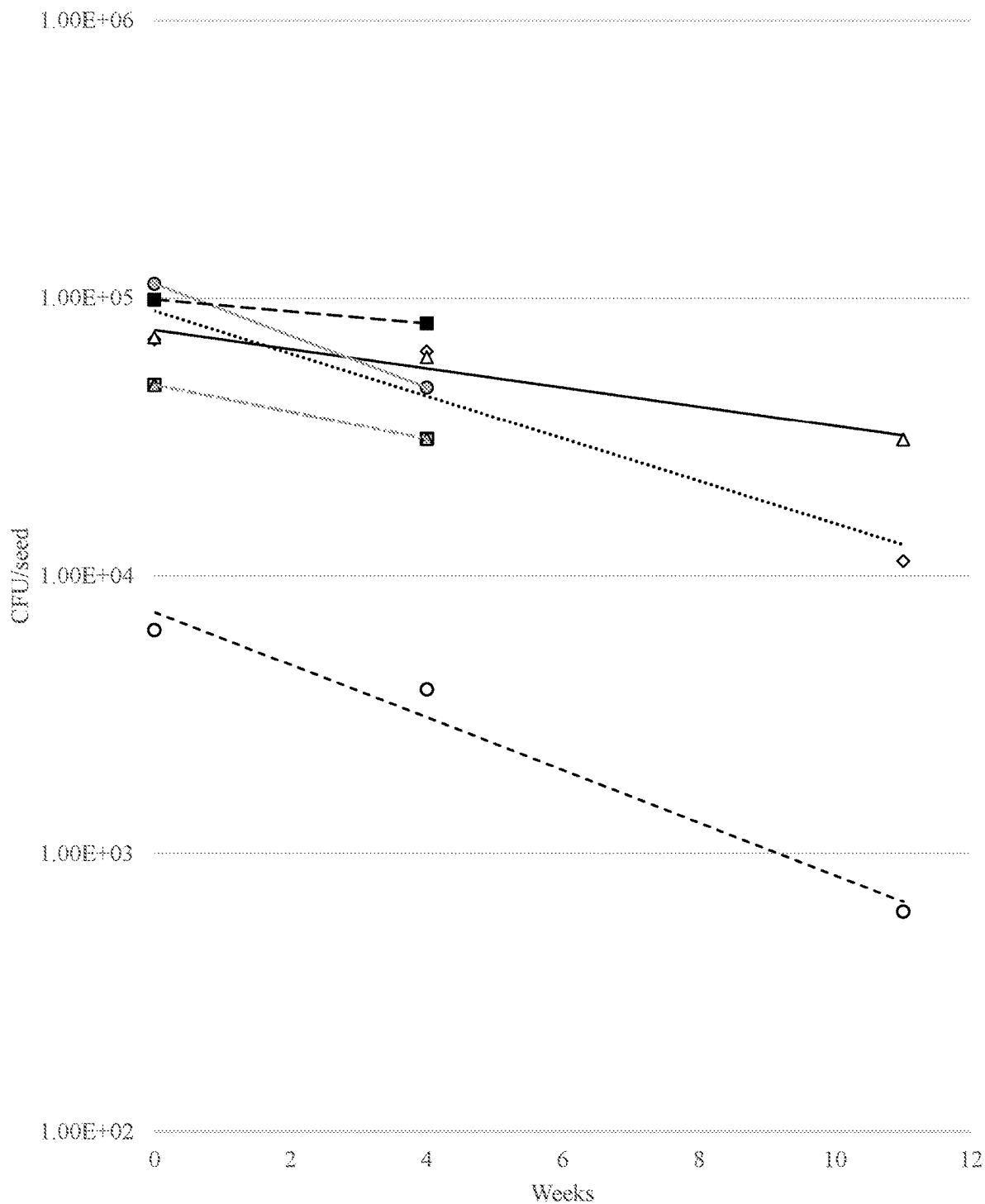
FIG. 1 is a graph showing the on-seed survivability of P. bilaiae spores at 30° C. and 65% relative humidity in SUN AG® 7N supplemented with ATLOX™ 4912 (white diamonds, dotted trend line), SUN AG® 7N supplemented with ATLOX™ 4912 and tung oil (white triangles, solid black trend line), SUN AG® 7N supplemented with SUNWAX™ DP 116 (gray circles, solid gray trend line), SUN AG® 7N supplemented with SUNWAX™ DP 116 and tung oil (gray squares, dotted gray trend line), SUN AG® 7N supplemented with SUNWAX™ DP 116 and $SiO_2$ (gray triangles, dashed gray trend line) or SUN AG® 7N supplemented with SUNWAX™ DP 116, $SiO_2$ and tung oil (black squares, dashed black trend line), as compared to a commercially available inoculant comprising P. bilaiae spores (white circles, dashed black trend line).

This description is not intended to be a detailed catalog of all the different ways in which the invention may be implemented or of all the features that may be added to the instant invention. For example, features illustrated with respect to one embodiment may be incorporated into other embodiments and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following description is intended to illustrate some particular embodiments of the invention and not to exhaustively specify all permutations, combinations and variations thereof.

The terminology used herein is for the purpose of describing particular embodiments only and is not intended to be limiting of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. For the sake of brevity and/or clarity, well-known functions or constructions may not be described in detail.

As used herein, the singular forms "a," "an," and "the" are intended to include the plural forms as well, unless the context clearly indicates otherwise.

As used herein, the terms "acaricide" and "acaricidal" refer to an agent or combination of agents the application of which is toxic to an acarid (i.e., kills an acarid, inhibits the growth of an acarid and/or inhibits the reproduction of an acarid).

As used herein, the term "agriculturally beneficial agent" refers to any agent (e.g., chemical or biological agent) or combination of agents the application of which causes or provides a beneficial and/or useful effect in agriculture including, but not limited to, agriculturally beneficial microorganisms, biostimulants, nutrients, pesticides (e.g., acaricides, fungicides, herbicides, insecticides, and nematicides) and plant signal molecules.

As used herein, the term "agriculturally beneficial microorganism" refers to a microorganism having at least one agriculturally beneficial property (e.g., the ability to fix nitrogen, the ability to solubilize phosphate and/or the ability to produce an agriculturally beneficial agent, such as a plant signal molecule).

As used herein, the term "agriculturally acceptable carrier" refers to a substance or composition that can be used to deliver an agriculturally beneficial agent to a plant, plant part or plant growth medium (e.g., soil) without causing/having an unduly adverse effect on plant growth and/or yield. As used herein, the term "foliar-compatible carrier" refers to a material that can be foliarly applied to a plant or plant part without causing/having an unduly adverse effect on the plant, plant part, plant growth, plant health, or the like. As used herein, the term "seed-compatible carrier" refers to a material that can be applied to a seed without causing/having an unduly adverse effect on the seed, the plant that grows from the seed, seed germination, or the like. As used herein, the term "soil-compatible carrier" refers to a material that can be added to a soil without causing/having an unduly adverse effect on plant growth, soil structure, soil drainage, or the like.

As used herein, the term "and/or" is intended to include any and all combinations of one or more of the associated listed items, as well as the lack of combinations when interpreted in the alternative ("or").

As used herein, the terms "associated with,"in association with" and "associated therewith," when used in reference to a relationship between a microbial strain or inoculant composition of the present disclosure and a plant or plant part, refer to at least a juxtaposition or close proximity of the microbial strain or inoculant composition and the plant or plant part. Such a juxtaposition or close proximity may be achieved by contacting or applying the microbial strain or inoculant composition directly to the plant or plant part and/or by applying the microbial strain or inoculant composition to the plant growth medium (e.g., soil) in which the plant or plant part will be grown (or is currently being grown). According to some embodiments, the microbial strain or inoculant composition is applied as a coating to the outer surface of the plant or plant part. According to some embodiments, the microbial strain or inoculant composition is applied to soil at, near or surrounding the site in which the plant or plant part will be grown (or is currently being grown).

As used herein, the term "aqueous" refers to a composition that contains more than a trace amount of water (i.e., more than 0.5% water by weight, based upon the total weight of the composition).

As used herein, the term "biostimulant" refers to an agent or combination of agents the application of which enhances one or more metabolic and/or physiological processes of a plant or plant part (e.g., carbohydrate biosynthesis, ion uptake, nucleic acid uptake, nutrient delivery, photosynthesis and/or respiration).

As used herein, the term "BRADY" is to be interpreted as a shorthand substitute for the phrase "*Bradyrhizobium elkanii* SEMIA 501, *Bradyrhizobium elkanii* SEMIA 587, *Bradyrhizobium elkanii* SEMIA 5019, *Bradyrhizobium japonicum* NRRL B-50586 (also deposited as NRRL B-59565), *Bradyrhizobium japonicum* NRRL B-50587 (also deposited as NRRL B-59566), Bradyrhizobiumjaponicum NRRL B-50588 (also deposited as NRRL B-59567), Bradyrhizobiumjaponicum NRRL B-50589 (also deposited as NRRL B-59568), *Bradyrhizobium japonicum* NRRL B-50590 (also deposited as NRRL B-59569), *Bradyrhizobium japonicum* NRRL B-50591 (also deposited as NRRL B-59570), *Bradyrhizobium japonicum* NRRL B-50592 (also deposited as NRRL B-59571), *Bradyrhizobium japonicum* NRRL B-50593 (also deposited as NRRL B-59572), *Bradyrhizobium japonicum* NRRL B-50594 (also deposited as NRRL B-50493), *Bradyrhizobium japonicum* NRRL B-50608, *Bradyrhizobium japonicum* NRRL B-50609, *Bradyrhizobium japonicum* NRRL B-50610, *Bradyrhizobium japonicum* NRRL B-50611, *Bradyrhizobium japonicum* NRRL B-50612, *Bradyrhizobium japonicum* NRRL B-50726, *Bradyrhizobium japonicum* NRRL B-50727, *Bradyrhizobium japonicum* NRRL B-50728, *Bradyrhizobium japonicum* NRRL B-50729, *Bradyrhizobium japonicum* NRRL B-50730, *Bradyrhizobium japonicum* SEMIA 566, *Bradyrhizobium japonicum* SEMIA 5079, *Bradyrhizobium japonicum* SEMIA 5080, *Bradyrhizobium japonicum* USDA 6, *Bradyrhizobium japonicum* USDA 110, *Bradyrhizobium japonicum* USDA 122, *Bradyrhizobium japonicum* USDA 123, *Bradyrhizobium japonicum* USDA 127, *Bradyrhizobium japonicum* USDA 129 and/or *Bradyrhizobium japonicum* USDA 532C."

As used herein, the terms "colony forming unit" and "cfu" refer to a microbial cell/spore capable of propagating on or in a suitable growth medium or substrate (e.g., a soil) when conditions (e.g., temperature, moisture, nutrient availability, pH, etc.) are favorable for germination and/or microbial growth.

As used herein, the term "consists essentially of,", when used in reference to inoculant compositions and methods of the present disclosure, means that the compositions/methods may contain additional components/steps so long as the additional components/steps do not materially alter the composition/method. The term "materially alter," as applied to a composition/method of the present disclosure, refers to an increase or decrease in the effectiveness of the composition/method of at least 20%. For example, a component added to an inoculant composition of the present disclosure may be deemed to "materially alter" the composition if it increases the stability and/or survivability of the microbial cells/spores in the inoculant composition by at least 20% and/or if it increases or decreases the composition's ability to enhance corn yield by at least 20%.

As used herein, the term "diazotroph" refers to an organism capable of converting atmospheric nitrogen ($N_2$) into a form that may be utilized by a plant or plant part (e.g., ammonia ($NH_3$), ammonium ($NH_4+$), etc.).

As used herein, the term "dispersant" refers to an agent or combination of agents the application of which reduces the cohesiveness of like particles, the surface tension of a liquid, the interfacial tension between two liquids and/or the interfacial tension between or a liquid and a solid.

As used herein, the terms "effective amount," "effective concentration" and "effective amount/concentration" refer to an amount or concentration that is sufficient to cause a desired effect (e.g., enhanced corn yield). The absolute value of the amount/concentration that is sufficient to cause the desired effect may be affected by factors such as the type and magnitude of effect desired, the type, size and volume of material to which the inoculant compositon will be applied, the type(s) of microorganisms in the composition, the number of microorganisms in the composition, the stability of the microorganism(s) in the inoculant composition and the storage conditions (e.g., temperature, relative humidity, duration). Those skilled in the art will understand how to select an effective amount/concentration using routine dose-response experiments after studying the present disclosure.

As used herein, the term "enhanced dispersion" refers to an improvement in one or more characteristics of microbial dispersion as compared to one or more controls (e.g., a control composition that is identical to an inoculant composition of the present disclosure except that it lacks one or more of the components found in the inoculant composition of the present disclosure). Exemplary microbial dispersion characteristics include, but are not limited to, the percentage of microbes that exist as single cells/spores when the inoculant composition is diluted in water. An inoculant composition that improves one or more microbial dispersion characteristics of the microorganism(s) contained therein as compared to a control composition (e.g., a control composition that is identical to the inoculant composition except that it lacks one or more of the components found in the inoculant composition) provides enhanced dispersion and can be referred to as a "readily dispersable inoculant composition."

As used herein, the terms "enhanced growth" and "enhanced plant growth" refer to an improvement in one or more characteristics of plant growth and/or development as compared to one or more control plants (e.g., a plant germinated from an untreated seed or an untreated plant). Exemplary plant growth/development characteristics include, but are not limited to, biomass, carbohydrate biosynthesis, chlorophyll content, cold tolerance, drought tolerance, height, leaf length, leaf mass, leaf number, leaf surface area, leaf volume, nutrient uptake (e.g., calcium, magnesium, nitrogen, phosphorous and/or potassium uptake), rate(s) of photosynthesis, root area, root diameter, root length, root mass, root nodulation (e.g., nodule mass, nodule number, nodule volume), root number, root surface area, root volume, salt tolerance, seed germination, seedling emergence, shoot diameter, shoot length, shoot mass, shoot number, shoot surface area, shoot volume, spread, stomatal conductance and survival rate. Unless otherwise indicated, references to enhanced plant growth are to be interpreted as meaning that microbial strains, inoculant compositions and methods of the present disclosure enhance plant corn growth by enhancing nutrient availability, improving soil characteristics, etc. and are not to be interpreted as suggesting that microbial strains, inoculant compositions and methods of the present disclosure act as plant growth regulators.

As used herein, the terms "enhanced stability" and "enhanced microbial stability" refer to an improvement in one or more characteristics of microbial stability as compared to one or more controls (e.g., a control composition that is identical to an inoculant composition of the present disclosure except that it lacks one or more of the components found in the inoculant composition of the present disclosure). Exemplary microbial stability characteristics include, but are not limited to, the ability to germinate and/or propagate after being coated on a seed and/or stored for a defined period of time and the ability to cause a desired effect (e.g., enhanced plant yield and/or increased pesticidal activity) after being coated on a seed and/or stored for a defined period of time. A microorganism that exhibits improvement in one or more microbial stability characteristics as compared to a control microorganism when each is subjected to the same conditions (e.g., seed coating and storage conditions) displays enhanced stability and can be referred to as a "stable microorganism." An inoculant composition that improves one or more microbial stability characteristics of the microorganism(s) contained therein as compared to a control composition (e.g., a control composition that is identical to the inoculant composition except that it lacks one or more of the components found in the inoculant composition) provides enhanced stability and can be referred to as a "stable inoculant composition."

As used herein, the terms "enhanced survival" and "enhanced microbial survival" refer to an improvement in the survival rate of one or more microorganisms in an inoculant composition as compared to one or more microorganisms in a control composition (e.g., a control composition that is identical to an inoculant composition of the present disclosure except that it lacks one or more of the components found in the inoculant composition of the present disclosure). An inoculant composition that improves the survival rate of one or more of the microorganisms contained therein as compared to a control composition (e.g., a control composition that is identical to the inoculant composition except that it lacks one or more of the components found in the inoculant composition) provides enhanced survival and can be referred to as a stable inoculant composition.

As used herein, the terms "enhanced yield" and "enhanced plant yield" refer to an improvement in one or more characteristics of plant yield as compared to one or more control plants (e.g., a control plant germinated from an untreated seed). Exemplary plant yield characteristics include, but are not limited to, biomass; bushels per acre; grain weight per plot (GWTPP); nutritional content; percentage of plants in a given area (e.g., plot) that fail to produce grain; yield at standard moisture percentage (YSMP), such as grain yield at standard moisture percentage (GYSMP); yield per plot (YPP), such as grain weight per plot (GWTPP); and yield reduction (YRED). Unless otherwise indicated, references to enhanced plant yield are to be interpreted as meaning that microbial strains, inoculant compositions and methods of the present disclosure enhance plant yield by enhancing nutrient availability, improving soil characteristics, etc. and are not to be interpreted as suggesting that microbial strains, inoculant compositions and methods of the present disclosure act as plant growth regulators.

As used herein, the term "foliage" refers to those portions of a plant that normally grow above the ground, including, but not limited to, leaves, stalks, stems, flowers, fruiting bodies and fruits.

As used herein, the terms "foliar application" and "foliarly applied" refer to the application of one or more active ingredients to the foliage of a plant (e.g., to the leaves of the plant). Application may be effected by any suitable means, including, but not limited to, spraying the plant with a composition comprising the active ingredient(s). In some embodiments, the active ingredient(s) is/are applied to the leaves, stems and/or stalk of the plant and not to the flowers, fruiting bodies or fruits of the plant.

As used herein, the terms "fungicide" and "fungicidal" refer to an agent or combination of agents the application of which is toxic to a fungus (i.e., kills a fungus, inhibits the growth of a fungus and/or inhibits the reproduction of a fungus).

As used herein, the term "fulvic acid" encompasses pure fulvic acids and fulvic acid salts (fulvates). Non-limiting examples of fulvic acids include ammonium fulvate, boron fulvate, potassium fulvate, sodium fulvate, etc. In some embodiments, the fulvic acid comprises, consists essentially of or consists MDL Number MFCD09838488 (CAS Number 479-66-3).

As used herein, the terms "herbicide" and "herbicidal" refer to an agent or combination of agents the application of which is toxic to a weed (i.e., kills a weed, inhibits the growth of a weed and/or inhibits the reproduction of a weed).

As used herein, the term "humic acid" encompasses pure humic acids and humic acid salts (humates). Non-limiting examples of humic acids include ammonium humate, boron humate, potassium humate, sodium humate, etc. In some embodiments, the humic acid comprises, consists essentially of or consists of one or more of MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7 and CAS Number 308067-45-0.

As used herein, the terms "inoculant composition" and "inoculum" refer to a composition comprising microbial cells and/or spores, said cells/spores being capable of propagating/germinating on or in a suitable growth medium or substrate (e.g., a soil) when conditions (e.g., temperature, moisture, nutrient availability, pH, etc.) are favorable for germination and/or microbial growth.

As used herein, the terms "insecticide" and "insecticidal" refer to an agent or combination of agents the application of which is toxic to an insect (i.e., kills an insect, inhibits the growth of an insect and/or inhibits the reproduction of an insect).

As used herein, the term "isomer" includes all stereoisomers of the compounds and/or molecules to which it refers, including enantiomers and diastereomers, as well as all conformers, roatmers and tautomers, unless otherwise indicated.

Compounds and/or molecules disclosed herein include all enantiomers in either substantially pure levorotatory or dextrorotatory form, or in a racemic mixture, or in any ratio of enantiomers. Where embodiments disclose a (D)-enantiomer, that embodiment also includes the (L)-enantiomer; where embodiments disclose a (L)-enantiomer, that embodiment also includes the (D)-enantiomer. Where embodiments disclose a (+)-enantiomer, that embodiment also includes the (−)-enantiomer; where embodiments disclose a (−)-enantiomer, that embodiment also includes the (+)-enantiomer. Where embodiments disclose a (S)-enantiomer, that embodiment also includes the (R)-enantiomer; where embodiments disclose a (R)-enantiomer, that embodiment also includes the (S)-enantiomer. Embodiments are intended to include any diastereomers of the compounds and/or molecules referred to herein in diastereomerically pure form and in the form of mixtures in all ratios. Unless stereochemistry is explicitly indicated in a chemical structure or chemical name, the chemical structure or chemical name is intended to embrace all possible stereoisomers, conformers, rotamers and tautomers of compounds and/or molecules depicted.

As used herein, the term "modified microbial strain" refers to a microbial strain that is modified from a strain isolated from nature. Modified microbial strains may be produced by any suitable method(s), including, but not limited to, chemical or other form of induced mutation to a polynucleotide within any genome within the strain; the insertion or deletion of one or more nucleotides within any genome within the strain, or combinations thereof; an inversion of at least one segment of DNA within any genome within the strain; a rearrangement of any genome within the strain; generalized or specific transduction of homozygous or heterozygous polynucleotide segments into any genome within the strain; introduction of one or more phage into any genome of the strain; transformation of any strain resulting in the introduction into the strain of stably replicating autonomous extrachromosomal DNA; any change to any genome or to the total DNA composition within the strain isolated from nature as a result of conjugation with any different microbial strain; and any combination of the foregoing. The term modified microbial strains includes a strain with (a) one of more heterologous nucleotide sequences, (b) one or more non-naturally occurring copies of a nucleotide sequence isolated from nature (i.e., additional copies of a gene that naturally occurs in the microbial strain from which the modified microbial strain was derived), (c) a lack of one or more nucleotide sequences that would otherwise be present in the natural reference strain by for example deleting nucleotide sequence, and (d) added extrachromosomal DNA. In some embodiments, modified microbial strains comprise a combination of two or more nucleotide sequences (e.g., two or more naturally occurring genes that do not naturally occur in the same microbial strain) or comprise a nucleotide sequence isolated from nature at a locus that is different from the natural locus.

As used herein, the terms "nematicide" and "nematicidal" refer to an agent or combination of agents the application of which is toxic to a nematode (i.e., kills a nematode, inhibits the growth of a nematode and/or inhibits the reproduction of a nematode).

As used herein, the term "nitrogen fixing organism" refers to an organism capable of converting atmospheric nitrogen ($N_2$) into a form that may be utilized by a plant or plant part (e.g., ammonia ($NH_3$), ammonium ($NH_4^+$), etc.).

As used herein, the term "non-aqueous" refers to a composition that comprises no more than a trace amount of water (i.e., no more than 0.5% water by weight, based upon the total weight of the composition).

As used herein, the term "nutrient" refers to a compound or element useful for nourishing a plant (e.g., vitamins, macrominerals, micronutrients, trace minerals, organic acids, etc. that are necessary for plant growth and/or development).

As used herein, the term "PENI" is to be interpreted as a shorthand substitute for the phrase "*P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* NRRL 67154, *P. bilaiae* NRRL 67155, *P. bilaiae* NRRL 67156, *P. bilaiae* NRRL 67157, *P. bilaiae* NRRL 67158, *P. bilaiae* NRRL 67159, *P. bilaiae* RS7B-SD1, *Penicillium* brevicompactum AgRF18, *Penicillium canescens* ATCC 10419, *Penicillium expansum* ATCC 24692, *Penicillium expansum* YT02, *Penicillium* fellatanum ATCC 48694, *Penicillium* gaestrivorus NRRL 50170, *Penicillium glabrum* DAOM 239074, *Penicillium glabrum* CBS 229.28, *Penicillium janthinellum* ATCC 10455, *Penicillium lanosocoeruleum* ATCC 48919, *Penicillium radicum* ATCC 201836, *Penicillium radicum* FRR 4717, *Penicillium radicum* FRR 4719, *Penicillium radicum* $N_{93/47267}$, and/or *Penicillium raistrickii* ATCC 10490."

As used herein, the term "*Penicillium* bilaiae" and "*P. bilaiae*" are intended to include all iterations of the species name, such as "*Penicillium* bilaji" and "*Penicillium* bilaii."

As used herein, the terms "percent identity," "% identity" and "percent identical" refer to the relatedness of two or more nucleotide or amino acid sequences, which may be calculated by (i) comparing two optimally aligned sequences over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present invention, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, the term "pest" includes any organism or virus that negatively affects a plant, including, but not limited to, organisms and viruses that spread disease, damage host plants and/or compete for soil nutrients. The term "pest" encompasses organisms and viruses that are known to associate with plants and to cause a detrimental effect on the plant's health and/or vigor. Plant pests include, but are not limited to, arachnids (e.g., mites, ticks, spiders, etc.), bacteria, fungi, gastropods (e.g., slugs, snails, etc.), invasive plants (e.g., weeds), insects (e.g., white flies, *thrips*, weevils, etc.), nematodes (e.g., root-knot nematode, soybean cyst nematode, etc.), rodents and viruses (e.g., tobacco mosaic virus (TMV), tomato spotted wilt virus (TSWV), cauliflower mosaic virus (CaMV), etc.).

As used herein, the terms "pesticide" and "pesticidal" refer to agents or combinations of agents the application of which is toxic to a pest (i.e., kills a pest, inhibits the growth of a pest and/or inhibits the reproduction of a pest). Non-limiting examples of pesticides include acaricides, fungicides, herbicides, insecticides, and nematicides, etc.

As used herein, the term "phosphate-solubilizing microorganism" refers to a microorganism capable of converting insoluble phosphate into a soluble form of phosphate.

As used herein, the term "plant" includes all plant populations, including, but not limited to, agricultural, horticultural and silvicultural plants. The term "plant" encompasses plants obtained by conventional plant breeding and optimization methods (e.g., marker-assisted selection) and plants obtained by genetic engineering, including cultivars protectable and not protectable by plant breeders' rights.

As used herein, the term "plant cell" refers to a cell of an intact plant, a cell taken from a plant, or a cell derived from a cell taken from a plant. Thus, the term "plant cell" includes cells within seeds, suspension cultures, embryos, meristematic regions, callus tissue, leaves, shoots, gametophytes, sporophytes, pollen and microspores.

As used herein, the term "plant growth regulator" refers to an agent or combination of agents the application of which accelerates or retards the growth/maturation rate of a plant through direct physiological action on the plant or which otherwise alters the behavior of a plant through direct physiological action on the plant. "Plant growth regulator" shall not be interpreted to include any agent or combination of agents excluded from the definition of "plant regulator" that is set forth section 2(v) of the Federal Insecticide, Fungicide, and Rodenticide Act (7 U.S.C. § 136(v)). Thus, "plant growth regulator" does not encompass microorganisms applied to a plant, plant part or plant growth medium for the purpose of enhancing the availability and/or uptake of nutrients, nutrients necessary to normal plant growth, soil amendments applied for the purpose of improving soil characteristics favorable for plant growth or vitamin hormone products as defined by 40 C.F.R. § 152.6(f).

As used herein, the term "plant part" refers to any part of a plant, including cells and tissues derived from plants. Thus, the term "plant part" may refer to any of plant components or organs (e.g., leaves, stems, roots, etc.), plant tissues, plant cells and seeds. Examples of plant parts, include, but are not limited to, anthers, embryos, flowers, fruits, fruiting bodies, leaves, ovules, pollen, rhizomes, roots, seeds, shoots, stems and tubers, as well as scions, rootstocks, protoplasts, calli and the like.

As used herein, the term "plant propagation material" refers to a plant part from which a whole plant can be generated.

Examples of plant propagation materials include, but are not limited to, cuttings (e.g., leaves, stems), rhizomes, seeds, tubers and cells/tissues that can be cultured into a whole plant.

As used herein, the terms "spore" and "microbial spore" refer to a microorganism in its dormant, protected state.

As used herein, the term "stabilizing compound" refers to an agent or combination of agents the application of which enhances the survival and/or stability of a microorganism in an inoculant composition.

As used herein with respect to inoculant compositions, the term "stable" refers to an inoculant composition in which microorganisms exhibit enhanced stability and/or enhanced survival. In general, an inoculant composition may be labeled "stable" if it improves the survival rate and/or at least one microbial stability characteristic of at least one microorganism contained therein.

As used herein with respect to microbial strains, the term "survival rate" refers to the percentage of microbial cell/spore that are viable (i.e., capable of propagating on or in a suitable growth medium or substrate (e.g., a soil) when conditions (e.g., temperature, moisture, nutrient availability, pH, etc.) are favorable for germination and/or microbial growth) at a given period of time.

While certain aspects of the present disclosure will hereinafter be described with reference to embodiments thereof, it will be understood by those of ordinary skill in the art that various changes in form and details may be made therein without departing from the spirit and scope of the present disclosure as defined by the claims.

All publications, patent applications, patents and other references mentioned herein are incorporated by reference in their entirety, except insofar as they contradict any disclosure expressly set forth herein.

The present disclosure provides inoculant compositions comprising, consisting essentially of, or consisting of one or more microbial cells/spores and a carrier comprising, consisting essentially of or consisting of one or more paraffin oils and/or waxes.

Inoculant compositions of the present disclosure may comprise any suitable microorganism(s), including, but not limited to, agriculturally beneficial microorganisms such as diazotrophs, phosphate-solubilizing microorganisms and biopesticides. Selection of suitable microorganisms will depend upon the intended application(s). In some embodiments, inoculant compositions of the present disclosure comprise one or more microorganisms selected from the genera and species listed in Appendix A.

In some embodiments, inoculant compositions of the present disclosure comprise one or more Gram-negative bacteria and/or Gram-positive bacteria. Non-limiting examples of bacteria that may be included in compositions of the present disclosure include Azospirillum brasilense INTA Az-39, *Bacillus amyloliquefaciens* D747, *Bacillus amyloliquefaciens* NRRL B 50349, *Bacillus amyloliquefaciens* TJ1000, *Bacillus amyloliquefaciens* FZB24, *Bacillus amyloliquefaciens* FZB42, *Bacillus amyloliquefaciens* IN937a, *Bacillus amyloliquefaciens* IT-45, *Bacillus amyloliquefaciens* TJ1000, *Bacillus amyloliquefaciens* MBI600, *Bacillus amyloliquefaciens* BS27 (deposited as NRRL B-5015), *Bacillus amyloliquefaciens* BS2084 (deposited as NRRL B-50013), *Bacillus amyloliquefaciens* 15AP4 (deposited as ATCC PTA-6507), *Bacillus amyloliquefaciens* 3AP4 (deposited as ATCC PTA-6506), *Bacillus amyloliquefaciens* LSSA01 (deposited as NRRL B-50104), *Bacillus amyloliquefaciens* ABP278 (deposited as NRRL B-50634), *Bacillus amyloliquefaciens* 1013 (deposited as NRRL B-50509), *Bacillus amyloliquefaciens* 918 (deposited as NRRL B-50508), *Bacillus amyloliquefaciens* 22CP1 (deposited as ATCC PTA-6508) and *Bacillus amyloliquefaciens* BS18 (deposited as NRRL B-50633), *Bacillus cereus* 1-1562, *Bacillus firmus* I-1582, *Bacillus lichenformis* BA842 (deposited as NRRL B-50516), *Bacillus lichenformis* BL21 (deposited as NRRL B-50134), *Bacillus mycoides* NRRL B-21664, *Bacillus pumilus* NRRL B 21662, *Bacillus pumilus* NRRL B-30087, *Bacillus pumilus* ATCC 55608, *Bacillus pumilus* ATCC 55609, *Bacillus pumilus* GB34, Bacilluspumilus KFP9F, *Bacillus pumilus* QST 2808, *Bacillus subtilis* ATCC 55078, *Bacillus subtilis* ATCC 55079, *Bacillus subtilis* MBI 600, *Bacillus subtilis* NRRL B-21661, *Bacillus subtilis* NRRL B-21665, *Bacillus subtilis* CX-9060, *Bacillus subtilis* GB03, *Bacillus subtilis* GB07, *Bacillus subtilis* QST-713, *Bacillus subtilis* FZB24, *Bacillus subtilis* D747, *Bacillus subtilis* 3BP5 (deposited as NRRL B-50510), *Bacillus thuringiensis* ATCC 13367, *Bacillus thuringiensis* GC-91, *Bacillus thuringiensis* NRRL B-21619, *Bacillus thuringiensis* ABTS-1857, *Bacillus thuringiensis* SAN 401 I, *Bacillus thuringiensis* ABG-6305, *Bacillus thuringiensis* ABG-6346, *Bacillus thuringiensis* AM65-52, *Bacillus thuringiensis* SA-12, *Bacillus thuringiensis* SB4, *Bacillus thuringiensis* ABTS-351, *Bacillus thuringiensis* HD-1, *Bacillus thuringiensis* EG 2348, *Bacillus thuringiensis* EG 7826, *Bacillus thuringiensis* EG 7841, *Bacillus thuringiensis* DSM 2803, *Bacillus thuringiensis* NB-125, *Bacillus thuringiensis* NB-176, BRADY, Pseudonionas *jessenii* PS06, *Rhizobium leguminosarum* SO12A-2 (IDAC 080305-01), Sinorhizobiumfredii CCBAU1 14, *Sinorhizobium fredii* USDA 205, *Yersinia* entomophaga 082KB8 and combinations thereof, as well as microorganisms having at least at least 75, 80, 85, 90, 95, 96, 97, 97.5. 98, 98.5, 99, 99.5, 99.6, 99.7, 99.8, 99.9% or more identical to any of the aforementioned strains on the basis of 16S rDNA sequence identity.

In some embodiments, inoculant compositions of the present disclosure comprise one or more fungi. Non-limiting examples of fungi that may be included in compositions of the present disclosure include *Gliocladium virens* ATCC 52045, *Gliocladium virens* GL-21, *Glomus intraradices* RTI-801, *Metarhizium anisopliae* F52, PENI, *Trichoderma asperellum* SKT-1, *Trichoderma asperellum* ICC 012, *Trichoderma atroviride* LC52, *Trichoderma atroviride* CNCM 1-1237, *Trichoderma* fertile JM41R, *Trichoderma gamsii* ICC 080, *Trichoderma hamatum* ATCC 52198, *Trichoderma harzianum* ATCC 52445, *Trichoderma harzianum* KRL-AG2, *Trichoderma harzianum* T-22, *Trichoderma harzianum* TH-35, *Trichoderma harzianum* T-39, *Trichoderma harzianum* ICC012, *Trichoderma reesi* ATCC 28217, *Trichoderma virens* ATCC 58678, *Trichoderma virens* G1-3, *Trichoderma virens* GL-21, *Trichoderma virens* G-41, *Trichoderma* viridae ATCC 52440, *Trichoderma* viridae ICC080, *Trichoderma* viridae TV1 and combinations thereof, as well as microorganisms having at least at least 75, 80, 85, 90, 95, 96, 97, 97.5. 98, 98.5, 99, 99.5, 99.6, 99.7, 99.8, 99.9% or more identical to any of the aforementioned strains on the basis of internal transcribed spacer (ITS) and/or cytochrome c oxidase (CO1) sequence identity.

In some embodiments, inoculant compositions of the present disclosure comprise one or more mycorrhizal fungi (e.g., one or more endomycorrhizal fungi and/or one or more ectomycorrhizal fungi). Non-limiting examples of mycorrhizal fungi that may be included in compositions of the present disclosure include mycorrhizal strains such as Gigaspora margarita, *Glomus aggregatum, Glomus brasilianum, Glomus clarum, Glomus deserticola, Glomus etunicatum, Glomus intraradices, Glomus monosporum, Glomus mosseae*, Laccaria bicolor, Laccaria laccata, Paraglomus brazilianum, Pisolithus tinctorius, *Rhizopogon* amylopogon, *Rhizopogon* fulvigleba, *Rhizopogon luteolus, Rhizopogon villosuli, Scleroderma cepa* and *Scleroderma citrinum* and combinations thereof.

In some embodiments, inoculant compositions of the present disclosure comprise one or more diazotrophs and/or phosphate-solubilizing microorganisms.

In some embodiments, inoculant compositions of the present disclosure comprise one or more biofungicides, bioherbicides, bioinsectides and/or bionematicides. See generally BURGES, FORMULATION OF MICROBIAL BIOPESTICIDES: BENEFICIAL MICROORGANISMS, NEMATODES AND SEED TREATMENTS (Springer Science & Business Media) (2012); HALL & MENN, BIOPESTICIDES: USE AND DELIVERY (Humana Press) (1998); McCoy, et al., Entomogenous fungi, in CRC HANDBOOK OF NATURAL PESTICIDES. MICROBIAL PESTICIDES, PART A. ENTOMOGENOUS PROTOZOA AND FUNGI (C. M.

Inoffo, ed.), Vol. 5:151-236 (1988); SAMSON, et al., ATLAS OF ENTOMOPATHOGENIC FUNGI (Springer-Verlag, Berlin) (1988); and deFaria and Wraight, Mvcoinsecticides and Mvcoacaricides: A comprehensive list with worldwide coverage and international classification offormulation types, BIOL. CONTROL (2007), doi: 10.1016/j.biocontrol.2007.08.001.

In some embodiments, inoculant compositions of the present disclosure comprise one or more modified microbial strains.

Compositions of the present invention may comprise vegetative cells and/or dormant spores. According to some embodiments, at least 1, 5, 10, 15, 20, 25, 30, 35, 40, 45, 50, 55, 60, 65, 70, 75, 80, 85, 90, 95, 96, 97, 98, 99% or more of the microbes in a composition of the present disclosure are present as vegetative cells. According to some embodiments, at least 1, 5, 10, 15, 20, 25, 30, 35, 40, 45, 50, 55, 60, 65, 70, 75, 80, 85, 90, 95, 96, 97, 98, 99% or more of the microbes in a composition of the present disclosure are present as spores. In some embodiments, inoculant compositions of the present disclosure are devoid of vegetative cells. In some embodiments, inoculant compositions of the present disclosure are devoid of spores.

Microbial spores may be produced by any suitable method(s), including, but not limited to, liquid fermentation and solid state fermentation. See, e.g., Cunningham et al., CAN. J. BOT. 68:2270 (1990); Friesen et al., APPL. MICROBIOL. BIOTECH. 68:397 (2005).

Spores may be harvested and/or concentrated using any suitable method(s), including, but not limited to, centrifugation (e.g., density gradient centrifugation, disc stack centrifugation, tubular bowl centrifugation), coagulation, decanting, felt bed collection, filtration (e.g., drum filtration, sieving, ultrafiltration), flocculation, impaction and trapping (e.g., cyclone spore trapping, liquid impingement).

Microorganisms may be incorporated into inoculant compositions of the present disclosure in any suitable amount(s)/concentration(s). The absolute value of the amount/concentration of microbial cells/spores sufficient to cause a desired effect may be affected by factors such as the type of effect desired; the magnitude of the effect desired; the type, size and volume of material to which the composition will be applied; the type of microbial cells/spores; the inherent stability of the microbial cells/spores; and storage conditions (e.g., temperature, relative humidity, duration). Those skilled in the art will understand how to select an effective amount/concentration using routine dose-response experiments after reading the present disclosure. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; and 62/347,805.

In some embodiments, microbial cells/spores comprise about 0.1 to about 50% (by weight) of the inoculant composition. For example, inoculant compositions of the present disclosure may comprise about 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50% or more (by weight) of one or more microorganisms. In some embodiments, the microbial cell/spore amount/concentration is about 1, 2, 3, 4 or 5 to about 5, 6, 7, 8, 9, 10, 11, 12, 13, 14, 15, 16, 17, 18, 19, 20, 21, 22, 23, 24 or 25% (by weight) of the inoculant composition.

In some embodiments, microbial cells/spores are present in an amount ranging from about $1 \times 10^{10}$ to about $1 \times 10^{20}$ colony-forming units (cfu) per gram and/or milliliter of inoculant composition. For example, inoculant compositions of the present disclosure may comprise about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$ or more microbial cells/spores per gram and/or milliliter of inoculant composition.

In some embodiments, the amount/concentration of microbial cells/spores is that amount/concentration which is effective to enhance the germination and/or emergence of plant seeds to which the inoculant composition is applied.

In some embodiments, the amount/concentration of microbial cells/spores is that amount/concentration which is effective to enhance the germination and/or emergence of plant seeds introduced into a plant growth medium (e.g., soil) treated with the inoculant composition.

In some embodiments, the amount/concentration of microbial cells/spores is that amount/concentration which is effective to enhance the growth and/or yield of the plants and plant parts to which the inoculant composition is applied.

In some embodiments, the amount/concentration of microbial cells/spores is that amount/concentration which is effective to enhance the growth and/or yield of plants and plant parts grown in a plant growth medium (e.g., soil) treated with the inoculant composition.

In some embodiments, the amount/concentration of microbial cells/spores is that amount/concentration which is effective for fixing atmospheric nitrogen, solubilizing phosphate, and/or controlling one or more phytopathogenic pests when the inoculant composition is applied to a plant or plant part.

In some embodiments, the amount/concentration of microbial cells/spores is that amount/concentration which is effective for fixing atmospheric nitrogen, solubilizing phosphate, and/or controlling one or more phytopathogenic pests when the inoculant composition is introduced into a plant growth medium (e.g., a soil).

It is to be understood that microbial cells/spores may be incorporated into inoculant compositions of the present disclosure in any suitable form, including, but not limited to, powders and granuales comprising vegetative cells and/or spores (e.g., liquid cultures that have been drum dried, evaporation dried, fluidized bed dried, freeze dried, spray dried, spray-freeze dried, tray dried and/or vacuum dried to produce powders/granuales).

Inoculant compositions of the present disclosure may comprise any suitable carrier(s), including, but not limited to, foliar-compatible carriers, seed-compatible carriers and soil-compatible carriers. Selection of appropriate carrier components will depend on the intended application(s) and the microorganism(s) present in the inoculant composition.

In some embodiments, the carrier consists essentially of or consists of one or more paraffin oils and/or waxes.

Inoculant compositions of the present disclosure may comprise any suitable paraffin oil(s) and/or wax(es), including, but not limited to, CAS Number 8002-74-2, CAS Number 8009-03-8, CAS Number 8012-95-1, CAS Number 63231-60-7, CAS Number 64742-43-4, CAS Number 64742-56-9, CAS Number 64742-61-6 and 64742-65-0. Nonlimiting examples of paraffin oils and waxes that may be utilized in compositions and methods of the present disclosure include PARRAFINIC OIL 98,5EC (Vioryl S. A., Afidnes, Greece), SUN AG® oils (e.g., 7N and 11N; HollyFrontier Refining & Marketing LLC, Tulsa, OK), SUNSPRAY® oils (e.g., 6E, 6N, 8N, 11N, MLO, ULTRA-FINE®; HollyFrontier Refining & Marketing LLC, Tulsa, OK) and SUNWAX® waxes (e.g., 130, DM-160, DP-116, DS-80, DSl16, DS127, DS137, DS155, LP-127, LP-130, LP-140, LP-155, SP,137, SW-137; HollyFrontier Refining & Marketing LLC, Tulsa, OK).

In some embodiments, the paraffin oil(s) and/or wax(es) comprise(s) about/at least 10, 15, 20, 25, 30, 35, 40, 45, 50, 55, 60, 65, 70, 75, 80, 85, 90, 91, 92, 93, 94, 95, 96, 97, 98, 99, 99.5% or more (by weight) of the carrier. For example, in some embodiments, dodecane comprises about/at least 10, 15, 20, 25, 30, 35, 40, 45, 50, 55, 60, 65, 70, 75, 80, 85, 90, 91, 92, 93, 94, 95, 96, 97, 98, 99, 99.5% or more (by weight) of the carrier.

In some embodiments, methyl soyate comprises about/at least 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, 99.5% or more (by weight) of the inoculant composition. For example, in some embodiments, the paraffin oil(s) and/or wax(es) comprise(s) about/at least 10, 15, 20, 25, 30, 35, 40, 45, 50, 55, 60, 65, 70, 75, 80, 85, 90, 91, 92, 93, 94, 95, 96, 97, 98, 99% or more (by weight) of the inoculant composition.

In some embodiments, inoculant compositions of the present disclosure comprise one or more paraffin oils and/or waxes in an amount/concentration sufficient to ensure microbial cells/spores remain viable therein following:
- storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- desiccation by about 5, 10, 15, 20, 25, 30, 35, 40, 45, 50, 55, 60, 65, 70, 75, 80, 85, 90, 95% or more;
- desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or
- foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more paraffin oils and/or waxes in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microbial cells/spores remain viable following:
- storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- desiccation by about 5, 10, 15, 20, 25, 30, 35, 40, 45, 50, 55, 60, 65, 70, 75, 80, 85, 90, 95% or more;
- desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or
- foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more paraffin oils and/or waxes in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units of the microbial cells/spores remain viable per gram and/or milliliter of inoculant composition following:
- storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
- desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, the carrier comprises one or more carrier components in addition to the paraffin oil(s) and/or wax(es). For example, inoculant compositions of the present disclosure may comprise one or more solid carrier components (e.g., one or more powders and/or granuales) and/or liquid carriers (e.g., one or more aqueous solvents) in addition to the paraffin oil(s) and/or wax(es).

Non-limiting examples of solid carrier components that may be included in compositions of the present disclosure include clays (e.g., attapulgite clays, montmorillonite clay, etc.), peat-based powders and granules, freeze-dried powders, spray-dried powders, spray-freeze-dried powders and combinations thereof.

Non-limiting examples of liquid/gel carrier components that may be included in compositions of the present disclosure include acetone, n-alkylpyrrolidones (e.g., AGSOLEX™ wetting agents; Ashland, Inc., Covington, KY), cycloparaffinic hydrocarbons (e.g., NAPPAR™ 6; ExxonMobil Chemical Company, Spring, TX), decane, dichloromethane, ethanol, ethoxylated alcohols (e.g., TOMADOL® (Air Products and Chemicals, Inc., Allentown, PA), ethyl lactate, hexane, hexylether, isoparaffinic hydrocarbons (e.g., ISOPAR™, ISOPAR™ L, ISOPAR™ M, ISOPAR™ V; ExxonMobil Chemical Company, Spring, TX), isopropanol, methanol, methyl soyate/ethyl lactate co-solvent blends (e.g., STEPOSOL™, Stepan), mineral spirits (e.g., VARSOL™; ExxonMobil Chemical Company, Spring, TX), nonane, oils (e.g., mineral oil, olive oil, peanut oil, soybean oil, sunflower oil, tung oil), pentadecane, petroleum based-oils (e.g., AROMATIC™ and SOLVESSO™ fluids; ExxonMobil Chemical Company, Spring, TX), polyethylene glycols (e.g., PEG 200, PEG 300, PEG 400. etc.), polysorbates (e.g. polysorbate 20, polysorbate 40, polysorbate 60, polysorbate 80, etc.), propan-2-ol, 1,2-propanediol, propylene glycols (e.g., PPG-9, PPG-10, PPG-17, PPG-20, PPG-26, etc.), silicones (siloxanes, trisiloxanes, etc.), TERGITOL™ 15-S surfactants such as TERGITOL™ 15-S-9 (The Dow Chemical Company, Midland, MI), etc.), trichloroethylene, and combinations thereof.

Additional examples of carrier components may be found in BURGES, FORMULATION OF MICROBIAL BIOPESTICIDES: BENEFICIAL MICROORGANISMS, NEMATODES AND SEED TREATMENTS (Springer Science & Business Media) (2012); Inoue & Horikoshi, J. FERMENTATION BIOENG.71(3):194 (1991).

Additional carrier components may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the compositon will be applied, the type(s) of microorganisms in the composition, the number of microorganisms in the composition, the stability of the microorganisms in the composition and storage conditions (e.g., temperature, relative humidity, duration). Those skilled in the art will understand how to select effective amounts/concentrations using routine dose-response experiments. Guidance for the selection of appropriate amounts/concentrations can be found, for example, in International Patent Application Nos. PCT/US2016/050529 and PCT/US20 16/050647 and U.S. Provisional Patent Application Nos. 62/296,798; 62/271,857; 62/347,773; 62/343,217; 62/296,784; 62/271,873; 62/347,785; 62/347, 794; and 62/347,805.

In some embodiments, inoculant compositions of the present disclosure comprise one or more additional carrier components in an amount/concentration of about 1 to about 99% or more (by weight, based upon the total weight of the inoculant composition). For example, inoculant compositions of the present disclosure may comprsise about 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98 or 99% (by weight) of one or more solid carrier components.

Inoculant compositions of the present disclosure may comprise any suitable stabilizing compound(s), including, but not limited to, maltodextrins, monosaccharides, disaccharides, oligosaccharides, sugar alcohols, humic acids, fulvic acids, malt extracts, peat extracts, betaines, prolines, sarcosines, peptones, skim milks, oxidation control components, hygroscopic polymers and UV protectants.

In some embodiments, the inoculant composition comprises one or more maltodextrins (e.g., one or more maltodextrins having a dextrose equivalent value (DEV) of about 3, 4, 5, 6, 7, 8, 9, 10, 11, 12, 13, 14, 15, 16, 17, 18, 19, 20, 21, 22, 23, 24, or 25). According to some embodiments, the inoculant composition comprises one or more maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. According to some embodiments, the inoculant composition comprises a combination of maltodextrins having a DEV of about 5 to about 6, 7, 8, 9, 10, 11, 12, 14, 15, 16, 17, 18, 19 or 20, about 10 to about 11, 12, 14, 15, 16, 17, 18, 19 or 20, or about 15 to about 16, 17, 18, 19 or 20. Non-limiting examples of maltodextrins include MALTRIN® M040 (DEV=5; molecular weight=3600; Grain Processing Corporation, Muscatine, IA), MALTRIN®M100 (DEV=10; molecular weight=1800; Grain Processing Corporation, Muscatine, IA), MALTRIN® M150 (DEV=15; molecular weight=1200; Grain Processing Corporation, Muscatine, IA), MALTRIN® M180 (DEV=18; molecular weight=1050; Grain Processing Corporation, Muscatine, IA), MALTRIN® M200 (DEV=20; molecular weight=900; Grain Processing Corporation, Muscatine, IA), MALTRIN® M250 (DEV=25; molecular weight=720; Grain Processing Corporation, Muscatine, IA); MALTRIN QD® M580 (DEV=16.5-19.9; Grain Processing Corporation, Muscatine, IA); MALTRIN QD®M585 (DEV=15.0-19.9; Grain Processing Corporation, Muscatine, IA); MALTRIN QD® M600 (DEV=20.0-23.0; Grain Processing Corporation, Muscatine, IA); GLOBE® Plus 15 DE (Ingredion Inc., Westchester, IL); and combinations thereof.

In some embodiments, the inoculant composition comprises one or more monosaccharides (e.g., allose, altrose, arabinose, fructose, galactose, glucose, gulose, iodose, lyxose, mannose, ribose, talose, threose and/or xylose). According to some embodiments, the inoculant composition comprises gluscose. According to some embodiments, the inoculant composition does not comprise glucose.

In some embodiments, the inoculant composition comprises one or more disaccharides (e.g., cellobiose, chitobiose, gentiobiose, gentiobiulose, isomaltose, kojibiose, lactose, lactulose, laminaribiose, maltose (e.g., maltose monohydrate, anhydrous maltose), maltulose, mannobiose, melibiose, melibiulose, nigerose, palatinose, rutinose, rutinulose, sophorose, sucrose, trehalose, turanose and/or xylobiose). According to some embodiments, the inoculant composition comprises maltose. According to some embodiments, the inoculant composition does not comprise maltose. According to some embodiments, the inoculant composition comprises trehalose. According to some embodiments, the inoculant composition does not comprise trehalose.

In some embodiments, the inoculant composition comprises one or more oligosaccharides (e.g., fructo-oligosaccharides, galacto-oligosaccharides, mannon-oligosaccharides and/or raffinose).

In some embodiments, the inoculant composition comprises one or more sugar alcohols (e.g., arabitol, erythritol, fucitol, galactitol, glycerol, iditol, inositol, isomalt, lactitol, maltitol, maltotetraitol, maltotriitol, mannitol, polyglycitol, ribitol, sorbitol, threitol, volemitol and/or xylitol).

In some embodiments, the inoculant composition comprises one or more humic acids (e.g., one or more leonardite humic acids, lignite humic acids, peat humic acids and water-extracted humic acids). In some embodiments, the inoculant composition comprises ammonium humate, boron humate, potassium humate and/or sodium humate. In some embodiments, one or more of ammonium humate, boron humate, potassium humate and sodium humate is/are excluded from the inoculant composition.

Nonlimiting examples of humic acids that may be useful in embodiments of the present disclosure include MDL Number MFCD00147177 (CAS Number 1415-93-6), MDL Number MFCD00135560 (CAS Number 68131-04-4), MDL Number MFCS22495372 (CAS Number 68514-28-3), CAS Number 93924-35-7, and CAS Number 308067-45-0.

In some embodiments, the inoculant composition comprises one or more fulvic acids (e.g., one or more leonardite fulvic acids, lignite fulvic acids, peat fulvic acids and/or water-extracted fulvic acids). In some embodiments, the inoculant composition comprises ammonium fulvate, boron fulvate, potassium fulvate and/or sodium fulvate. In some embodiments, one or more of ammonium fulvate, boron fulvate, potassium fulvate and sodium fulvate is/are excluded from inoculant compositions of the present disclosure. Nonlimiting examples of fulvic acids that may be useful in embodiments of the present disclosure include MDL Number MFCD09838488 (CAS Number 479-66-3).

In some embodiments, the inoculant composition comprises one or more betaines (e.g., trimethylglycine).

In some embodiments, the inoculant composition comprises one or more peptones (e.g., bacterial peptones, meat peptones, milk peptones, vegetable peptones and yeast peptones).

In some embodiments, the inoculant composition comprises one or more oxidation control components (e.g., one or more antioxidants and/or oxygen scavengers). According to some embodiments, the inoculant composition comprises one or more oxygen scavengers, such as ascrobic acid, ascorbate salts, catechol and/or sodium hydrogen carbonate. According to some embodiments, the inoculant composition comprises one or more antioxidants, such as ascorbic acid, ascorbyl palmitate, ascorbyl stearate, calcium ascorbate, carotenoids, lipoic acid, phenolic compounds (e.g., flavonoids, flavones, flavonols), potassium ascorbate, sodium ascorbate, thiols (e.g., glutathione, lipoic acid, N-acetyl cysteine), tocopherols, tocotrienols, ubiquinone and/or uric acid. Non-limiting examples of antioxidants include those that are soluble in the cell membrane (e.g., alpha tocopherol (vitamin E), ascorbyl palmitate) and those that are soluble in water (e.g., ascorbic acid and isomers or ascorbic acid, sodium or potassium salts of ascorbic acid or isomers or ascorbic acid, glutathione, sodium or potassium salts of glutathione). In some embodiments, use of a membrane-soluble antioxidant necessitates the addition of one or more surfactants to adequately disperse the antioxidant within the inoculant composition. According to some embodiments, the inoculant composition is/comprises ascorbic acid and/or glutathione.

In some embodiments, the inoculant composition comprises one or more hygroscopic polymers (e.g., hygroscopic agars, albumins, alginates, carrageenans, celluloses, gums (e.g., cellulose gum, guar gum, gum arabic, gum combretum, xanthan gum), methyl celluloses, nylons, pectins, polyacrylic acids, polycaprolactones, polycarbonates, polyethylene glycols (PEG), polyethylenimines (PEI), polylactides, polymethylacrylates (PMA), polyurethanes, polyvinyl alcohols (PVA), polyvinylpyrrolidones (PVP), propylene glycols, sodium carboxymethyl celluloses and/or starches). Non-limiting examples of polymers include AGRIMER™ polymers (e.g., 30, AL-10 LC, AL-22, AT/ATF, VA 3E, VA 31, VA 5E, VA 51, VA 6, VA 6E, VA 7E, VA 71, VEMA AN-216, VEMA AN-990, VEMA AN-1200, VEMA AN-1980, VEMA H-815MS; Ashland Specialty Ingredients, Wilmington, DE), EASYSPERSE™ polymers (Ashland Specialty Ingredients, Wilmington, DE); DISCO™ AG polymers (e.g., L-250, L-280, L-285, L-286, L-320, L-323, L-517, L-519, L-520, L800; Incotec Inc., Salinas, CA), KELZAN® polymers (Bri-Chem Supply Ltd., Calgary, Alberta, CA), SEEDWORX™ polymers (e.g., Bio 200; Aginnovation, LLC, Walnut Groove, CA), TICAXAN® xanthan powders, such as PRE-HYDRATED® TICAXAN® Rapid-3 Powder (TIC Gums, White Marsh, MD) and combinations thereof. Additional examples of polymers may be found in Pouci, et al. AM. J. AGRIC. BIOL. SCI. 3(1):299 (2008).

In some embodiments, the inoculant composition comprises one or more UV protectants (e.g., one or more aromatic amino acids (e.g., tryptophan, tyrosine), carotenoids, cinnamates, lignosulfonates (e.g., calcium lignosulfonate, sodium lignosulfonate), melanins, mycosporines, polyphenols and/or salicylates). Non-limiting examples of UV protectants include Borregaard LignoTech™ lignosulfonates (e.g., Borresperse 3A, Borresperse CA, Borresperse NA, Marasperse AG, Norlig A, Norlig 11D, Ufoxane 3A, Ultrazine NA, Vanisperse CB; Borregaard Lignotech, Sarpsborg, Norway) and combinations thereof.

Additional examples of UV protectants may be found in BURGES, FORMULATION OF MICROBIAL BIOPESTICIDEs: BENEFICIAL MICROORGANISMS, NEMATODES AND SEED TREATMENTS (Springer Science & Business Media) (2012).

Inoculant compositions of the present disclosure may comprise any suitable biostimulant(s), including, but not limited to, seaweed extracts (e.g., Ascophyllum nodosum extracts, such as alginate, Ecklonia maxima extracts, etc.), myo-inositol, glycine and combinations thereof.

Inoculant compositions of the present disclosure may comprise any suitable microbial extract(s), including, but not limited to, bacterial extracts, fungal extracts and combinations thereof. In some embodiments, inoculant compositions of the present disclosure comprise one or more extracts of media comprising one or more diazotrophs, phosphate-solubilizing microorganisms and/or biopesticides. In some embodiments, inoculant compositions of the present disclosure comprise an extract of media comprising one or more of the microbial strains included in Appendix A.

Inoculant compositions of the present disclosure may comprise any suitable nutrient(s), including, but not limited to, organic acids (e.g., acetic acid, citric acid, lactic acid, malic acid, taurine, etc.), macrominerals (e.g., phosphorous, calcium, magnesium, potassium, sodium, iron, etc.), trace minerals (e.g., boron, cobalt, chloride, chromium, copper, fluoride, iodine, iron, manganese, molybdenum, selenium, zinc, etc.), vitamins, (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_5$, vitamin $B_9$, vitamin $B_{12}$, choline) vitamin C, vitamin D, vitamin E, vitamin K, carotenoids (α-carotene, β-carotene, cryptoxanthin, lutein, lycopene, zeaxanthin, etc.) and combinations thereof. In some embodiments, inoculant compositions of the present disclosure comprise phosphorous, boron, chlorine, copper, iron, manganese, molybdenum and/or zinc.

Inoculant compositions of the present disclosure may comprise any suitable pest attractant(s) and/or feeding stimulant(s), including, but not limited to, brevicomin, ceralure, codlelure, cue-lure, disparlure, dominicalure, eugenol, frontalin, gossyplure, grandlure, hexalure, ipsdienol, ipsenol, japonilure, latitlure, lineatin, litlure, looplure, medlure, megatomic acid, methyl eugenol, moguchun, α-multistriatin, muscalure, orfalure, oryctalure, ostramone, rescalure, siglure, sulcatol, trimedlure and/or trunc-call.

Inoculant compositions of the present disclosure may comprise any suitable pesticide(s), including, but not limited to, acaricides, fungicides, herbicides, insecticides and nematicides.

Fungicides may be selected to provide effective control against a broad spectrum of phytopathogenic fungi (and fungus-like organisms), including, but not limited to, soil-borne fungi from the classes Ascomycetes, Basidiomycetes, Chytridiomycetes, Deuteromycetes (syn. Fungi imperfecti), Peronosporomycetes (syn. Oomycetes), Plasmodiophoromycetes and Zygomycetes.

According to some embodiments, the inoculant composition comprises a fungicide (or combination of fungicides) that is toxic to one or more strains of Albugo (e.g., A. candida), Alternaria (e.g., A. alternata), Aspergillus (e.g., A. candidus, A. clavatus, A. flavus, A. fumigatus, A. parasiticus, A. restrictus, A. sojae, A. solani), Blumeria (e.g., B. graminis), Bonytis (e.g., B. cinerea), Cladosporum (e.g., C. cladosporioides), Colletotrichum (e.g., C. acutatum, C. boninense, C. capsici, C. caudatum, C. coccodes, C. crassipes, C. dematium, C. destructivum, C. fragariae, C. gloeosporioides, C. graminicola, C. kehawee, C. lindemuthianum, C. musae, C. orbiculare, C. spinaceae, C. sublineolum, C. trifolii, C. truncatum), Fusarium (e.g., F. graminearum, F. moniliforme, F. oxysporum, F. roseum, F. tricinctum), Helminthosporium, Magnaporthe (e.g., M. grisea, M. orvzae), Melamspora (e.g., M. lini), Mycosphaerella (e.g., M. graminicola), Nematospora, Penicillium (e.g., P. rugulosum, P. verrucosum), Phakopsora (e.g., P. pachyrhizi), Phomopsis, Phytiphtoria (e.g., P. infestans), Puccinia (e.g., P. graminis, P. striiformis, P. tritici, P. triticina), Pucivinia (e.g., P. graministice), Pythium, Pytophthora, Rhizoctonia (e.g., R. solani), Scopulariopsis, Selerotinia, Thielaviopsis and/or Ustilago (e.g., U. maydis). Additional examples of fungi may be found in Bradley, Managing Diseases, in ILLINOIS AGRONOMY HANDBOOK (2008).

Herbicides may be selected to provide effective control against a broad spectrum of plants, including, but not limited to, plants from the families Asteraceae, Caryophyllaceae, Poaceae and Polygonaceae. According to some embodiments, the inoculant composition comprises an herbicide (or combination of herbicides) that is toxic to one or more strains of Echinochloa (e.g., E. brevipedicellata, E. callopus, E. chacoensis, E. colona, E. crus-galli, E. crus-pavonis, E. elliptica, E. esculenta, E. frumentacea, E. glabrescens, E. haploclada, E. helodes, E. holciformis, E. inundata, E. jaliscana, E. Jubata, E. kimberleyensis, E. lacunaria, E. macrandra, E. muricata, E. obtusiflora, E. oplismenoides, E. orzyoides, E. paludigeno, E. picta, E. pithopus, E. polystachya, E. praestans, E. pyramidalis, E. rotundiflora, E. stagnina, E. telmatophila, E. turneriana, E. ugandensis, E. walteri), Fallopia (e.g., F. baldschuanica, F. japonica, F. sachalinensis), Stellaria (e.g., S. media) and/or Taraxacum (e.g., T. albidum, T. aphrogenes, T. brevicorniculatum. T. californicum, T. centrasiatum, T. ceratophorum, T. erythrospermum, T. farinosum, T. holmboei, T. japonicum, T. kok-saghyz, T. laevigatum T officinale, T. platycarpum). Additional species of plants that may be targeted by inoculant compositions of the present disclosure may be found in Hager, Weed Management, in ILLINOIS AGRONOMY HANDBOOK (2008) and LOUX ET AL., WEED CONTROL GUIDE FOR OHIO, INDIANA AND ILLINOIS (2015).

Insecticides may be selected to provide effective control against a broad spectrum of insects, including, but not limited to, insects from the orders Coleoptera, Dermaptera, Diptera, Hemiptera, Homoptera, Hymenoptera, Lepidoptera, Orthoptera and Thysanoptera. For example, inoculant compositions of the present disclosure may comprise one or more insecticides toxic to insects from the families Acrididae, Aleytodidae, Anobiidae, Anthomyiidae, Aphididae, Bostrichidae, Bruchidae, Cecidomyiidae, Cerambycidae, Cercopidae, Chrysomelidae, Cicadellidae, Coccinellidae, Cryllotalpidae, Cucujidae, Curculionidae, Dermestidae, Elateridae, Gelechiidae, Lygaeidae, Meloidae, Membracidae, Miridae, Noctuidae, Pentatomidae, Pyralidae, Scarabaeidae, Silvanidae, Spingidae, Tenebrionidae and/or Thripidae. According to some embodiments, the inoculant composition comprises an insecticide (or combination of insecticides) that is toxic to one or more species of *Acalvmma*, Acanthaoscelides (e.g., *A. obtectus,*), *Anasa* (e.g., *A. tristis*), Anastrepha (e.g., A. ludens), *Anoplophora* (e.g., *A. glabripennis*), *Anthonomus* (e.g., *A. eugenii*), *Acyrthosiphon* (e.g., *A. pisum*), Bactrocera (e.g., B. dosalis), *Bemisia* (e.g., *B. argentifolii, B. tabaci*), *Brevicoryne* (e.g., *B. brassicae*), Bruchidius (e.g., B. atrolineatus), *Bruchus* (e.g., *B. atomarius, B. dentipes, B. lentis, B. pisorum* and/or *B. rufipes*), Callosobruchus (e.g., *C. chinensis, C. maculatus*, C. rhodesianus, C. subinnotatus, C. *theobromae*), Caryedon (e.g., C. serratus), Cassadinae, *Ceratitis* (e.g., *C. capitata*), Chrysomelinae, Circulifer (e.g., *C. tenellus*), Criocerinae, Cryptocephalinae, Cryptolestes (e.g., *C. ferrugineus*, C. pusillis, C. pussilloides), Cylas (e.g., C. formicarius), *Delia* (e.g., *D. antiqua*), *Diabrotica, Diaphania* (e.g., *D. nitidalis*), Diaphorina (e.g., *D. citri*), Donaciinae, Ephestia (e.g, E. cautella, E. elutella, E., keuhniella), *Epilachna* (e.g., *E. varivestris*), *Epiphyas* (e.g., E. postrittana), Eumolpinae, Galerucinae, *Helicoverpa* (e.g., *H. zea*), Heteroligus (e.g., f. meles), *Iobesia* (e.g., *I. botrana*), Lamprosomatinae, Lasioderma (e.g., L. serricorne), *Leptinotarsa* (e.g., *L. decemlineata*), *Leptoglossus, Liriomyza* (e.g., *L. trifolii*), Manducca, Melittia (e.g., M. cucurbitae), *Myzus* (e.g., *M. persicae*), *Nezara* (e.g., *N. viridula*), Orzaephilus (e.g., O. merator, O. surinamensis), *Ostrinia* (e.g., *O. nubilalis*), *Phthorimaea* (e.g., *P. operculella*), *Pieris* (e.g., *P. rapae*), Plodia (e.g., P. interpunctella), *Plutella* (e.g., *P. xylostella*), *Popillia* (e.g., *P. japonica*), Prostephanus (e.g., P. truncates), *Psila*, Rhizopertha (e.g., R. dominica), *Rhopalosiphum* (e.g., *R. maidis*), Sagrinae, *Solenopsis* (e.g., *S. Invicta*), Spilopyrinae, *Sitophilus* (e.g., S. granaries, S. orvzae and/or S. zeamais), *Sitotroga* (e.g., *S. cerealella*), *Spodoptera* (e.g., *S. frugiperda*), Stegobium (e.g., S. paniceum), Synetinae, *Tenebrio* (e.g., *T. malens* and/or *T. molitor*), *Thrips* (e.g., *T. tabaci*), *Trialeurodes* (e.g., *T. vaporariorum*), Tribolium (e.g., T. castaneum and/or T. confusum), *Trichoplusia* (e.g., *T. ni*), Trogoderma (e.g., T. granarium) and Trogossitidae (e.g., T. mauritanicus). Additional species of insects that may be targeted by inoculant compositions of the present disclosure may be found in CAPINERA, HANDBOOK OF VEGETABLE PESTS (2001) and Steffey and Gray, Managing Insect Pests, in ILLINOIS AGRONOMY HANDBOOK (2008).

Nematicides may be selected to provide effective control against a broad spectrum of nematodes, including, but not limited to, phytoparasitic nematodes from the classes Chromadorea and Enoplea. According to some embodiments, the inoculant composition comprises a nematicide (or combination of nematicides) that is toxic to one or more strains of *Anguina, Aphelenchoides, Belonolaimus, Bursaphelenchus, Ditylenchus, Globodera, Helicotylenchus, Heterodera, Hirschmanniella, Meloidogyne, Naccobus, Pratylenchus, Radopholus, Rotylenshulus, Trichodorus, Tylenchulus* and/ or *Xiphinema*. Additional species that may be targeted by inoculant compositions of the present disclosure may be found in CAPINERA, HANDBOOK OF VEGETABLE PESTS (2001) and Niblack, Nematodes, in ILLINOIS AGRONOMY HANDBOOK (2008).

In some embodiments, inoculant compositions of the present disclosure comprise one or more chemical fungicides. Non-limiting examples of chemical fungicides include strobilurins, such as azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide; carboxamides, such as carboxanilides (e.g., benalaxyl, benalaxyl-M, benodanil, bixafen, boscalid, carboxin, fenfuram, fenhexamid, flutolanil, fluxapyroxad, furametpyr, isopyrazam, isotianil, kiralaxyl, mepronil, metalaxyl, metalaxyl-M (mefenoxam), ofurace, oxadixyl, oxycarboxin, penflufen, penthiopyrad, sedaxane, tecloftalam, thifluzamide, tiadinil, 2-amino-4-methyl-thiazole-5-carboxanilide, N-(4'-trifluoromethylthiobiphenyl-2-yl)-3-difluoromethyl-1-methyl-1H-pyra-zole-4-carboxamide, N-(2-(1,3,3-trimethylbutyl)-phenyl)-1,3-dimethyl-5-fluoro-1 H-pyrazole-4-carboxamide), carboxylic morpholides (e.g., dimethomorph, flumorph, pyrimorph), benzoic acid amides (e.g., flumetover, fluopicolide, fluopyram, zoxamide), carpropamid, dicyclomet, mandiproamid, oxytetracyclin, silthiofam and N-(6-methoxy-pyridin-3-yl) cyclopropanecarboxylic acid amide; azoles, such as triazoles (e.g., azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole) and imidazoles (e.g., cyazofamid, imazalil, pefurazoate, prochloraz, triflumizol); heterocyclic compounds, such as pyridines (e.g., fluazinam, pyrifenox (cf.Dlb), 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine), pyrimidines (e.g., bupirimate, cyprodinil, diflumetorim, fenarimol, ferimzone, mepanipyrim, nitrapyrin, nuarimol, pyrimethanil), piperazines (e.g., triforine), pirroles (e.g., fenpiclonil, fludioxonil), morpholines (e.g., aldimorph, dodemorph, dodemorph-acetate, fenpropimorph, tridemorph), piperidines (e.g., fenpropidin), dicarboximides (e.g., fluoroimid, iprodione, procymidone, vinclozolin), non-aromatic 5-membered heterocycles (e.g., famoxadone, fenamidone, flutianil, octhilinone, probenazole, 5-amino-2-isopropyl-3-oxo-4-ortho-tolyl-2,3-dihydro-pyrazole-1-carbothioic acid S-allyl ester), acibenzolar-S-methyl, ametoctradin, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole and 5-chloro-7-(4-methylpiperidin-1-yl)-6-(2,4,6-trifluorophenyl)-[1,2,4]triazolo-[1,5-a] pyrimidine; benzimidazoles, such as carbendazim; and other active substances, such as guanidines (e.g., guanidine, dodine, dodine free base, guazatine, guazatine-acetate, iminoctadine), iminoctadine-triacetate and iminoctadine-tris(albesilate); antibiotics (e.g., kasugamycin, kasugamycin hydrochloride-hydrate, streptomycin, polyoxine and validamycin A); nitrophenyl derivates (e.g., binapacryl, dicloran, dinobuton, dinocap, nitrothal-isopropyl, teenazen); organometal compounds (e.g., fentin salts, such as fentinacetate, fentin chloride, fentin hydroxide); sulfur-containing heterocyclyl compounds (e.g., dithianon, isoprothiolane); organophosphorus compounds (e.g., edifenphos, fosetyl, fosetyl-aluminum, iprobenfos, phosphorus acid and its salts, pyrazophos, tolclofos-methyl); organochlorine compounds (e.g., chlorothalonil, dichlofluanid, dichlorophen, flusulfamide, hexachlorobenzene, pencycuron, pentachlorphenole and its salts, phthalide, quintozene, thiophanate-methyl, thiophanate, tolylfluanid, N-(4-chloro-2-nitro-phenyl)-N-ethyl-4-methyl-benzenesulfonamide) and inorganic active substances (e.g., Bordeaux mixture, copper acetate, copper hydroxide, copper oxychloride, basic copper sulfate, sulfur) and combinations thereof. In some embodiments, inoculant compositions of the present disclosure comprise acibenzolar-S-methyl, azoxystrobin, benalaxyl, bixafen, boscalid, carbendazim, cyproconazole, dimethomorph, epoxiconazole, fludioxonil, fluopyram, fluoxastrobin, flutianil, flutolanil, fluxapyroxad, fosetyl-Al, ipconazole, isopyrazam, kresoxim-methyl, mefenoxam, metalaxyl, metconazole, myclobutanil, orysastrobin, penflufen, penthiopyrad, picoxystrobin, propiconazole, prothioconazole, pyraclostrobin, sedaxane, silthiofam, tebuconazole, thiabendazole, thifluzamide, thiophanate, tolclofos-methyl, trifloxystrobin and triticonazole. In some embodiments, inoculant compositions of the present disclosure comprise azoxystrobin, pyraclostrobin, fluoxastrobin, trifloxystrobin, ipconazole, prothioconazole, sedaxane, fludioxonil, metalaxyl, mefenoxam, thiabendazole, fluxapyroxad and/or fluopyram. In some embodiments, inoculant compositions of the present disclosure comprise one or more aromatic hydrocarbons, benzimidazoles, benzthiadiazole, carboxamides, carboxylic acid amides, morpholines, phenylamides, phosphonates, quinone outside inhibitors (e.g. strobilurins), thiazolidines, thiophanates, thiophene carboxamides and/or triazoles.

In some embodiments, inoculant compositions of the present disclosure comprise one or more chemical herbicides. Non-limiting examples of chemical herbicides include 2,4-dichlorophenoxyacetic acid (2,4-D), 2,4,5-trichlorophenoxyacetic acid (2,4,5-T), ametryn, amicarbazone, aminocyclopyrachlor, acetochlor, acifluorfen, alachlor, atrazine, azafenidin, bentazon, benzofenap, bifenox, bromacil, bromoxynil, butachlor, butafenacil, butroxydim, carfentrazone-ethyl, chlorimuron, chlorotoluro, clethodim, clodinafop, clomazone, cyanazine, cycloxydim, cyhalofop, desmedipham, desmetryn, dicamba, diclofop, dimefuron, diuron, dithiopyr, fenoxaprop, fluazifop, fluazifop-P, fluometuron, flufenpyrethyl, flumiclorac-pentyl, flumioxazin, fluoroglycofen, fluthiacet-methyl, fomesafe, fomesafen, glyphosate, glufosinate, haloxyfop, hexazinone, imazamox, imazaquin, imazethapyr, ioxynil, isoproturon, isoxaflutole, lactofen, linuron, mecoprop, mecoprop-P, mesotrion, metamitron, metazochlor, methibenzuron, metolachlor (and S-metolachlor), metoxuron, metribuzin, monolinuron, oxadiargyl, oxadiazon, oxyfluorfen, phenmedipham, pretilachlor, profoxydim, prometon, prometry, propachlor, propanil, propaquizafop, propisochlor, pyraflufen-ethyl, pyrazon, pyrazolynate, pyrazoxyfen, pyridate, quizalofop, quizalofop-P (e.g., quizalofop-ethyl, quizalofop-P-ethyl, clodinafop-propargyl, cyhalofop-butyl, diclofop-methyl, fenoxaprop-P-ethyl, fluazifop-P-butyl, haloxyfop-methyl, haloxyfop-R-methyl), saflufenacil, sethoxydim, siduron, simazine, simetryn, sulcotrione, sulfentrazone, tebuthiuron, tembotrione, tepraloxydim, terbacil, terbumeton, terbuthylazine, thaxtomin (e.g., the thaxtomins described in U.S. Pat. No. 7,989,393), thenylchlor, tralkoxydim, triclopyr, trietazine, tropramezone, salts and esters thereof; racemic mixtures and resolved isomers thereof and combinations thereof. In some embodiments, inoculant compositions of the present disclosure comprise acetochlor, clethodim, dicamba, flumioxazin, fomesafen, glyphosate, glufosinate, mesotrione, quizalofop, saflufenacil, sulcotrione, S-3100 and/or 2,4-D. In some embodiments, inoculant compositions of the present disclosure comprise glyphosate, glufosinate, dicamba, 2,4-D, acetochlor, metolachlor, pyroxasulfone, flumioxazin, fomesafen, lactofen, metribuzin, mesotrione, and/ or ethyl 2-((3-(2-chloro-4-fluoro-5-(3-methyl-2,6-dioxo-4-(trifluoromethyl)-2,3-dihydropyrimidin-1(6H)-yl)phenoxy) pyridin-2-yl)oxy)acetate. In some embodiments, inoculant compositions of the present disclosure comprise one or more acetyl CoA carboxylase (ACCase) inhibitors, acetolactate synthase (ALS) inhibitors, acetohydroxy acid synthase (AHAS) inhibitors, photosystem II inhibitors, photosystem I inhibitors, protoporphyrinogen oxidase (PPO or Protox) inhibitors, carotenoid biosynthesis inhibitors, enolpyruvyl shikimate-3-phosphate (EPSP) synthase inhibitor, glutamine synthetase inhibitor, dihydropteroate synthetase inhibitor, mitosis inhibitors, 4-hydroxyphenyl-pyruvate-dioxygenase (4-HPPD) inhibitors, synthetic auxins, auxin herbicide salts, auxin transport inhibitors, nucleic acid inhibitors and/or one or more salts, esters, racemic mixtures and/or resolved isomers thereof.

In some embodiments, inoculant compositions of the present disclosure comprise one or more chemical insecticides and/or nematicides. Non-limiting examples of chemical insecticides and nematicides include acrinathrin, alpha-cypermethrin, betacyfluthrin, cyhalothrin, cypermethrin, deltamethrin, esfenvalcrate, etofenprox, fenpropathrin, fenvalerate, flucythrinate, fosthiazate, lambda-cyhalothrin, gamma-cyhalothrin, permethrin, tau-fluvalinate, transfluthrin, zeta-cypermethrin, cyfluthri, bifenthrin, tefluthrin, eflusilanat, fubfenprox, pyrethrin, resmethrin, imidacloprid, acetamiprid, thiamethoxam, nitenpyram, thiacloprid, dinotefuran, clothianidin, imidaclothiz, chlorfluazuron, diflubenzuron, lufenuron, teflubenzuron, triflumuron, novaluron, flufenoxuron, hexaflumuron, bistrifluoron, noviflumuron, buprofezin, cyromazine, methoxyfenozide, tebufenozide, halofenozide, chromafenozide, endosulfan, fipronil, ethiprole, pyrafluprole, pyriprole, flubendiamide, chlorantraniliprole (e.g., Rynaxypyr), cyazypyr, emamectin, emamectin benzoate, abamectin, ivermectin, milbemectin, lepimectin, tebufenpyrad, fenpyroximate, pyridaben, fenazaquin, pyrimidifen, tolfenpyrad, dicofol, cyenopyrafen, cyflumetofen, acequinocyl, fluacrypyrin, bifenazate, diafenthiuron, etoxazole, clofentezine, spinosad, triarathen, tetradifon, propargite, hexythiazox, bromopropylate, chinomethionat, amitraz, pyrifluquinazon, pymetrozine, flonicamid, pyriproxyfen, diofenolan, chlorfenapyr, metaflumizone, indoxacarb, chlorpyrifos, spirodiclofen, spiromesifen, spirotetramat, pyridalyl, spinctoram, acephate, triazophos, profenofos, oxamyl, spinetoram, fenamiphos, fenamipclothiahos, 4-{[(6-chloropyrid-3-yl) methyl](2,2-difluoroethyl)amino}furan-2(5H)-one, cadusaphos, carbaryl, carbofuran, ethoprophos, thiodicarb, aldicarb, aldoxycarb, metamidophos, methiocarb, sulfoxaflor, cyantraniliprole and tioxazofen and combinations thereof. In some embodiments, inoculant compositions of the present disclosure comprise abamectin, aldicarb, aldoxycarb, bifenthrin, carbofuran, chlorantraniliporle, chlothianidin, cyfluthrin, cyhalothrin, cypermethrin, cyantraniliprole, deltamethrin, dinotefuran, emamectin, ethiprole, fenamiphos, fipronil, flubendiamide, fosthiazate, imidacloprid, ivermectin, lambda-cyhalothrin, milbemectin, nitenpyram, oxamyl, permethrin, spinetoram, spinosad, spirodichlofen, spirotetramat, tefluthrin, thiacloprid, thiamethoxam and/or thiodicarb. In some embodiments, inoculant compositions of the present disclosure comprise one or more carbamates, diamides, macrocyclic lactones, neonicotinoids, organophosphates, phenylpyrazoles, pyrethrins, spinosyns, synthetic pyrethroids, tetronic acids and/or tetramic acids. In some embodiments, inoculant compositions of the present disclosure comprise an insecticide selected from the group consisting of clothianidin, thiamethoxam, imidacloprid, cyantraniliprole, chlorantraniliprole, fluopyram and tioxazafen.

In some embodiments, inoculant compositions of the present disclosure comprise one or more biopesticides (e.g., one or more biofungicides, bioinsecticides and/or bionematicides). Examples of microbial strains that exhibit biopesticidal activity are included in Appendix A, along with strains that exhibit nitrogen-fixing activity, phosphate-solubilizing activity, etc. Additional examples of pesticides may be found in Bradley, Managing Diseases, in ILLINOIS AGRONOMY HANDBOOK (2008); Hager, Weed Management, in ILLINOIS AGRONOMY HANDBOOK (2008); LOUX FT AL., WEED CONTROL GUIDE FOR OHIO, INDIANA AND ILLINOIS (2015); Niblack, Nematodes, in ILLINOIS AGRONOMY HANDBOOK (2008); and Steffey and Gray, Managing Insect Pests, in ILLINOIS AGRONOMY HANDBOOK (2008).

Inoculant compositions of the present disclosure may comprise any suitable plant signal molecule(s).

$$\text{(I)}$$

in which G is a hexosamine which can be substituted, for example, by an acetyl group on the nitrogen, a sulfate group, an acetyl group and/or an ether group on an oxygen; $R_1$, $R_2$, $R_3$, $R_5$, $R_6$ and $R_7$, which may be identical or different, represent H, $CH_3$ CO—, $C_x H_y$ CO— where x is an integer between 0 and 17 and y is an integer between 1 and 35, or any other acyl group such as, for example, a carbamoyl; $R_4$ represents a saturated or mono-, di- or tri-unsaturated aliphatic chain containing at least 12 carbon atoms; and n is an integer between 1 and 4.

In some embodiments, inoculant compositions of the present disclosure comprise one or more LCOs represented by formula II:

$$\text{(II)}$$

Inoculant compositions of the present disclosure may comprise any suitable LCO(s). LCOs, sometimes referred to as symbiotic nodulation (Nod) signals or Nod factors, consist of an oligosaccharide backbone of p3-1,4-linked N-acetyl-D-glucosamine ("GIcNAc") residues with an N-linked fatty acyl chain condensed at the non-reducing end. LCOs differ in the number of GIcNAc residues in the backbone, in the length and degree of saturation of the fatty acyl chain and in the substitutions of reducing and non-reducing sugar residues. See, e.g., Denarie, et al., ANN. REV. BIOCHEM. 65:503 (1996); Hamel, et al., PLANTA 232:787 (2010); Prome, et al., PURE & APPL. CHEM. 70(1):55 (1998).

In some embodiments, inoculant compositions of the present disclosure comprise one or more LCOs represented by formula I:

in which R represents H or $CH_3$ CO— and n is equal to 2 or 3. See, e.g., U.S. Pat. No. 5,549,718. A number of Bradyrhizobium japonicum-derived LCOs have also been described, including BjNod-V (C18:1), BjNod-V ($A_C$, C18:1), BjNod-V (C16:1) and BjNod-V ($A_C$, C16:0) (with "V" indicating the presence of five N-acetylglucosamines, "Ac" an acetylation, the number following the "C" indicating the number of carbons in the fatty acid side chain and the number following the ":" indicating the number of double bonds). See, e.g., U.S. Pat. Nos. 5,175,149 and 5,321,011. Additional LCOs obtained from bacterial strains include NodRM, NodRM-1, NodRM-3. When acetylated (the R=$CH_3$ CO—), they become AcNodRM-1 and AcNodRM-3, respectively (U.S. Pat. No. 5,545,718).

In some embodiments, inoculant compositions of the present disclosure comprise one or more LCOs represented by formula III:

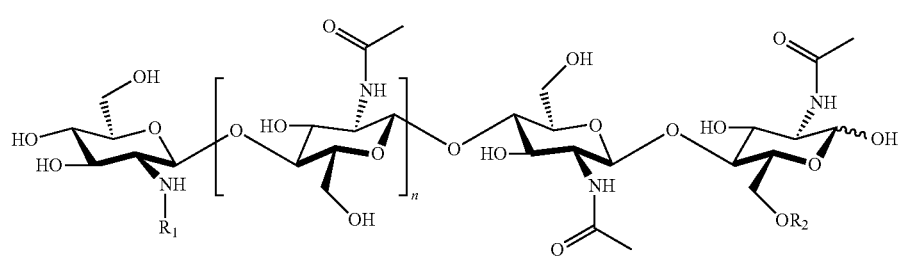

in which n=1 or 2; $R_1$ represents C16, C16:0, C16:1, C16:2, C18:0, C18:1Δ9Z or C18:1 Δ11Z; and $R_2$ represents hydrogen or $SO_3H$.

In some embodiments, inoculant compositions of the present disclosure comprise one or more LCOs represented by formula IV:

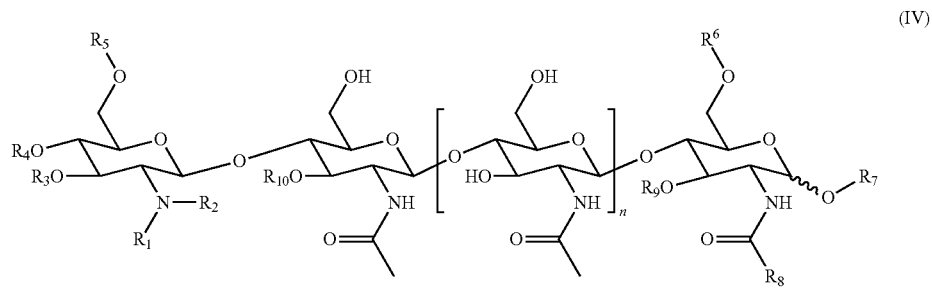

in which $R_1$ represents C14:0, 30H—C14:0, iso-C15:0, C16:0, 3-OH—C16:0, iso-C15:0, C16:1, C16:2, C16:3, iso-C17:0, iso-C17:1, C18:0, 30H—C18:0, C18:0/3-OH, C18:1, OH—C18:1, C18:2, C18:3, C18:4, C19:1 carbamoyl, C20:0, C20:1, 3—OH—C20:1, C20:1/3-OH, C20:2, C20:3, C22:1 and C18-26((ω-1)-OH (which according to D'Haeze, et al., Glycobiology 12:79R-105R (2002), includes C18, C20, C22, C24 and C26 hydroxylated species and C16:1Δ9, C16:2 (Δ2, 9) and C16:3 (Δ2,4,9)); $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, $SO_3H$, sulfate ester, 3-O—S-2-O-MeFuc, 2-O-MeFuc and 4-O-AcFuc; $R_7$ represents hydrogen, mannosyl or glycerol; $R_8$ represents hydrogen, methyl, or —$CH_2OH$; $R_9$ represents hydrogen, arabinosyl, or fucosyl; $R_{10}$ represents hydrogen, acetyl or fucosyl; and n represents 0, 1, 2 or 3. Naturally occurring LCOs embraced by this structure are described in D'Haeze, et al., supra.

Further examples of LCOs that may be useful in compositions and methods of the present disclosure are provided below as structures V-XXXIII:

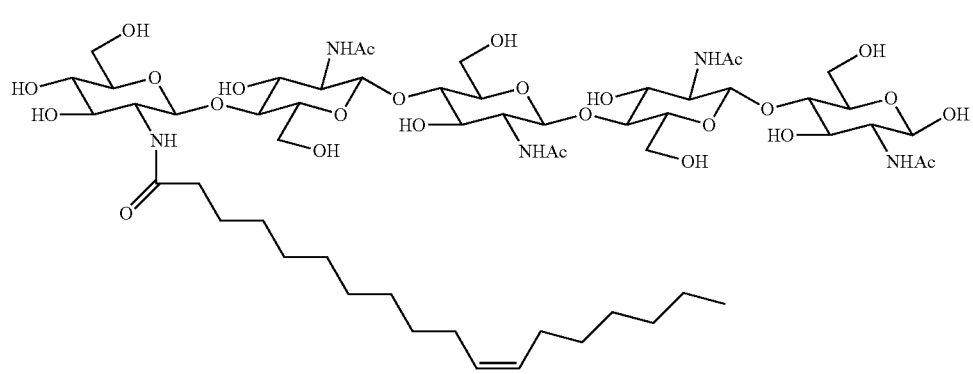

-continued
(VI)
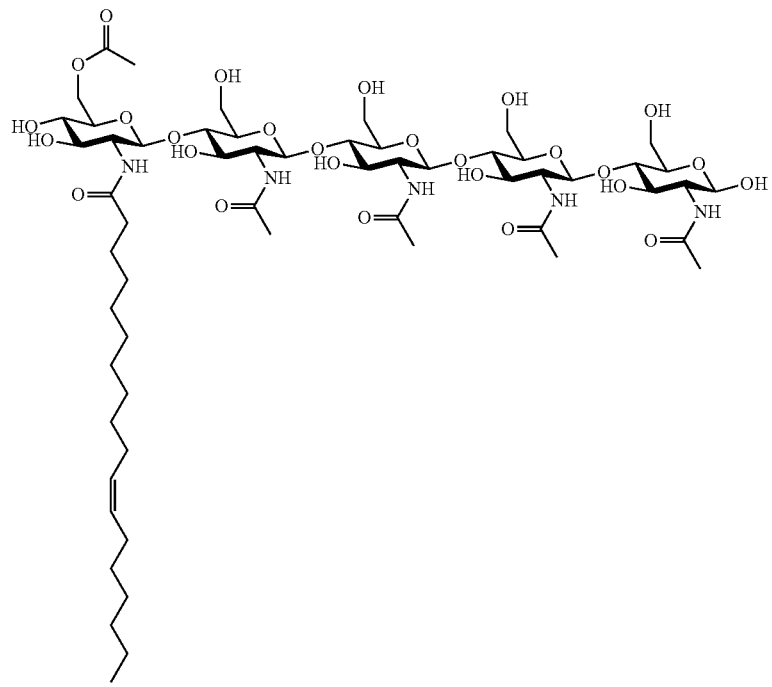
(VII)
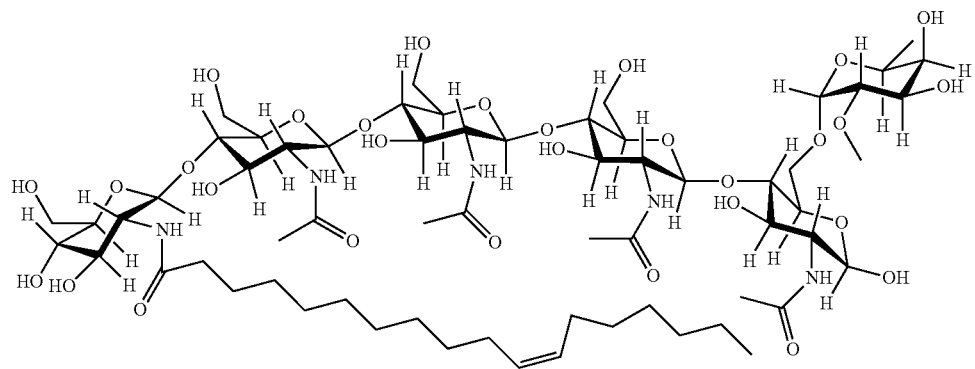

-continued
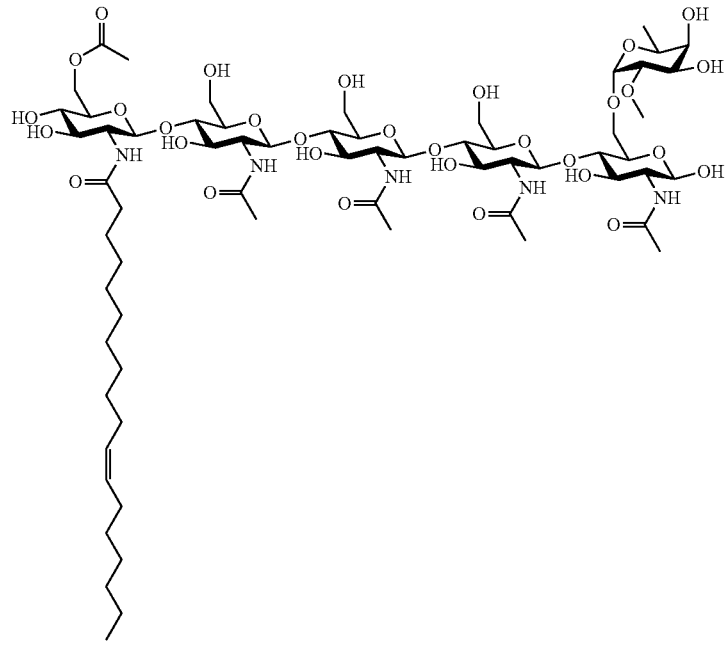
(VIII)
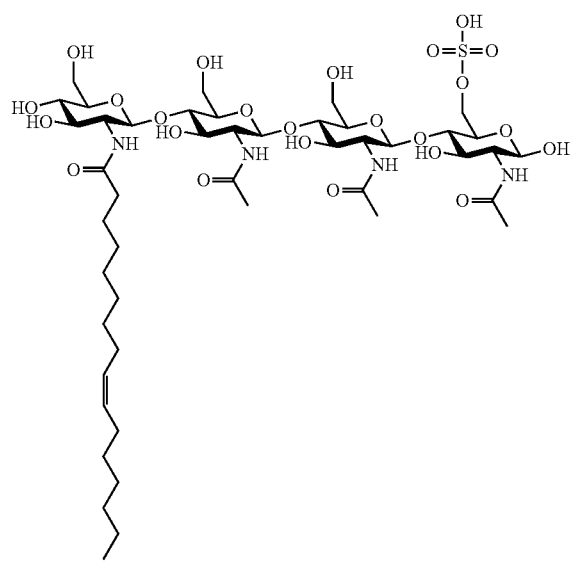
(IX)
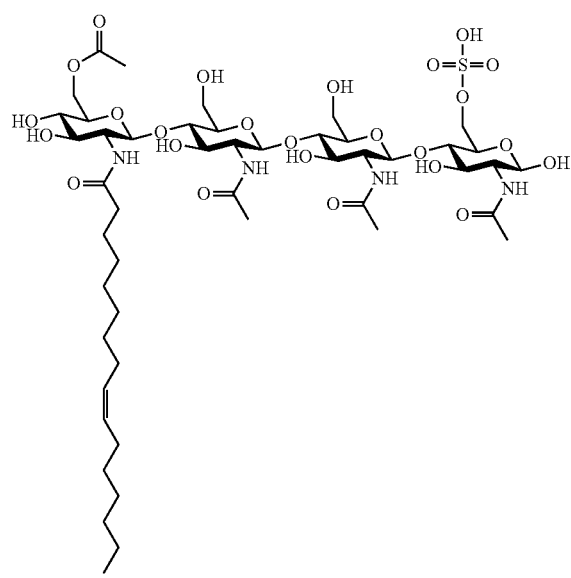
(X)
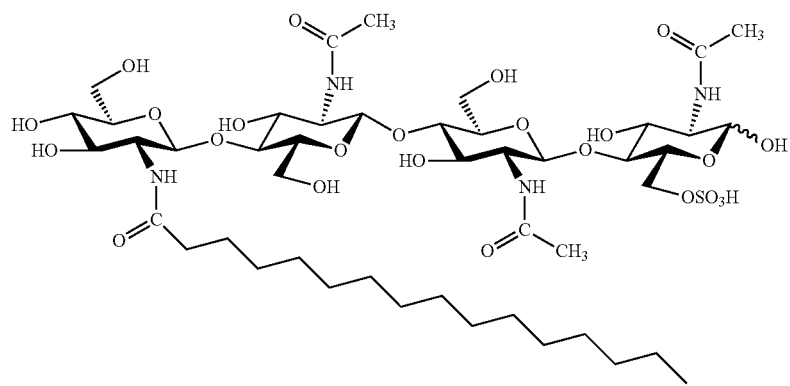
(XI)

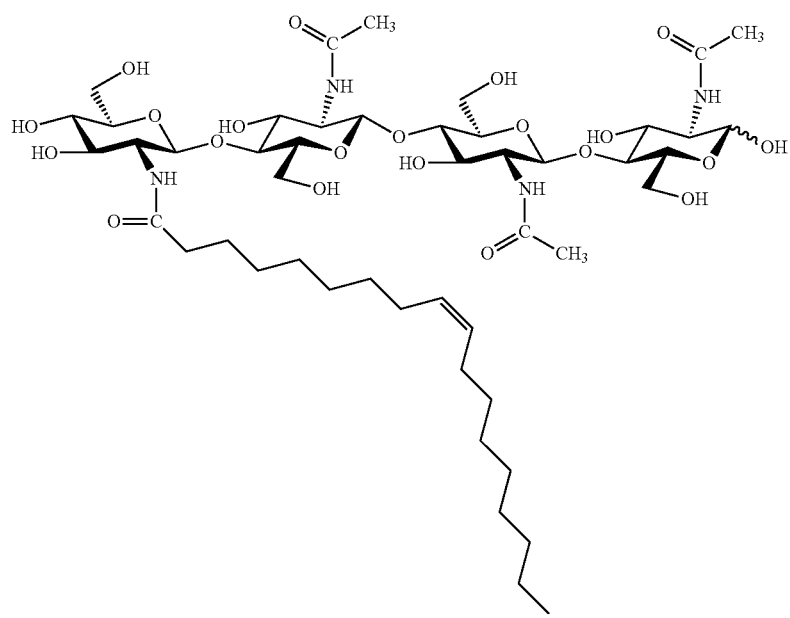
(XII)
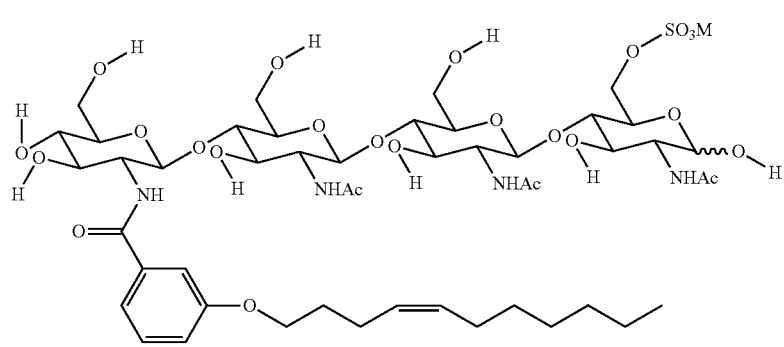
(XIII)
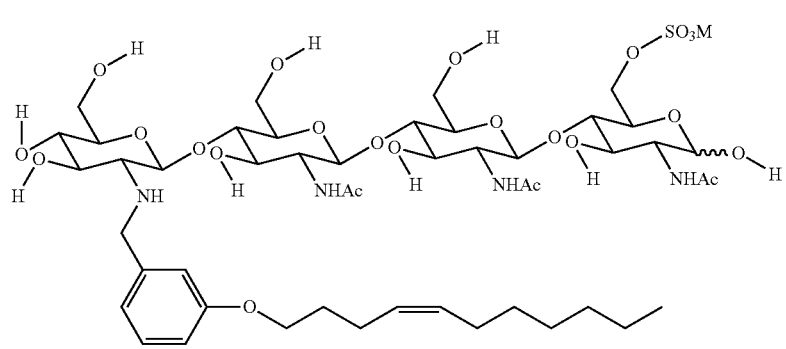
(XIV)
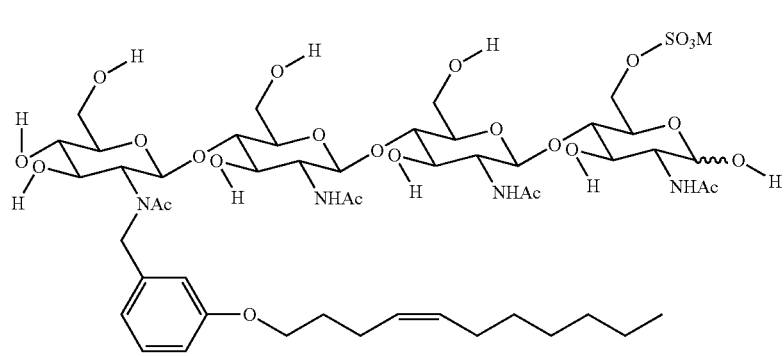
(XV)

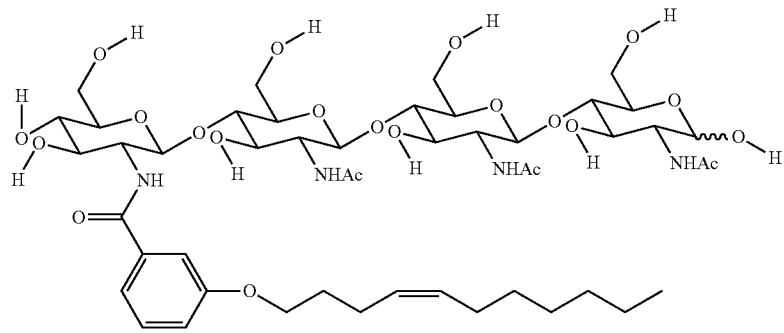
(XVI)
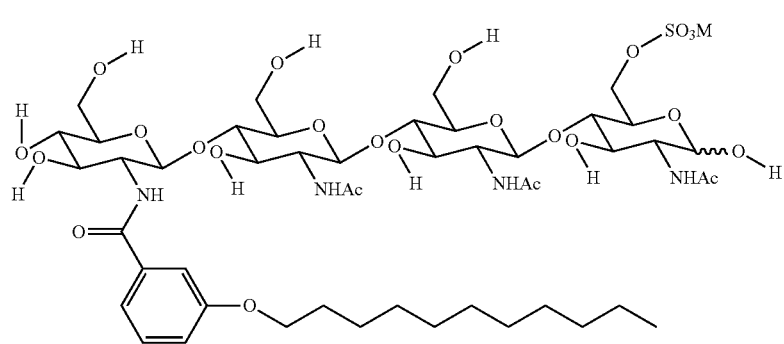
(XVII)
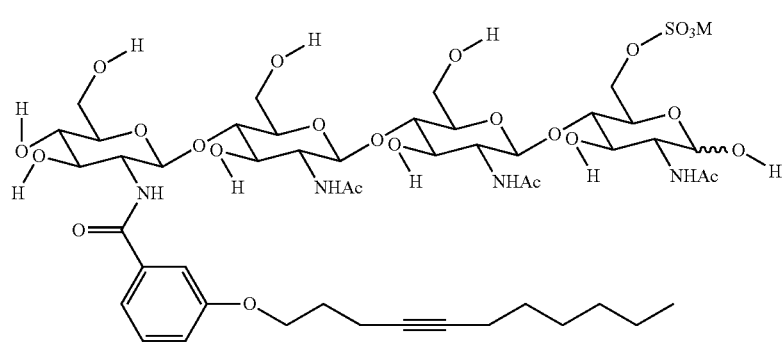
(XVIII)
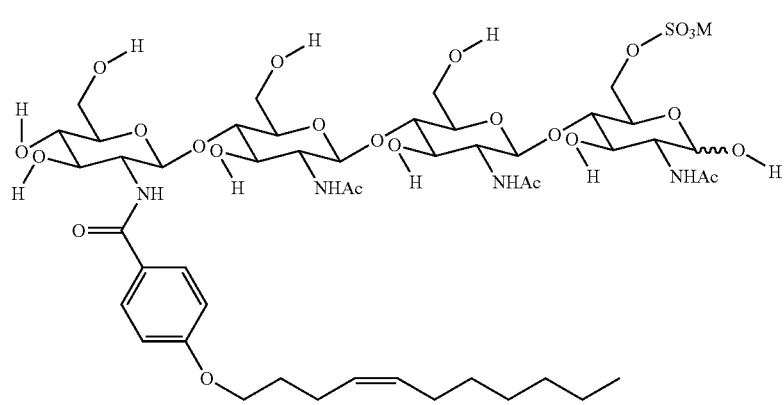
(XIX)

-continued
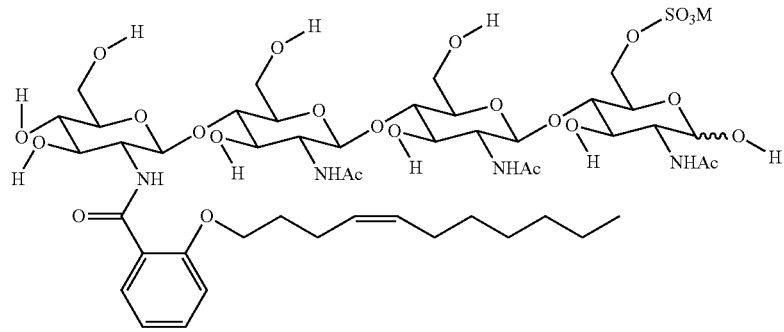
(XX)
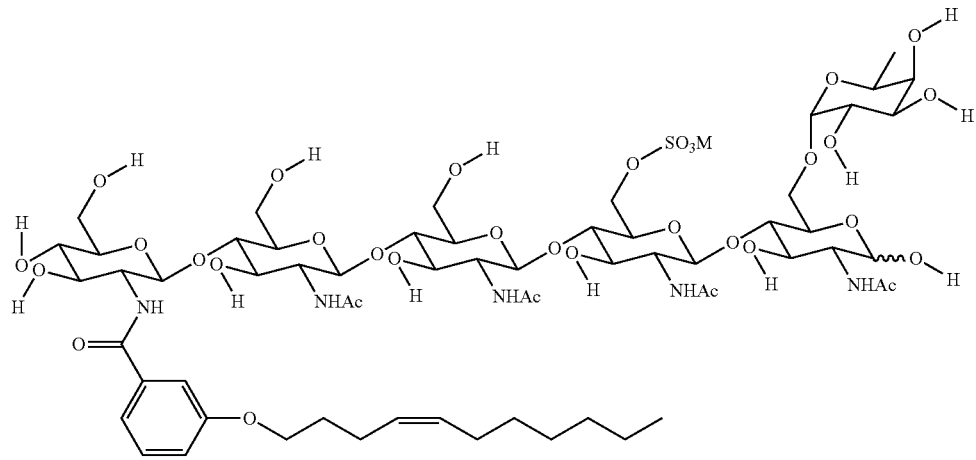
(XXI)
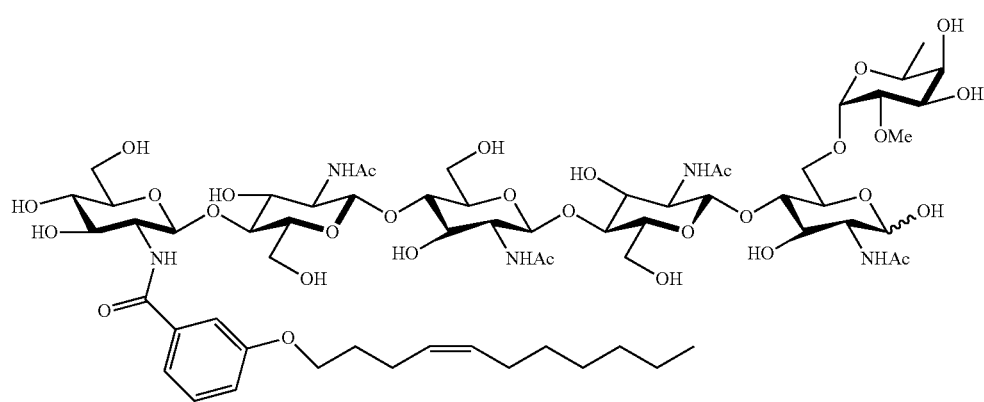
(XXII)
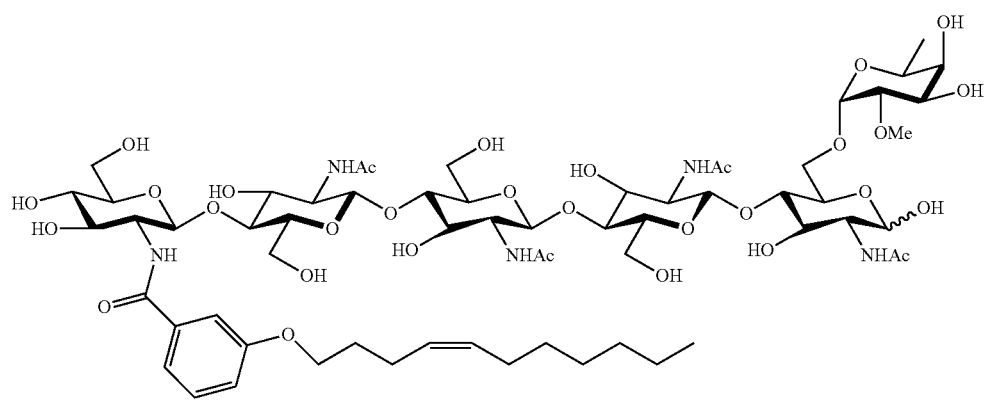
(XXIII)

-continued
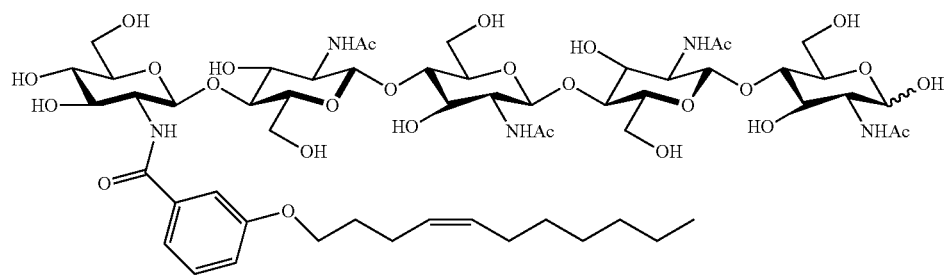
(XXIV)
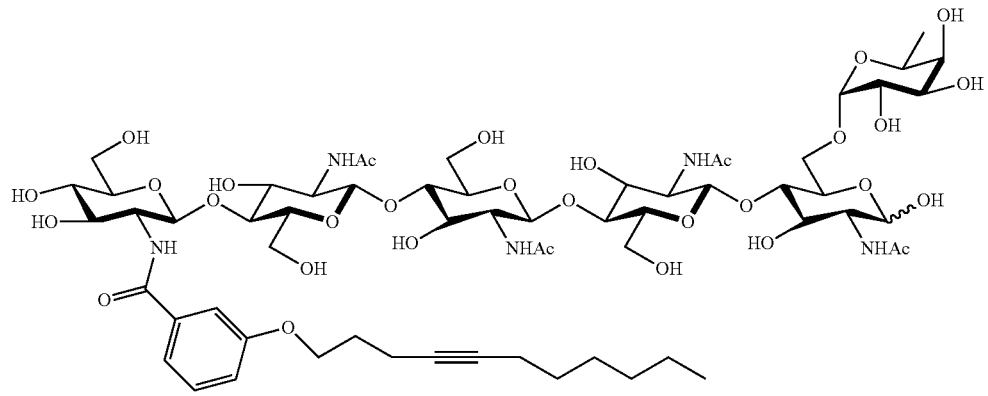
(XXV)
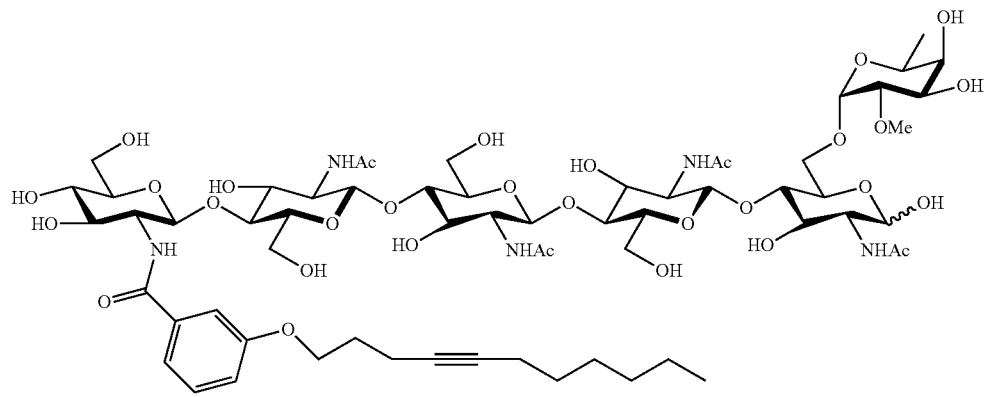
(XXVI)
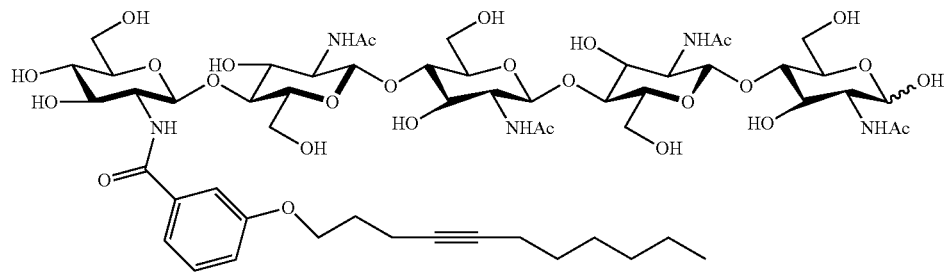
(XXVII)
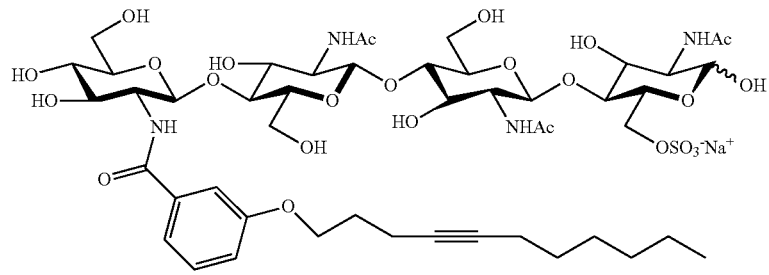
(XXVIII)

-continued
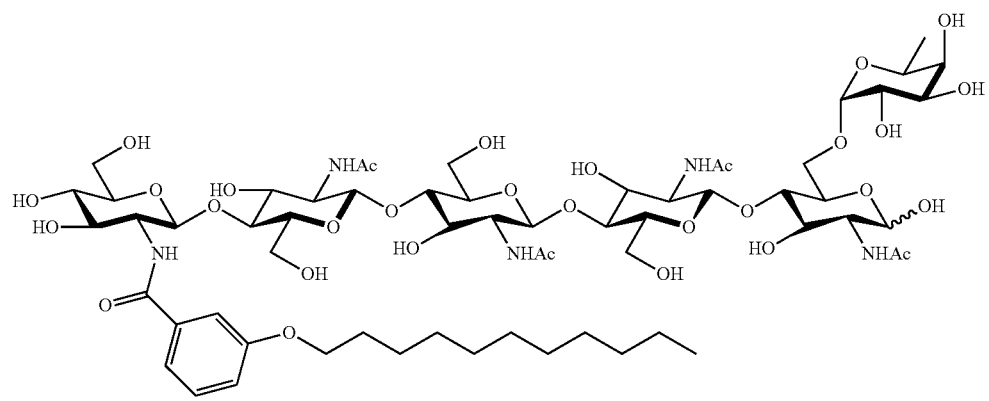
(XXIX)
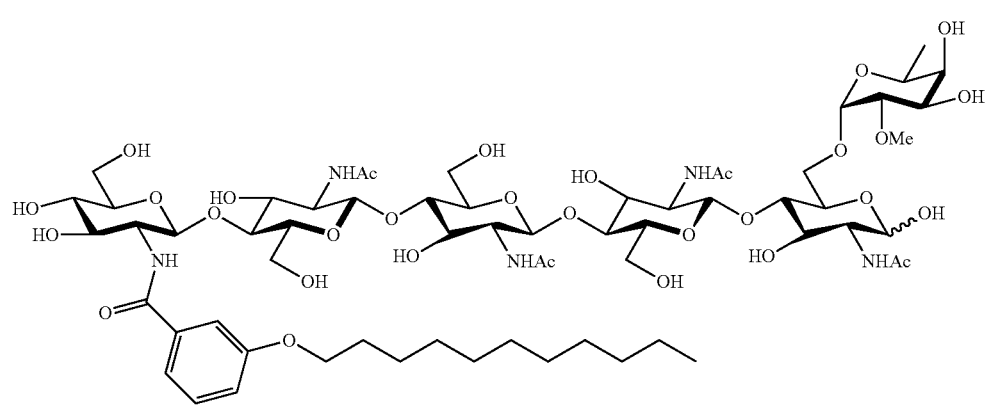
(XXX)
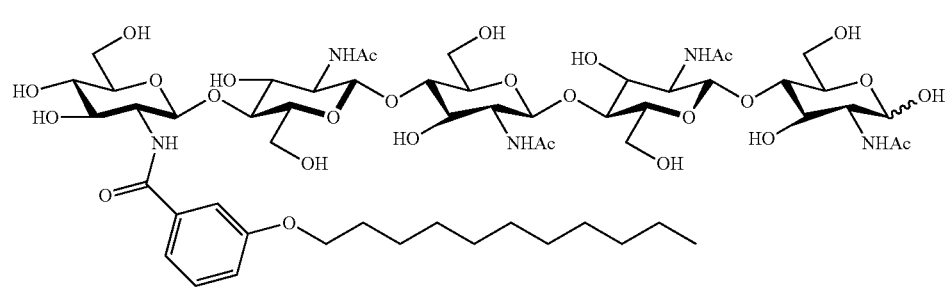
(XXXI)
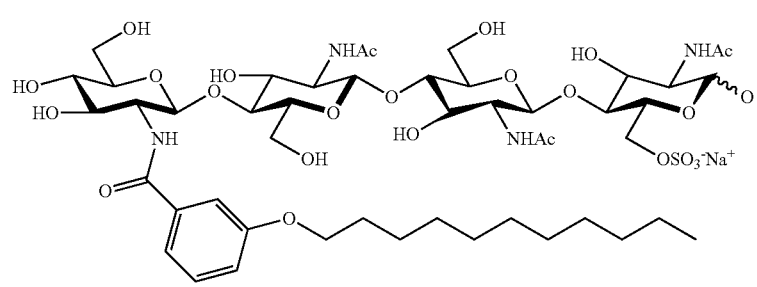
(XXXII)
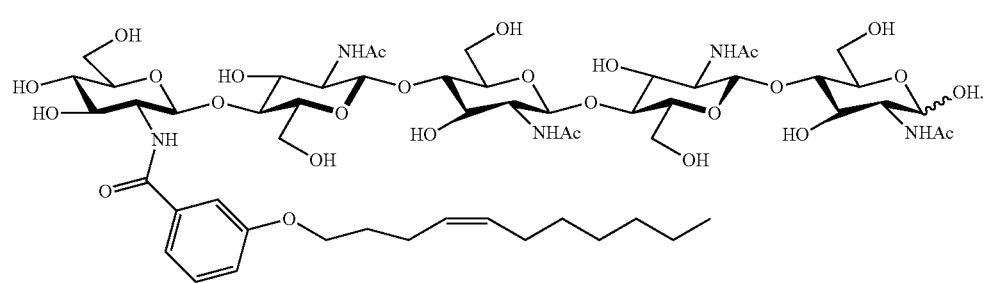
(XXXIII)

LCOs may be obtained from any suitable source. In some embodiments, the LCO is obtained (i.e., isolated and/or purified) from a bacterial strain. For example, in some embodiments, inoculant compositions of the present disclosure comprise one or more LCOs obtained from a of *Azorhizobium, Bradyrhizobium* (e.g., *B. japonicum*), *Mesorhizobium, Rhizobium* (e.g., *R. leguminosarum*), or *Sinorhizobium* (e.g., *S. meliloti*). In some embodiments, the LCO is obtained (i.e., isolated and/or purified) from a mycorrhizal fungus. For example, in some embodiments, inoculant compositions of the present disclosure comprise one or more LCOs obtained from a strain of Glomerocycota (e.g., *Glomus intraradicus*). See, e.g., WO 2010/049751 (in which the LCOs are referred to as "Myc factors"). In some embodiments, the LCO is synthetic. For example, in some embodiments, inoculant compositions of the present disclosure comprise one or more of the synthetic LCOs described in WO 2005/063784, WO 2007/117500 and/or WO 2008/071674. In some embodiments, the synthetic LCO contains one or more modifications or substitutions, such as those described in Spaink, CRIT. REV. PLANT SCI. 54:257 (2000) and D'Haeze, supra. LCOs and precursors for the construction of LCOs (e.g., COs, which are themselves useful as plant signal molecules) may be synthesized by genetically engineered organisms. See, e.g., Samain et al., CARBOHYDRATE RES. 302:35 (1997); Cottaz, et al., METH. ENG. 7(4):311 (2005); and Samain, et al., J. BIO- TECHNOL. 72:33 (1999) (e.g., FIG. 1 therein, which shows structures of COs that can be made recombinantly in *E. coli* harboring different combinations of genes nodBCHL).

It is to be understood that compositions and methods of the present disclosure may comprise analogues, derivatives, hydrates, isomers, salts and/or solvates of LCOs. Thus, in some embodiments, inoculant compositions of the present disclosure comprise one, two, three, four, five, six, seven, eight, nine, ten, or more LCOs represented by one or more of formulas I-IV and/or structures V-XXXIII and/or one, two, three, four, five, six, seven, eight, nine, ten, or more analogues, derivatives, hydrates, isomers, salts and/or solvates of LCOs represented by one or more of formulas I-IV and/or structures V-XXXIII.

LCOs (and derivatives thereof) may be utilized in various forms of purity and may be used alone or in the form of a culture of LCO-producing bacteria or fungi. In some embodiments, the LCO(s) included in inoculant compositions of the present disclosure is/are at least 50%, 55%, 60%, 65%, 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable chitin oligomer(s) and/or chitosan oligomer(s). See, e.g., D'Haeze et al., GLYCOBOL. 12(6): 79R (2002); Demont-Caulet et al., PLANT PHYSIOL. 120 (1):83 (1999); Hanel et al., PLANTA 232:787 (2010); Muller et al., PLANT PHYSIOL.124:733 (2000); Robma et al., TETRAHEDRON 58:521-530 (2002); Rouge et al., Docking of Chitin Oligomers and Nod Factors on Lectin Domains of the LysM-RLK Receptors in the *Medicago-Rhizobium* Symbiosis, in THE MOLECULAR IMMUNOLOGY OF COMPLEX CARBOHYDRATES-3 (Springer Science, 2011); Van der Holst et al., CURR. OPIN. STRUC. BIOL. 11:608 (2001); Wan et al., PLANT CELL 21:1053 (2009); and PCT/F100/00803 (2000).

In some embodiments, inoculant compositions of the present disclosure comprise one or more chitin oligosaccharides represented by formula XXXIV:

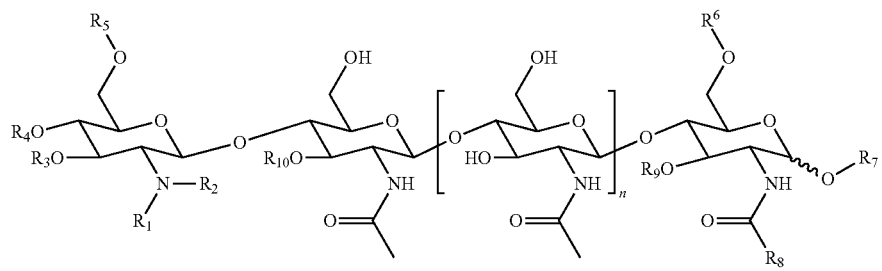

(XXXIV)

in which $R_1$ represents hydrogen or methyl; $R_2$ represents hydrogen or methyl; $R_3$ represents hydrogen, acetyl or carbamoyl; $R_4$ represents hydrogen, acetyl or carbamoyl; $R_5$ represents hydrogen, acetyl or carbamoyl; $R_6$ represents hydrogen, arabinosyl, fucosyl, acetyl, sulfate ester, 3-O—S-2-O-MeFuc, 2-O-MeFuc and 4-O-AcFuc; $R_7$ represents hydrogen, mannosyl or glycerol; $R_8$ represents hydrogen, methyl, or —CH$_2$OH; $R_9$ represents hydrogen, arabinosyl, or fucosyl; $R_{10}$ represents hydrogen, acetyl or fucosyl; and n represents 0, 1, 2 or 3.

In some embodiments, inoculant compositions of the present disclosure comprise one or more chitin oligosaccharides represented by formula XXXV:

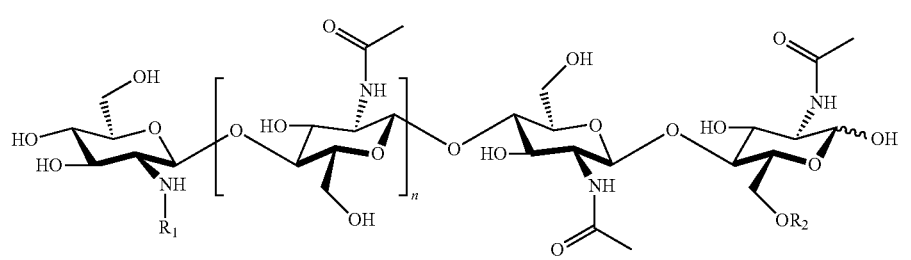
(XXXV)
in which n=1 or 2; $R_1$ represents hydrogen or methyl; and $R_2$ represents hydrogen or $SO_3H$.
Further examples of oligosaccharides (and derivatives thereof) that may be useful in compositions and methods of the present disclosure are provided below as structures XXXVI-LXXXIII:
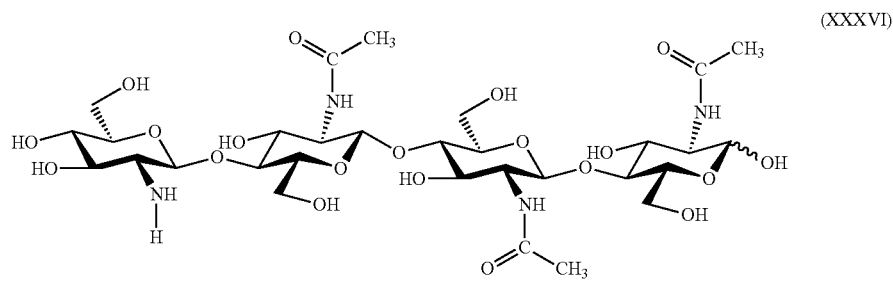
(XXXVI)
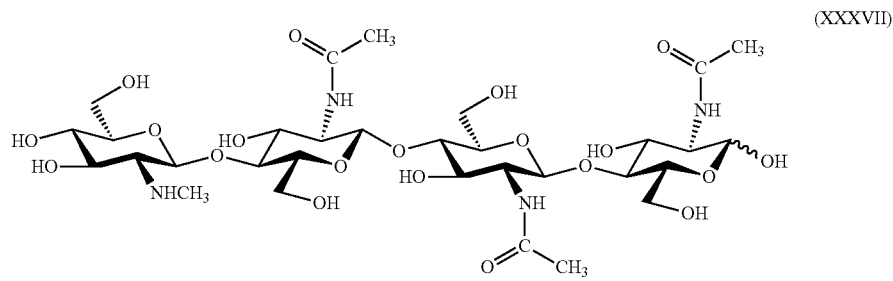
(XXXVII)
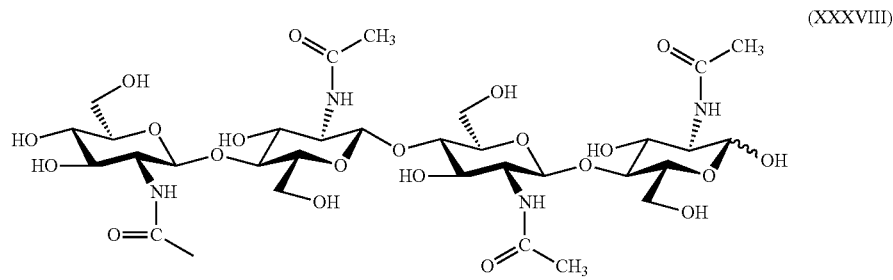
(XXXVIII)
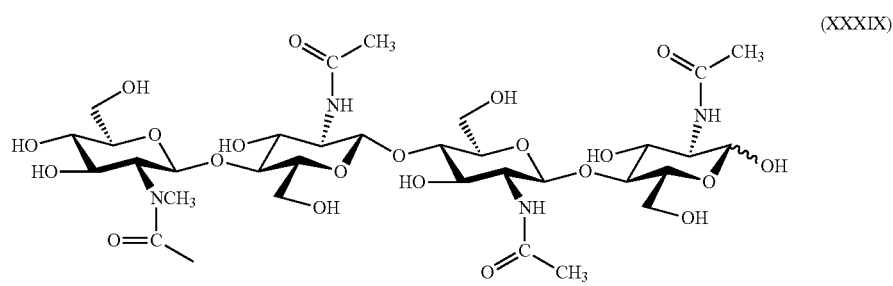
(XXXIX)

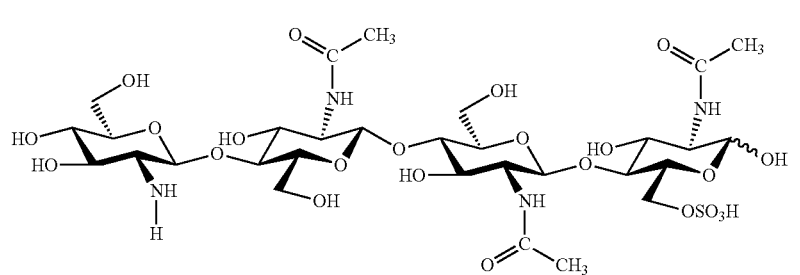
(XXXX)
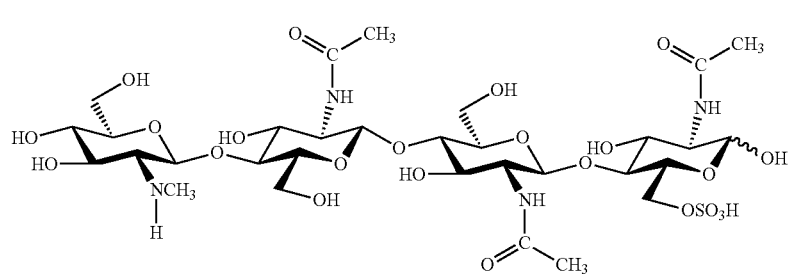
(XXXXI)
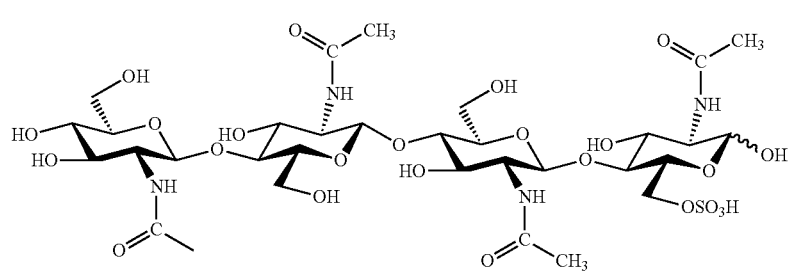
(XXXXII)
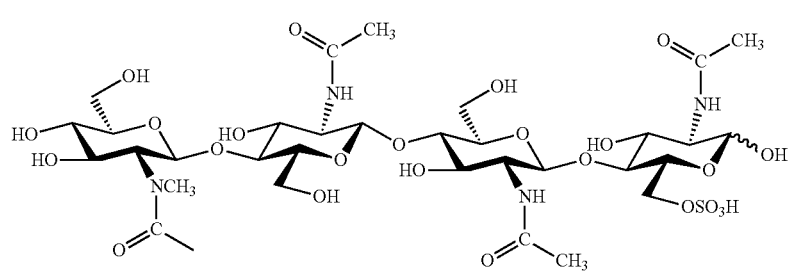
(XXXXIII)
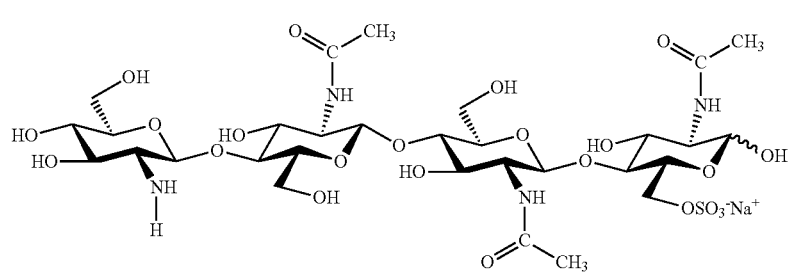
(XXXXIV)
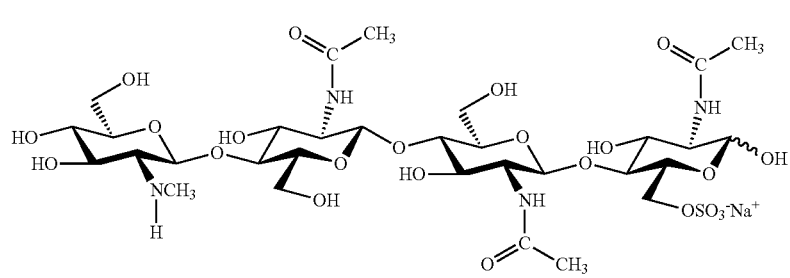
(XXXXV)

-continued
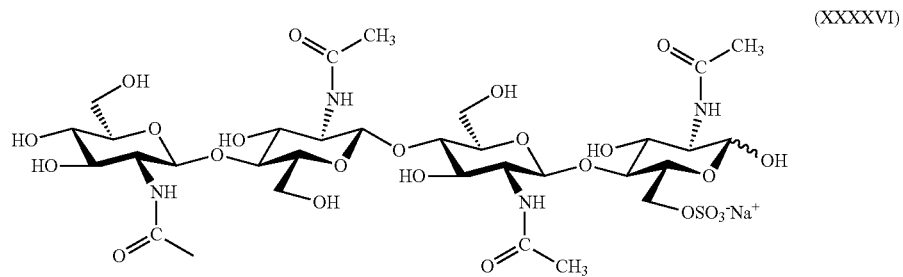
(XXXXVI)
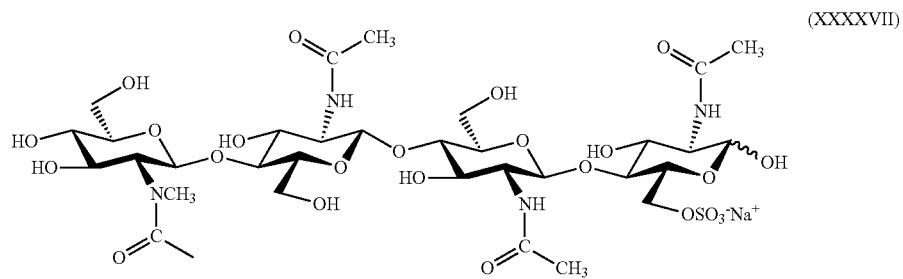
(XXXXVII)
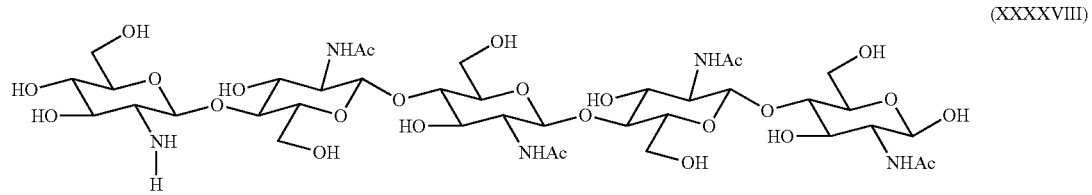
(XXXXVIII)
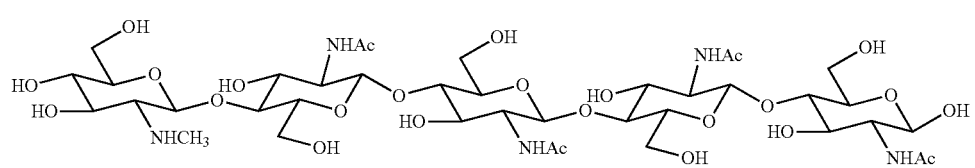
(XXXXIX)
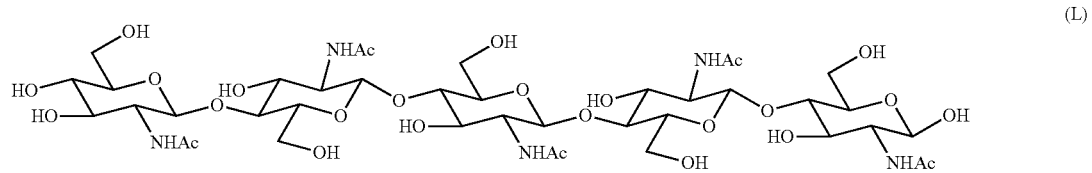
(L)
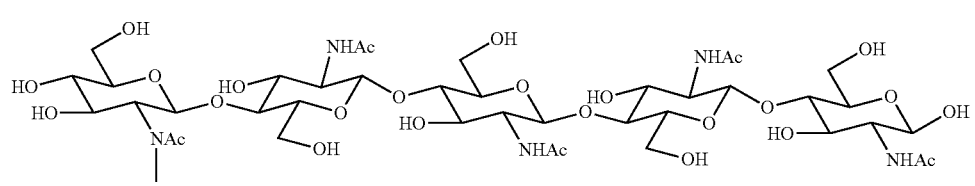
(LI)
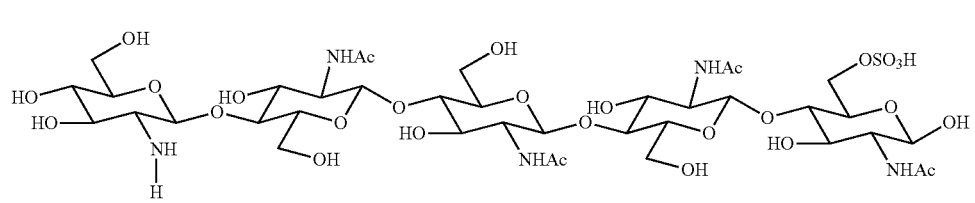
(LII)
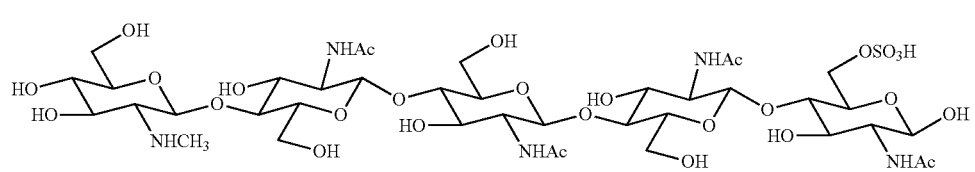
(LIII)

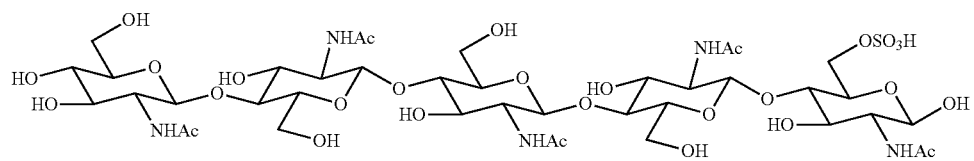 (LIV)
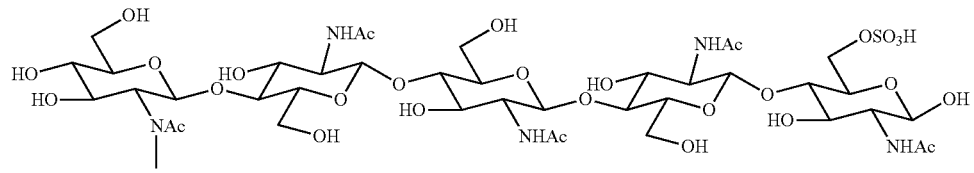 (LV)
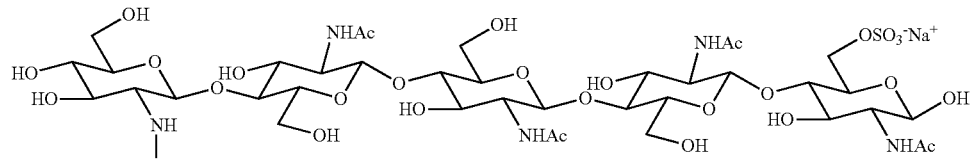 (LVI)
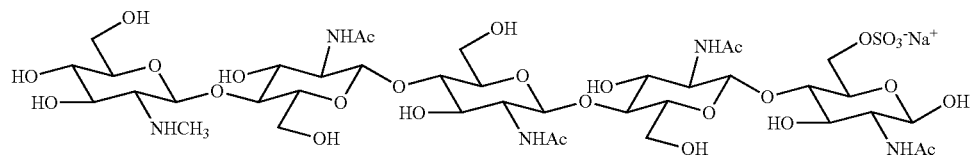 (LVII)
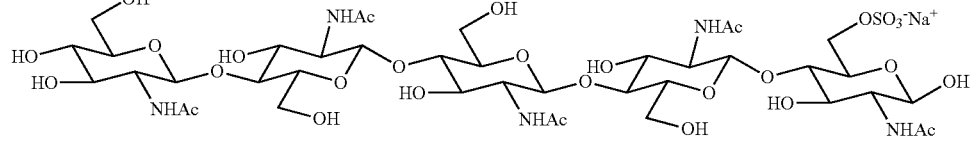 (LVIII)
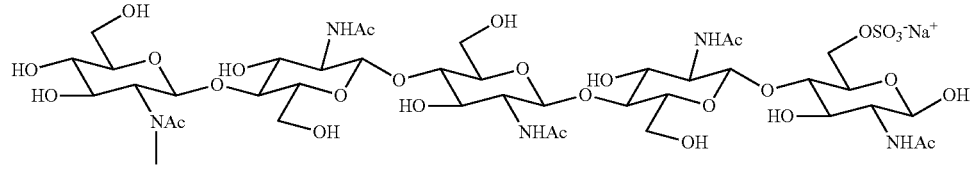 (LIX)
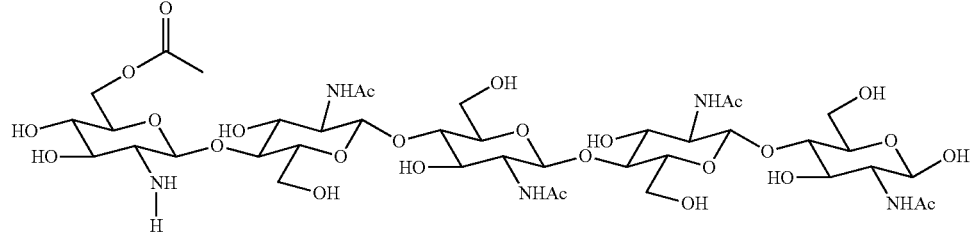 (LX)
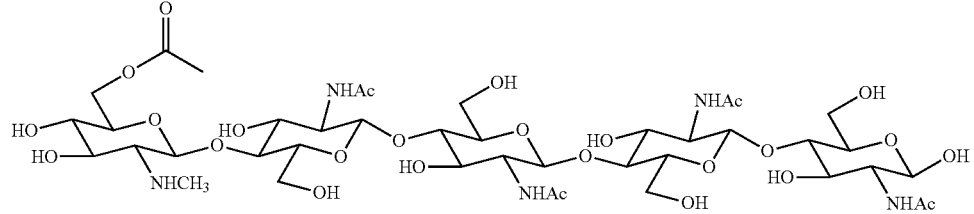 (LXI)

-continued
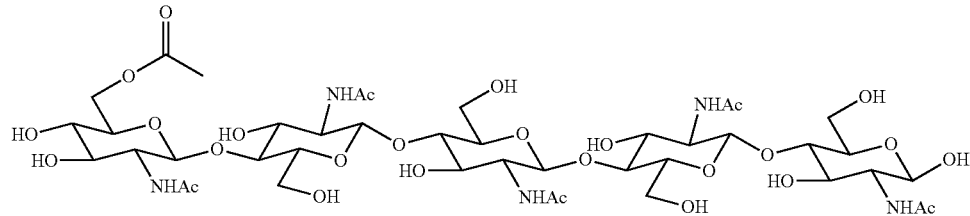
(LXII)
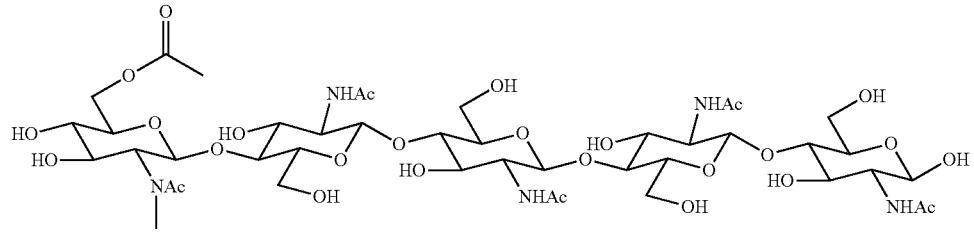
(LXIII)
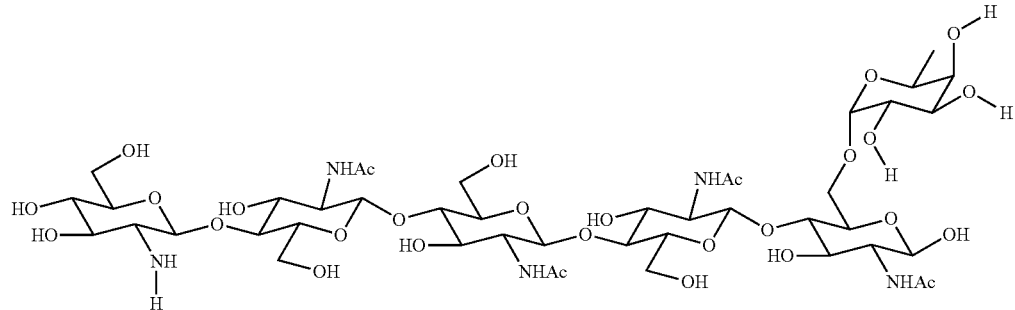
(LXIV)
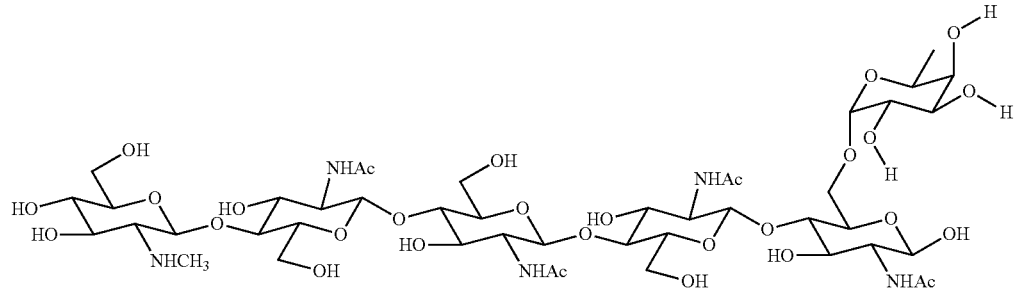
(LXV)
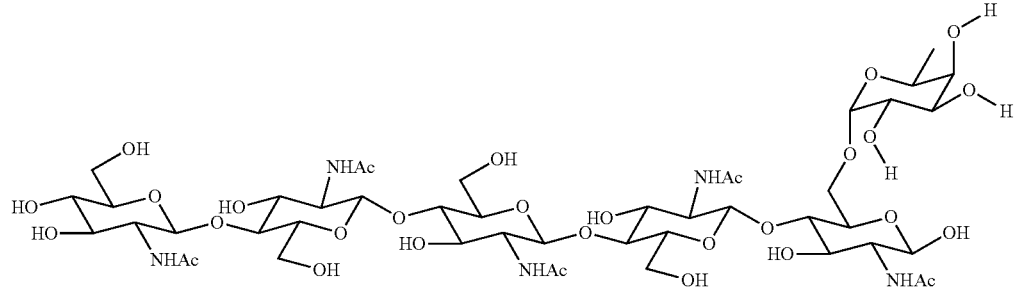
(LXVI)

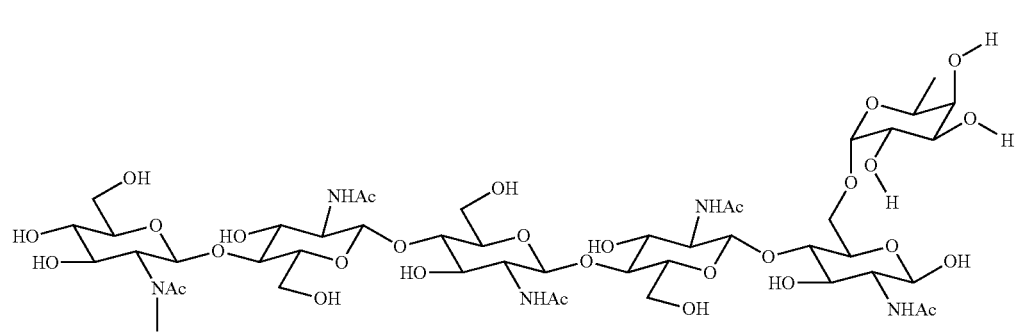
(LXVII)
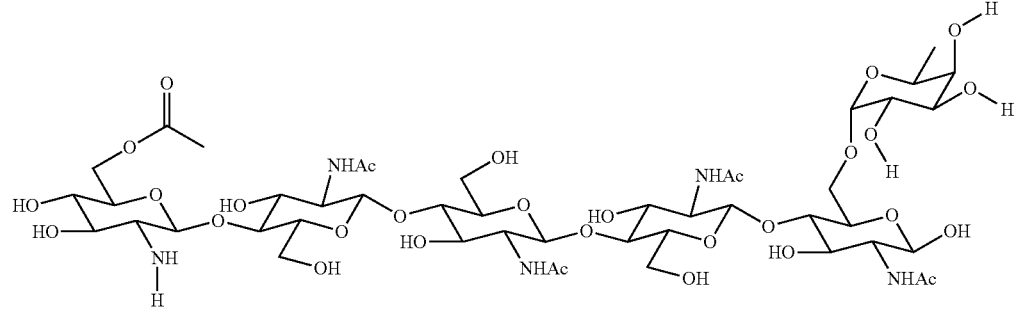
(LXVIII)
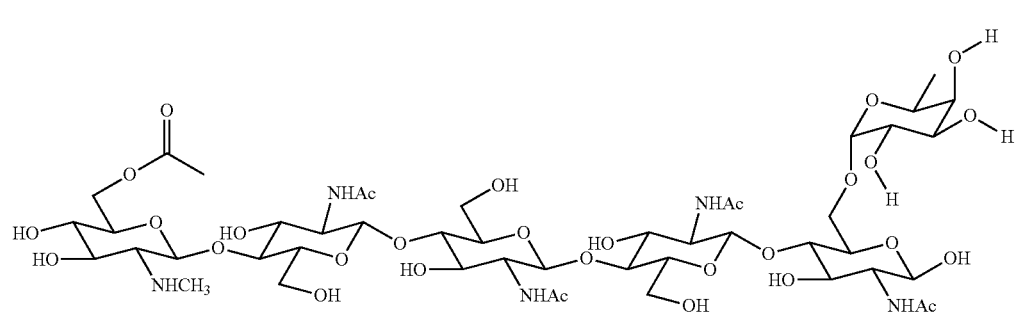
(LXIX)
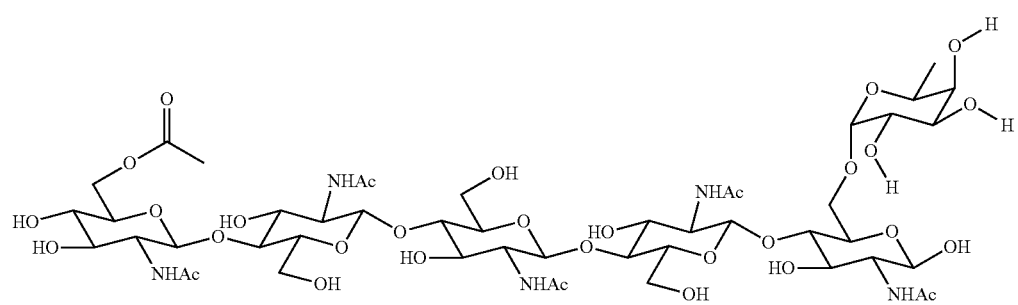
(LXX)
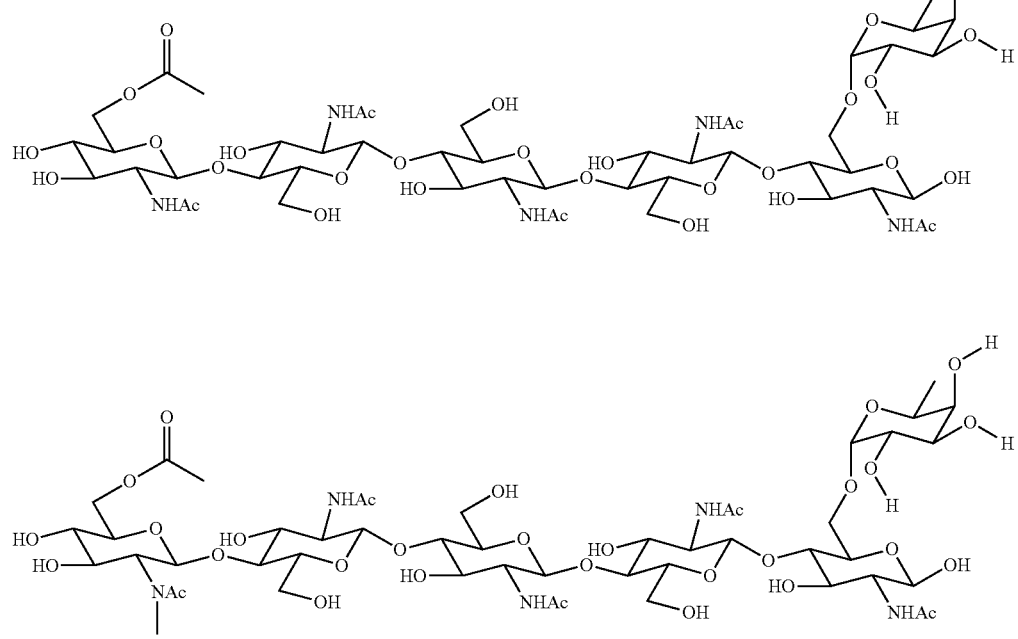
(LXXI)

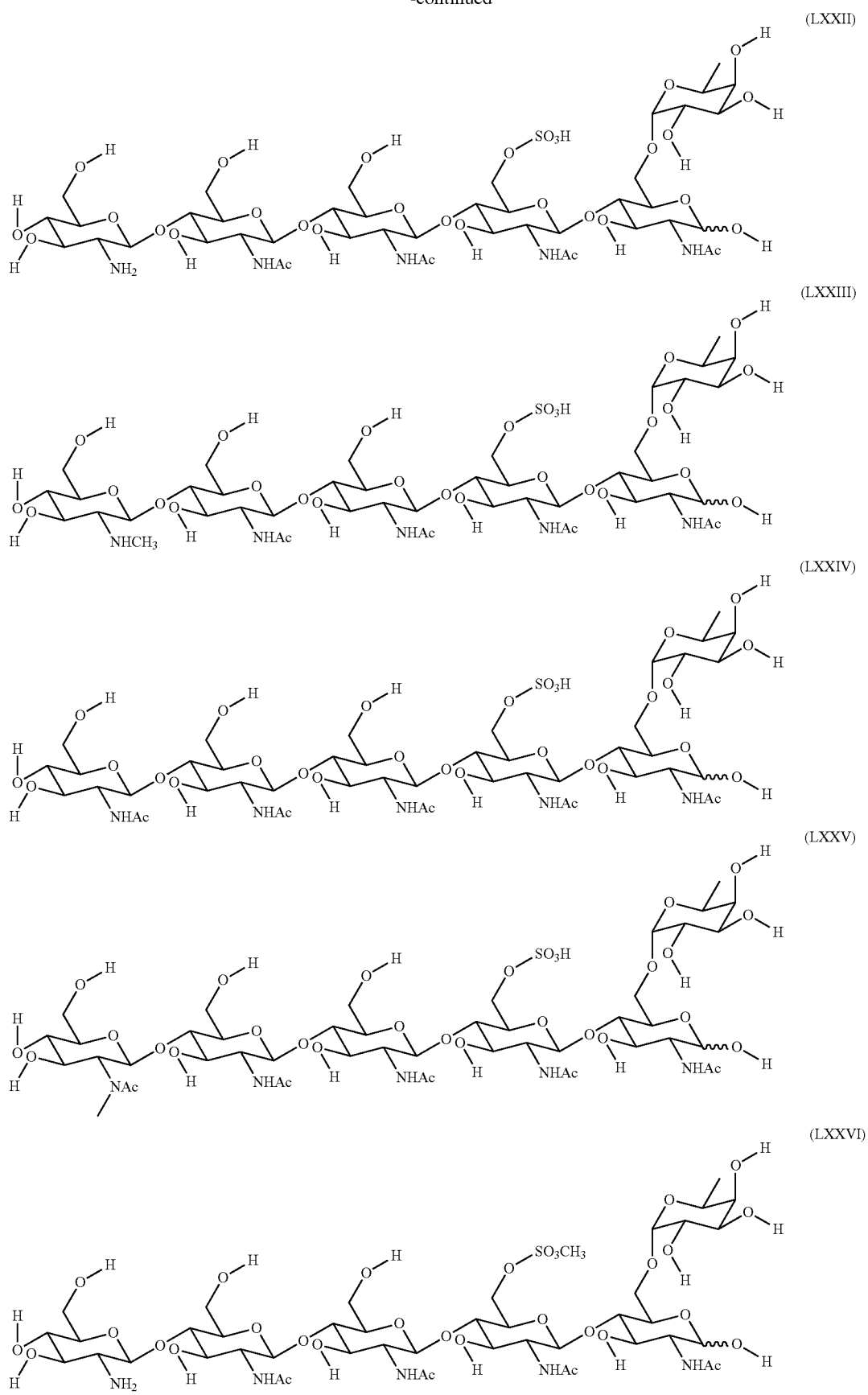

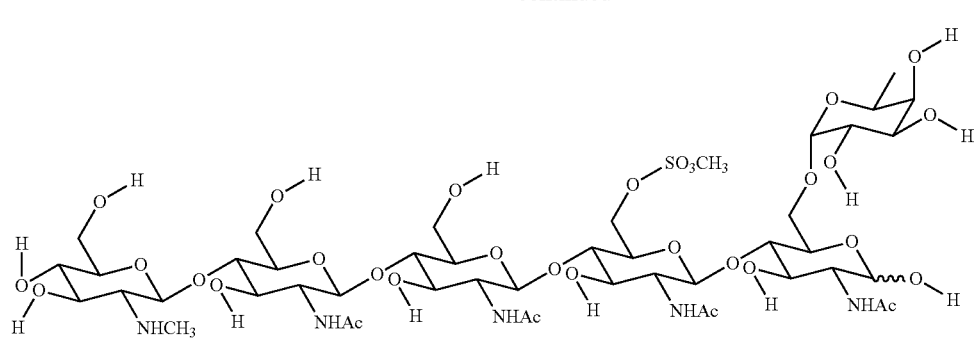
(LXXVII)
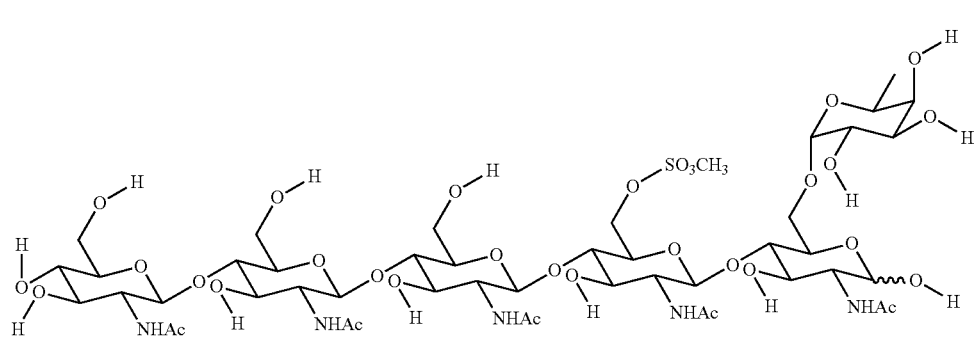
(LXXVIII)
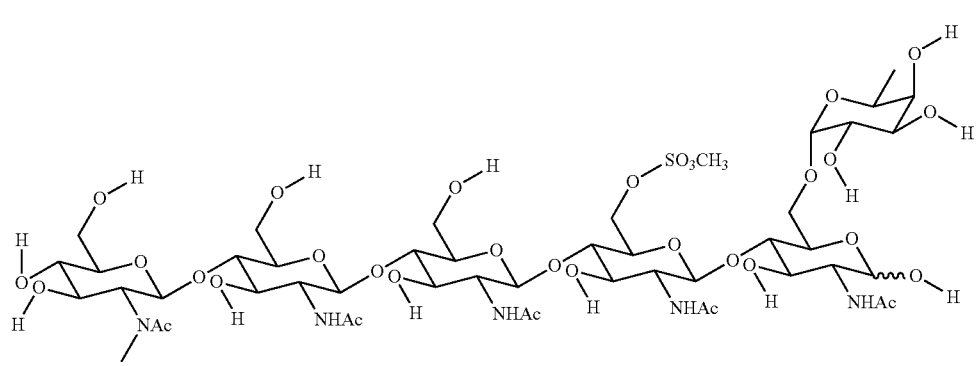
(LXXIX)
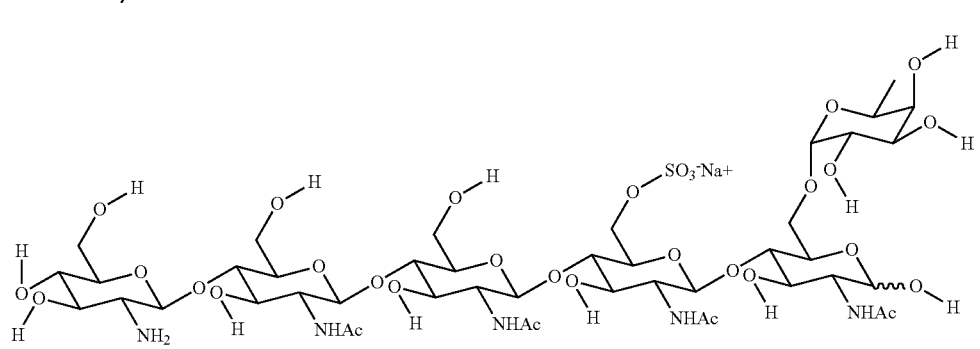
(LXXX)
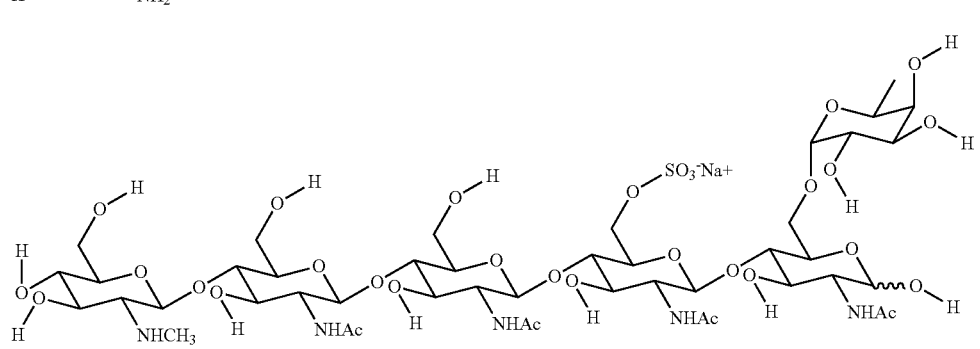
(LXXXI)

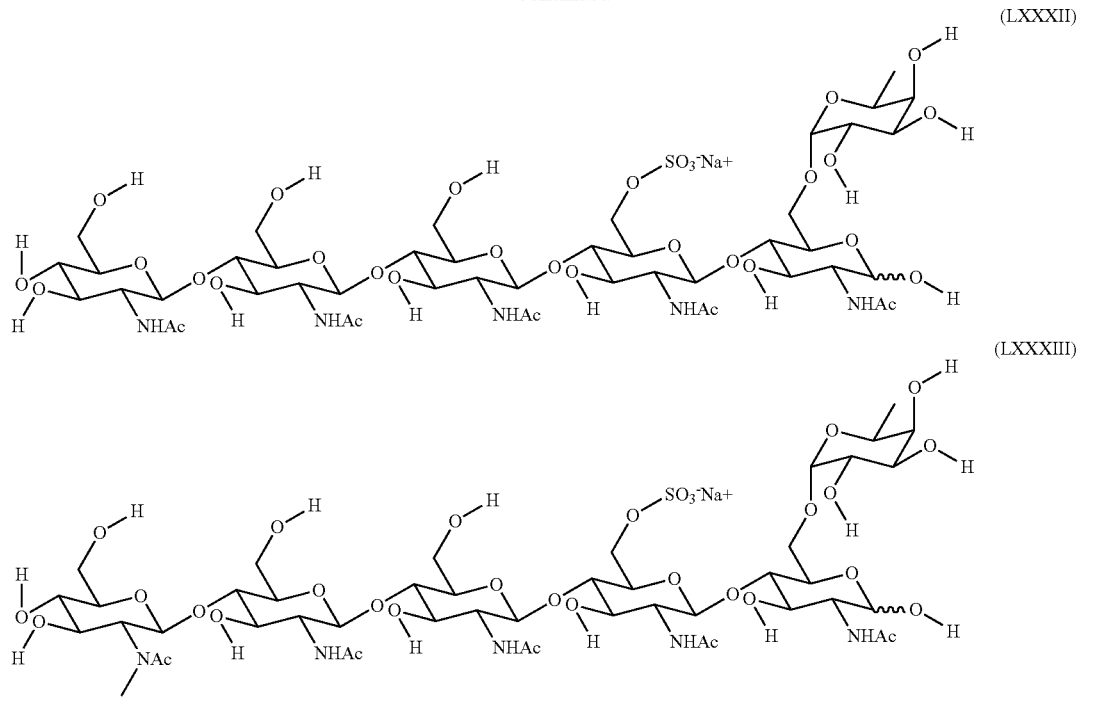

In some embodiments, inoculant compositions of the present disclosure comprise one or more of the oligosaccharides set forth above as structures XXXVI-LXXXIII in a deacetylated form (e.g., an oligosaccharide corresponding to structure XXXVI above except that one or more of the acetyl groups has been removed, optionally replaced by a hydrogen or methyl group).

Chitin oligosaccharides and chitosan oligosaccharides may be obtained from any suitable source. Chitin oligosaccharides and chitosan oligosaccharides may be harvested from chitin/chitosan (see, e.g., Aam et al., MAR. DRUGS 8:1482 (2010); D'Haeze et al., GLYCOBIOL. 12(6):79R (2002); Demont-Caulet et al., PLANT PHYSIOL. 120(1):83 (1999); Hanel et al., PLANTA 232:787 (2010); Limpanavech et al., SCIENTIA HORTICULTURAE 116:65 (2008); Lodhi et al., BIOMED RES. INTL. Vol. 2014 Art. 654913 (March 2014); Mourya et al., POLYMER SCI. 53(7):583 (2011); Muller et al., PLANT PHYSIOL.124:733 (2000); Robina et al., TETRAHEDRON 58:521 (2002); Rouge et al., The Molecular Immunology of Complex Carbohydrates, in ADVANCES IN EXPERIMENTAL MEDICINE AND BIOLOGY (Springer Science, 2011); Van der Holst et al., CURR. OPIN. STRUC. BIOL. 11:608 (2001); Wan et al., PLANT CELL 21:1053 (2009); Xia et al., FOOD HYDROCOLLOIDS 25:170 (2011); PCT/F100/00803 (2000)). They may also be synthetically generated (see, e.g., Cottaz et al., METH. ENG. 7(4):311 (2005); Samain et al., CARBOHYDRATE RES. 302:35 (1997); Samain et al., J. BIOTECHNOL. 72:33 (1999)). In some embodiments, they are derived from a naturally occurring LCO. For example, in some embodiments, inoculant compositions of the present disclosure comprise one or more chitin/chitosan oligosaccharides derived from an LCO obtained (i.e., isolated and/or purified) from a strain of Azorhizobium, Bradyrhizobium (e.g., B. japonicum), Mesorhizobium, Rhizobium (e.g., R. leguminosarum), Sinorhizobium (e.g., S. meliloti), or mycorhizzal fungus (e.g., Glomus intraradicus). In some embodiments, inoculant compositions of the present disclosure comprise one or more chitin oligosaccharides and/or chitosan oligosaccharides derived from an LCO obtained (i.e., isolated and/or purified) from a strain of Azorhizobium, Bradyrhizobium (e.g., B. japonicum), Mesorhizobium, Rhizobium (e.g., R. leguminosarum), Sinorhizobium (e.g., S. meliloti), or mycorhizzal fungus (e.g., Glomus intraradicus). In some embodiments, the chitin oligosaccharide(s) and/or chitosan oligosaccharide(s) is/are derived from an LCO represented by one or more of formulas I-IV and/or structures V-XXXIII. Thus, in some embodiments, inoculant compositions of the present disclosure may comprise one or more chitin oligosaccharides represented by one or more of formulas I-IV and/or structures V-XXXIII except that the pendant fatty acid is replaced with a hydrogen or methyl group.

It is to be understood that compositions of the present disclosure may comprise analogues, derivatives, hydrates, isomers, salts and/or solvates of chitin oligosaccharides and/or chitosan oligosaccharides. Thus, in some embodiments, inoculant compositions of the present disclosure comprise one, two, three, four, five, six, seven, eight, nine, ten, or more chitin oligosaccharides represented by one or more of formulas XXXIV-XXXV and/or structures XXXVI-LXXXIII and/or one, two, three, four, five, six, seven, eight, nine, ten, or more analogues, derivatives, hydrates, isomers, salts and/or solvates of chitin oligosaccharides represented by one or more of formulas XXXIV-XXXV and/or structures XXXVI-LXXXIII.

Chitin oligosaccharides and chitosan oligosaccharides (and analogues, derivatives, hydrates, isomers, salts and/or solvates thereof) may be utilized in various forms of purity and may be used alone or in the form of a culture of CO-producing bacteria or fungi. In some embodiments, the chitin oligosaccharides and/or chitosan oligosaccharides included in inoculant compositions of the present disclosure is/are at least 50%, 55%, 60%, 65%, 70%, 75%, 80%, 85%, 90%, 91%, 92%, 93%, 94%, 95%, 96%, 97%, 98%, 99%, 99.5% or more pure.

Inoculant compositions of the present disclosure may comprise any suitable chitinous compound(s), including, but not limited to, chitin (IUPAC: N-[5-[[3-acetylamino-4,5-dihydroxy-6-(hydroxymethyl)oxan-2yl]methoxymethyl]-2-[[5-acetylamino-4, 6-dihydroxy-2-(hydroxymethyl)oxan-3-yl]methoxymethyl]-4-hydroxy-6-(hydroxymethyl)oxan-3-ys]ethanamide), chitosan(IUPAC: 5-amino-6-[5-amino-6-[5-amino-4,6-dihydroxy-2(hydroxymethyl)oxan-3-yl]oxy-4-hydroxy-2-(hydroxymethyl)oxan-3-yl]oxy-2 (hydroxymethyl)oxane-3,4-diol) and isomers, salts and solvates thereof.

Chitins and chitosans may be obtained commercially or prepared from insects, crustacean shells, or fungal cell walls. Methods for the preparation of chitin and chitosan are known in the art. See, e.g., U.S. Pat. No. 4,536,207 (preparation from crustacean shells) and 5,965,545 (preparation from crab shells and hydrolysis of commercial chitosan); Pochanavanich, et al., LETT. APPL. MICROBIOL. 35:17 (2002) (preparation from fungal cell walls).

Chitin and chitosan compositions formulated for seed treatment are commercially available. Commercial products include, for example, ELEXA® (Plant Defense Boosters, Inc.) and BEYOND™ (Agrihouse, Inc.).

Inoculant compositions of the present disclosure may comprise any suitable flavonoid(s), including, but not limited to, anthocyanidins, anthoxanthins, chalcones, coumarins, flavanones, flavanonols, flavans and isoflavonoids, as well as analogues, derivatives, hydrates, isomers, polymers, salts and solvates thereof.

Flavonoids are phenolic compounds having the general structure of two aromatic rings connected by a three-carbon bridge. Classes of flavonoids include are known in the art. See, e.g., Jain et al., J. PLANT BIOCHEM. & BIOTECHNOL. 11:1 (2002); Shaw et al., ENVIRON. MICROBIOL. 11:1867 (2006). Flavonoid compounds are commercially available, e.g., from Novozymes BioAg, Saskatoon, Canada; Natland International Corp., Research Triangle Park, NC; MP Biomedicals, Irvine, CA; LC Laboratories, Woburn MA. Flavonoid compounds may be isolated from plants or seeds, e.g., as described in U.S. Pat. Nos. 5,702,752; 5,990,291; and 6,146,668. Flavonoid compounds may also be produced by genetically engineered organisms, such as yeast, as described in Ralston et al., PLANT PHYSIOL. 137:1375 (2005).

In some embodiments, inoculant compositions of the present disclosure comprise one or more anthocyanidins. According to some embodiments, the inoculant composition comprises cyanidin, delphinidin, malvidin, pelargonidin, peonidin and/or petunidin.

In some embodiments, inoculant compositions of the present disclosure comprise one or more anthoxanthins. According to some embodiments, the inoculant composition comprises one or more flavones (e.g., apigenin, baicalein, chrysin, 7,8-dihydroxyflavone, diosmin, flavoxate, 6-hydroxyflavone, luteolin, scutellarein, tangeritin and/or wogonin) and/or flavonols (e.g., amurensin, astragalin, azaleatin, azalein, fisetin, furanoflavonols galangin, gossypetin, 3-hydroxyflavone, hyperoside, icariin, isoquercetin, kaempferide, kaempferitrin, kaempferol, isorhamnetin, morin, myricetin, myricitrin, natsudaidain, pachypodol, pyranoflavonols quercetin, quericitin, rhamnazin, rhamnetin, robinin, rutin, spiraeoside, troxerutin and/or zanthorhamnin).

In some embodiments, inoculant compositions of the present disclosure comprise one or more flavanones.

According to some embodiments, the inoculant composition comprises butin, eriodictyol, hesperetin, hesperidin, homo-eriodictyol, isosakuranetin, naringenin, naringin, pinocembrin, poncirin, sakuranetin, sakuranin and/or sterubin.

In some embodiments, inoculant compositions of the present disclosure comprise one or more flavanonols. According to some embodiments, the inoculant composition comprises dihydrokaempferol and/or taxifolin.

In some embodiments, inoculant compositions of the present disclosure comprise one or more flavans. According to some embodiments, the inoculant composition comprises one or more flavan-3-ols (e.g., catechin (C), catechin 3-gallate (Cg), epicatechins (EC), epigallocatechin (EGC) epicatechin 3-gallate (ECg), epigallcatechin 3-gallate (EGCg), epiafzelechin, fisetinidol, gallocatechin (GC), gallcatechin 3-gallate (GCg), guibourtinidol, mesquitol, robinetinidol, theaflavin-3-gallate, theaflavin-3'-gallate, theflavin-3,3'-digallate, thearubigin), flavan-4-ols (e.g., apiforol and/or luteoforol) and/or flavan-3,4-diols (e.g., leucocyanidin, leucodelphinidin, leucofisetinidin, leucomalvidin, leucopelargonidin, leucopeonidin, leucorobinetinidin, melacacidin and/or teracacidin) and/or dimers, trimers, oligomers and/or polymers thereof (e.g., one or more proanthocyanidins).

In some embodiments, inoculant compositions of the present disclosure comprise one or more isoflavonoids. According to some embodiments, the inoculant composition comprises one or more isoflavones (e.g, biochanin A, daidzein, formononetin, genistein and/or glycitein), isoflavanes (e.g., equol, ionchocarpane and/or laxifloorane), isoflavandiols, isoflavenes (e.g., glabrene, haginin D and/or 2-methoxyjudaicin), coumestans (e.g., coumestrol, plicadin and/or wedelolactone), pterocarpans and/or roteonoids.

Inoculant compositions of the present disclosure may comprise any suitable flavonoid derivative, including, but not limited to, neoflavonoids (e.g, calophyllolide, coutareagenin, dalbergichromene, dalbergin, nivetin) and pterocarpans (e.g., bitucarpin A, bitucarpin B, erybraedin A, erybraedin B, erythrabyssin II, erthyrabissin-1, erycristagallin, glycinol, glyceollidins, glyceollins, glycyrrhizol, maackiain, medicarpin, morisianine, orientanol, phaseolin, pisatin, striatine, trifolirhizin).

Flavonoids and derivatives thereof may be incorporated into inoculant compositions of the present disclosure in any suitable form, including, but not limited to, polymorphic and crystalline forms.

Inoculant compositions of the present disclosure may comprise any suitable non-flavonoid nod-gene inducer(s), including, but not limited to, jasmonic acid ([IR-[1a,2p(Z)]]-3-oxo-2-(pentenyl)cyclopentaneacetic acid; JA), linoleic acid ((Z,Z)-9,12-octadecadienoic acid) and linolenic acid ((Z,Z,Z)-9,12,15-octadecatrienoic acid), as well as analogues, derivatives, hydrates, isomers, polymers, salts and solvates thereof.

Jasmonic acid and its methyl ester, methyl jasmonate (MeJA), collectively known as jasmonates, are octadecanoid-based compounds that occur naturally in some plants (e.g., wheat), fungi (e.g., *Botryodiplodia theobromae*, Gibbrella fujikuroi), yeast (e.g., *Saccharomyces cerevisiae*) and bacteria (e.g., *Escherichia coli*). Linoleic acid and linolenic acid may be produced in the course of the biosynthesis of jasmonic acid. Jasmonates, linoleic acid and linolenic acid (and their derivatives) are reported to be inducers of nod gene expression or LCO production by rhizobacteria. See, e.g., Mabood, et al. PLANT PHYSIOL. BIOCHEM. 44(11): 759 (2006); Mabood et al., AGR. J. 98(2):289 (2006); Mabood, et al., FIELD CROPS RES.95(2-3):412 (2006); Mabood & Smith, Linoleic and linolenic acid induce the expression of nod genes in *Bradyrhizobium japonicum* USDA 3, PLANT BIOL. (2001). Non-limiting examples of derivatives of jasmonic acid, linoleic acid, linolenic acid include esters, amides, glycosides and salts. Representative esters are compounds in which the carboxyl group of linoleic acid, linolenic acid, or jasmonic acid has been replaced with a —COR group, where R is an —OR$^1$ group, in which R$^1$ is: an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_8$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Representative amides are compounds in which the carboxyl group of linoleic acid, linolenic acid, or jasmonic acid has been replaced with a —COR group, where R is an NR$^2$R$^3$ group, in which R$^2$ and R$^3$ are independently: hydrogen; an alkyl group, such as a $C_1$-$C_8$ unbranched or branched alkyl group, e.g., a methyl, ethyl or propyl group; an alkenyl group, such as a $C_2$-$C_8$ unbranched or branched alkenyl group; an alkynyl group, such as a $C_2$-$C_5$ unbranched or branched alkynyl group; an aryl group having, for example, 6 to 10 carbon atoms; or a heteroaryl group having, for example, 4 to 9 carbon atoms, wherein the heteroatoms in the heteroaryl group can be, for example, N, O, P, or S. Esters may be prepared by known methods, such as acid-catalyzed nucleophilic addition, wherein the carboxylic acid is reacted with an alcohol in the presence of a catalytic amount of a mineral acid. Amides may also be prepared by known methods, such as by reacting the carboxylic acid with the appropriate amine in the presence of a coupling agent such as dicyclohexyl carbodiimide (DCC), under neutral conditions. Suitable salts of linoleic acid, linolenic acid and jasmonic acid include e.g., base addition salts. The bases that may be used as reagents to prepare metabolically acceptable base salts of these compounds include those derived from cations such as alkali metal cations (e.g., potassium and sodium) and alkaline earth metal cations (e.g., calcium and magnesium). These salts may be readily prepared by mixing together a solution of linoleic acid, linolenic acid, or jasmonic acid with a solution of the base. The salts may be precipitated from solution and be collected by filtration or may be recovered by other means such as by evaporation of the solvent.

Inoculant compositions of the present disclosure may comprise any suitable karrakin(s), including, but not limited to, 2H-furo[2,3-c]pyran-2-ones, as well as analogues, derivatives, hydrates, isomers, polymers, salts and solvates thereof.

In some embodiments, the inoculant composition comprises one or more karrakins represented by formula LXXXIV:

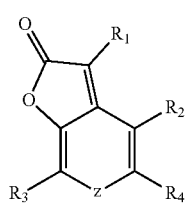

(LXXXIV)

in which Z is O, S or NR$_5$; R$_1$, R$_2$, R$_3$ and R$_4$ are each independently H, alkyl, alkenyl, alkynyl, phenyl, benzyl, hydroxy, hydroxyalkyl, alkoxy, phenyloxy, benzyloxy, CN, COR$_6$, COOR=, halogen, NR$_6$R$_7$, or NO$_2$; and R$_5$, R$_6$ and R$_7$ are each independently H, alkyl or alkenyl, or a biologically acceptable salt thereof.

Examples of biologically acceptable salts of karrakins include acid addition salts formed with biologically acceptable acids, examples of which include hydrochloride, hydrobromide, sulphate or bisulphate, phosphate or hydrogen phosphate, acetate, benzoate, succinate, fumarate, maleate, lactate, citrate, tartrate, gluconate; methanesulphonate, benzenesulphonate and p-toluenesulphonic acid. Additional biologically acceptable metal salts may include alkali metal salts, with bases, examples of which include the sodium and potassium salts. Examples of compounds embraced by formula XXXX and which may be suitable for use in the present disclosure include 3-methyl-2H-furo[2,3-c]pyran-2-one (where R$_1$=CH$_3$, R$_2$, R$_3$, R$_4$=H), 2H-furo[2,3-c]pyran-2-one (where R$_1$, R$_2$, R$_3$, R$_4$=H), 7-methyl-2H-furo[2,3-c]pyran-2-one (where R$_1$, R$_2$, R$_4$=H, R$_3$=CH$_3$), 5-methyl-2H-furo[2,3-c]pyran-2-one (where R$_1$, R$_2$, R$_3$=H, R$_4$=CH$_3$), 3,7-dimethyl-2H-furo[2,3-c]pyran-2-one (where R$_1$, R$_3$=CH$_3$, R$_2$, R$_4$=H), 3,5-dimethyl-2H-furo[2,3-c]pyran-2-one (where R$_1$, R$_4$=CH$_3$, R$_2$, R$_3$=H), 3,5,7-trimethyl-2H-furo[2,3-c]pyran-2-one (where R$_1$, R$_3$, R$_4$=CH$_3$, R$_2$=H), 5-methoxymethyl-3-methyl-2H-furo[2,3-c]pyran-2-one (where R$_1$=CH$_3$, R$_2$, R$_3$=H, R$_4$=CH$_2$OCH3), 4-bromo-3,7-dimethyl-2H-furo[2,3-c]pyran-2-one (where R$_1$, R$_3$=CH$_3$, R$_2$=Br, R$_4$=H), 3-methylfuro[2,3-c]pyridin-2(3H)-one (where Z=NH, R$_1$=CH$_3$, R$_2$, R$_3$, R$_4$=H) and 3,6-dimethylfuro[2,3-c]pyridin-2(6H)-one (where Z=N—CH$_3$, R$_1$=CH$_3$, R$_2$, R$_3$, R$_4$=H). See, e.g., U.S. Pat. No. 7,576,213; Halford, Smoke Signals, in CHEM. ENG. NEws (Apr. 12, 2010) (reporting that karrikins or butenolides contained in smoke act as growth stimulants and spur seed germination after a forest fire and can invigorate seeds such as com, tomatoes, lettuce and onions that had been stored).

Inoculant compositions of the present disclosure may comprise gluconolactone and/or one or more analogues, derivatives, hydrates, isomers, polymers, salts and/or solvates thereof.

Inoculant compositions of the present disclosure may comprise any suitable excipient(s), including, but not limited to, dispersants, drying agents, anti-freezing agents, seed flowability agents, safeners, anti-settlign agents, pH buffers and adhesives.

Inoculant compositions of the present disclosure may comprise any suitable agriculturally acceptable dispersant(s), including, but not limited to, surfactants and wetting agents. Selection of appropriate dispersants will depend on the intended application(s) and the microorganism(s) present in the inoculant composition. In general, the dispersant(s) will have low toxicity for the microorganism(s) in the inoculant composition and for the plant part(s) to which the inoculant composition is to be applied. In some embodiments, the dispersant(s) will be selected to wet and/or emulsify one or more soils. Non-limiting examples of dispersants include ATLOX™ (e.g., 4916, 4991; Croda International PLC, Edison, NJ), ATLOX METASPERSE™ (Croda International PLC, Edison, NJ), BIO-SOFT® (e.g., N series, such as N1-3, N1-7, N1-5, N1-9, N2-3-3, N2-3-6.5, N2-5-3, N2-5-7, N2-5-9, N91-2.5, N91-6, N91-8; Stepan Company, Northfield, IL), MAKON®nonionic surfactants (e.g., DA-4, DA-6 and DA-9; Stepan Company, Northfield, IL), MORWET® powders (Akzo Nobel Surface Chemistry LLC, Chicago, IL), MULTIWET™ surfactants (e.g., MO-85P-PW-(AP); Croda International PLC, Edison, NJ), SILWET® L-77 (Helena Chemical Company, Collierville, TN), SPAN™ surfactants (e.g., 20, 40, 60, 65, 80 and 85; Croda Inc., Edison NJ), TAMOL™ dispersants (The Dow Chemical Company, Midland, MI), TERGITOL™ surfactants (e.g., TMN-6 and TMN-100X; The Dow Chemical Company, Midland, MI), TERSPERSE surfactants (e.g., 2001, 2020, 2100, 2105, 2158, 2700, 4894 and 4896; Hunstman Corp., The Woodlands, TX), TRITON™ surfactants (e.g., X-100; The Dow Chemical Company, Midland, MI), TWEEN®surfactants (e.g., TWEEN®20, 21, 22, 23, 28, 40, 60, 61, 65, 80, 81 and 85; Croda International PLC, Edison, NJ) and combinations thereof. Additional examples of dispersants may be found in BAIRD & ZUBLENA. 1993. SOIL FACTS: USING WETTING AGENTS (NONIONIC SURFACTANTS) ON SOIL (North Carolina Cooperative Extension Service Publication AG-439-25) (1993); BURGES, FORMULATION OF MICROBIAL BIOPESTICIDES: BENEFICIAL MICROORGANISMS, NEMATODES AND SEED TREATMENTS (Springer Science & Business Media) (2012); MCCARTY, WETTING AGENTS (Clemson University Cooperative Extension Service Publication) (2001).

In some embodiments, inoculant compositions of the present disclosure comprise one or more anionic surfactants. According to some embodiments, the inoculant composition comprises one or more water-soluble anionic surfactants and/or one or more water-insoluble anionic surfactants, optionally one or more anionic surfactants selected from the group consisting of alkyl carboxylates (e.g., sodium stearate), alkyl sulfates (e.g., alkyl lauryl sulfate, sodium lauryl sulfate), alkyl ether sulfates, alkyl amido ether sulfates, alkyl aryl polyether sulfates, alkyl aryl sulfates, alkyl aryl sulfonates, alkyl sulfonates, alkyl amide sulfonates, alkyl aryl sulfonates, alkyl benzene sulfonates, alkyl diphenyloxide sulfonate, alpha-olefin sulfonates, alkyl naphthalene sulfonates, paraffin sulfonates, alkyl sulfosuccinates, alkyl ether sulfosuccinates, alkylamide sulfosuccinates, alkyl sulfosuccinamates, alkyl sulfoacetates, alkyl phosphates, alkyl ether phosphates, acyl sarconsinates, acyl isethionates, N-acyl taurates, N-acyl-N-alkyltaurates, benzene sulfonates, cumene sulfonates, dioctyl sodium sulfosuccinate, ethoxylated sulfosuccinates, lignin sulfonates, linear alkylbenzene sulfonates, monoglyceride sulfates, perfluorobutanesulfonate, perfluorooctanesulfonate, phosphate ester, styrene acrylic polymers, toluene sulfonates and xylene sulfonates.

In some embodiments, inoculant compositions of the present disclosure comprise one or more cationic surfactants.

According to some embodiments, the inoculant composition comprises one or more pH-dependent amines and/or one or more quaternary ammonium cations, optionally one or more cationic surfactants selected from the group consisting of alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide, dioctadecyldimethylammonium bromide and/or octenidine dihydrochloride.

In some embodiments, inoculant compositions of the present disclosure comprise one or more nonionic surfactants. According to some embodiments, the inoculant composition comprises one or more water-soluble nonionic surfactants and/or one or more water-insoluble nonionic surfactants, optionally one or more nonionic surfactants selected from the group consisting of alcohol ethoxylates (e.g., TERGITOL™ 15—S surfactants, such as TERGITOL™15-S-9 (The Dow Chemical Company, Midland, Ml)), alkanolamides, alkanolamine condensates, carboxylic acid esters, cetostearyl alcohol, cetyl alcohol, cocamide DEA, dodecyldimethylamine oxides, ethanolamides, ethoxylates of glycerol ester and glycol esters, ethylene oxide polymers, ethylene oxide-propylene oxide copolymers, glucoside alkyl ethers, glycerol alkyl ethers, glycerol esters, glycol alkyl ethers (e.g., polyoxyethylene glycol alkyl ethers, polyoxypropylene glycol alkyl ethers), glycol alkylphenol ethers (e.g., polyoxyethylene glycol alkylphenol ethers,), glycol esters, monolaurin, pentaethylene glycol monododecyl ethers, poloxamer, polyamines, polyglycerol polyricinoleate, polysorbate, polyoxyethylenated fatty acids, polyoxyethylenated mercaptans, polyoxyethylenated polyoxyproylene glycols, polyoxyethylene glycol sorbitan alkyl esters, polyethylene glycol-polypropylene glycol copolymers, polyoxyethylene glycol octylphenol ethers, polyvinyl pyrrolidones, sugar-based alkyl polyglycosides, sulfoanylamides, sorbitan fatty acid alcohol ethoxylates, sorbitan fatty acid ester ethoxylates, sorbitan fatty acid ester and/or tertiary acetylenic glycols.

In some embodiments, inoculant compositions of the present disclosure comprise at least one nonionic surfactant. According to some embodiments, the inoculant composition comprises at least one water insoluble nonionic surfactant and at least one water soluble nonionic surfactant. In some embodiments, inoculant compositions of the present disclosure comprise a combination of nonionic surfactants having hydrocarbon chains of substantially the same length.

In some embodiments, inoculant compositions of the present disclosure comprise one or more zwitterionic surfactants. According to some embodiments, the inoculant composition comprises one or more betaines and/or one or more sultaines, optionally one or more zwitterionic surfactants selected from the group consisting of 3-[(3-Cholamidopropyl)dimethylammonio]-1-propanesulfonate, cocamidopropyl betaine, cocamidopropyl hydroxysultaine, phosphatidylserine, phosphatidylethanolamine, phosphatidylcholine and/or one or more sphingomyelins.

In some embodiments, inoculant compositions of the present disclosure comprise one or more soaps and/or organosilicone surfactants. According to some embodiments, the inoculant composition comprises one or more alkali metal salts of fatty acids.

In some embodiments, inoculant compositions of the present disclosure comprise one or more wetting agents. According to some embodiments, the inoculant composition comprises one or more naphthalene sulfonates, optionally one or more alkyl naphthalene sulfonates (e.g., sodium alkyl naphthalene sulfonate), one or more isopropyl naphthalene sulfonates (e.g., sodium isopropyl naphthalene sulfonate) and/or one or more butyl naphthalene sulfonates (e.g., sodium n-butyl naphthalene sulfonate).

Inoculant compositions of the present disclosure may comprise any suitable drying agent(s), including, but not limited to, drying powders. Non-limiting examples of drying agents include AEROSIL® hydrophobic fumed silica powders (Evonik Corporation, Parsippany, NJ), BENTOLITE® powders (BYK-Chemie GmbH, Wesel, Germany), INCOTEC® powders (INCOTEC Inc., Salinas, CA), SIPERNAT® silica powders (Evonik Corporation, Parsippany, NJ) and combinations thereof. Additional examples of drying agents may be found in BURGES, FORMULATION OF MICROBIAL BIOPESTICIDES: BENEFICIAL MICROORGANISMS, NEMATODES AND SEED TREATMENTS (Springer Science & Business Media) (2012). In some embodiments, inoculant compositions of the present disclosure comprise calcium stearate, clay (e.g., attapulgite clay, montmorillonite clay), graphite, magnesium stearate, magnesium sulfate, powdered milk, silica (e.g., fumed silica, hydrophobically-coated silica, precipitated silica), soy lecithin and/or talc.

Inoculant compositions of the present disclosure may comprise any suitable anti-freezing agent(s), including, but not limited to, ethylene glycol, glycerin, propylene glycol and urea.

Inoculant compositions of the present disclosure may comprise any seed flowability agent to improve the lubricity of the treated seeds. The flowability agent may comprise one or more liquid lubricants, solid lubricants, liquid emulsions, or suspensions of solid lubricants. Non-limiting examples of flowability agents include, for example, lubricants such as fats and oils, natural and synthetic waxes, graphite, talc, fluoropolymers (e.g., polytetrafluoroethylene), and solid lubricants such as molybdenum disulfide and tungsten disulfide. In some instances, the flowability agent comprises a wax material. Non-limiting examples of wax materials that can be incorporated into the liquid seed treatment composition include plant and animal-derived waxes such as carnauba wax, candelilla wax, ouricury wax, beeswax, spermaceti, and petroleum derived waxes, such as paraffin wax. For example, in some instances, the flowability agent comprises carnauba wax. In some instances, the flowability agent comprises an oil. For example, the flowability agent may comprise soybean oil and/or tung oil. Non-limiting examples of commercially available materials suitable for use as flowability agents include AQUAKLEAN 418 supplied by Micro Powders, Inc. (an anionic aqueous emulsion comprising extra light carnauba wax at 35% solids content).

Inoculant compositions of the present disclosure may comprise any suitable safener(s), including, but not limited to, napthalic anhydride.

Inoculant compositions of the present disclosure may comprise any suitable pH buffer(s), including, but not limited to, potassium phosphate monobasic and potassium phosphate dibasic. In some embodiments, the inoculant composition comprises one or more pH buffers selected to provide a composition having a pH of less than 10, typically from about 4.5 to about 9.5, from about 6 to about 8, or about 7.

Inoculant compositions of the present disclosure may comprise any suitable anti-settling agent(s), including, but not limited to, polyvinyl acetate, polyvinyl alcohols with different degrees of hydrolysis, polyvinylpyrrolidones, polyacrylates, acrylate-, polyol- or polyester-based paint system binders which are soluble or dispersible in water, moreover copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, ot-methylstyrene or p-methylstyrene, further vinyl halides such as vinyl chloride and vinylidene chloride, additionally vinyl esters such as vinyl acetate, vinyl propionate or vinyl stearate, moreover vinyl methyl ketone or esters of acrylic acid or methacrylic acid with monohydric alcohols or polyols such as methyl acrylate, methyl methacrylate, ethyl acrylate, ethylene methacrylate, lauryl acrylate, lauryl methacrylate, decyl acrylate, N,N-dimethylamino-ethyl methacrylate, 2-hydroxyethyl methacrylate, 2-hydroxypropyl methacrylate or glycidyl methacrylate, furthermore diethyl esters or monoesters of unsaturated dicarboxylic acids, furthermore (meth)acrylamido-N-methylol methyl ether, amides or nitriles such as acrylamide, methacrylamide, N-methylol(meth)acrylamide, acrylonitrile, methacrylonitrile, and also N-substituted maleimides and ethers such as vinyl butyl ether, vinyl isobutyl ether or vinyl phenyl ether, and combinations thereof.

Inoculant compositions of the present disclosure may comprise any suitable adhesive(s), including, but not limited to, adhesive compositions comprising, consisting essentially of or consisting of one or more disaccharides (e.g. maltose), gums (e.g., cellulose gum, guar gum, gum arabic, gum combretum, xanthan gum), maltodextrins (e.g., one or more maltodextrins (each and/or collectively) having a DEV of about 10 to about 20), monosaccharides, oils (e.g., mineral oil, olive oil, peanut oil, soybean oil, sunflower oil and/or tung oil) and/or oligosaccharides.

Inoculant compositions of the present disclosure may comprise any suitable effect pigment(s). Effect pigments, which are sometimes also referred to in the art as "pearl pigments," are a class of materials that provide reflectivity, shine, and/or a pearlescent effect when applied as a coating. In some instances, the effect pigment is in the form of a powder comprising a substrate material and a metal oxide coating. For example, the effect pigment may comprise a substrate material including but not limited to talc, silicate materials (e.g., mica), clay minerals, calcium carbonate, kaolin, phlogopite, alumina, and similar substances. In some instances, the substrate material comprises a hydrophilic material. The substrate material may be coated with a semi-transparent layer of a metal oxide, including but not limited to titanium dioxide, iron oxide, chromium oxide, or zirconium oxide. Alternatively, in some instances, the effect pigment comprises metal powder or metal flakes. The metal powder or metal flakes may comprise a metal including, but not limited to aluminum, copper, silver, or bronze. In some instances, the effect pigment comprises a silicate based substrate. Non-limiting examples of particulate silicates that can be incorporated into the dry powder coating include mica coated with titanium dioxide (e.g., SUNMICA FINE WHITE 2800102, which is commercially available from Sun Chemical Corp.).

Other non-limiting examples of commercially available effect pigments that can be incorporated into the dry powder include *MAGNA* PEARL, LUMINA and MEARLIN pigments from BASF Corporation; PHIBRO PEARL from PhibroChem; and IRIDESIUM 120 from Aakash Chemicals. In some instances, the dry powder has a mean particle size of from about 1 to about 25 microns.

Inoculant compositions of the present disclosure may comprise any suitable growth medium suitable for culturing one or more of the microorganisms in the inoculant composition. For example, in some embodiments, inoculant compositions of the present disclosure comprise Czapek-Dox medium, glycerol yeast extract, mannitol yeast extract, potato dextrose broth and/or YEM media.

Stabilizing compounds, biostimulants, microbial extracts, nutrients, pest attractants and/or feeding stimulants, pesticides, LCOs, chitin oligomers, chitosan oligomers, chitins, chitosans, flavonoids, dispersants, drying agents, safeners, flowability agents, anti-settling agents, buffers, adhesives, etc. may be incorporated into inoculant compositions of the present disclosure in any suitable amount(s)/concentration(s). The absolute value of the amount/concentration that is/are sufficient to cause the desired effect(s) may be affected by factors such as the type, size and volume of material to which the compositon will be applied, the type(s) of microorganisms in the composition, the number of microorganisms in the composition, the stability of the microorganisms in the composition and storage conditions (e.g., temperature, relative humidity, duration). Those skilled in the art will understand how to select effective amounts/concentrations using routine dose-response experiments. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; and 62/347,805.

In some embodiments, inoculant compositions of the present disclosure comprise one or more stabilizing compounds in an amount/concentration of about 0.0001 to about 95% or more (by weight, based upon the total of the inoculant composition). For example, inoculant compositions of the present disclosure may comprise about 0.0001 to about 0.001, about 0.001 to about 1%, about 0.25 to about 5%, about 1 to about 10%, about 5 to about 25%, about 10% to about 30%, about 20% to about 40%, about 25% to about 50%, about 30 to about 60%, about 50 to about 75%, or about 75 to about 95% (by weight), optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% of one or more maltodextrins, monosaccharides, disaccharides, sugar alcohols, humic acids, betaines, prolines, sarcosines, peptones, oxidation control components, hygroscopic polymers and/or UV protectants.

In some embodiments, inoculant compositions of the present disclosure comprise one or more stabilizing compounds at a concentration of about $1\times10^{-20}$ M to about $1\times10^{-1}$ M. For example, inoculant compositions of the present disclosure may comprise about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M, optionally about $1\times10^{-20}$ M, $1\times10^{-19}$ M, $1\times10^{-1}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more, of one or more maltodextrins, monosaccharides, disaccharides, sugar alcohols, humic acids, betaines, prolines, sarcosines, peptones, oxidation control components, hygroscopic polymers and/or UV protectants.

In some embodiments, inoculant compositions of the present disclosure comprise one or more monosaccharides in an amount/concentration of about 0.005 to about 50% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more monosaccharides (e.g., arabinose, fructose and/or glucose). In some embodiments, one or more monosaccharides is/are present in a concentration ranging from about $1\times10^{-20}$ M to about $1\times10^{-1}$ M. For example, one or more monosaccharides may be included at a concentration of about/at least/less than $1\times10^{-20}$ M, $1\times10^{-19}$ M, $1\times10^{-15}$ M, $1\times10^{-17}$ M, $1\times10^{-16}$ M, $1\times10^{-15}$ M, $1\times10^{-4}$ M, $1\times10^{-1}$ M, $1\times10^{-12}$ M, $1\times10^{-1}$ M, $1\times10^{-10}$ M.

In some embodiments, inoculant compositions of the present disclosure comprise one or more disaccharides in an amount/concentration of about 0.005 to about 50% (by weight) of the inoculant composition. For example, inocu-lant compositions of the present disclosure may comprise about/at least/less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5, 5.5, 6, 6.5, 7, 7.5, 8, 8.5, 9, 10, 15, 20, 25% (by weight) of one or more disaccharides (e.g., maltose, sucrose and/or trehalose). In some embodiments, one or more disaccharides is/are present in a concentration ranging from about $1\times10^{-20}$ M to about $1\times10^{-1}$ M. For example, one or more disaccharides may be included at a concentration of about/at least/less than $1\times10^{-20}$ M, $1\times10^{-19}$ M, $1\times10^{-11}$ M, $1\times10^{-1}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M.

In some embodiments, inoculant compositions of the present disclosure comprise one or more maltodextrins in an amount/concentration of about 0.001 to about 95% or more (by weight) of the inoculant composition. In some embodiments, the maltodextrin(s) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more maltodextrins (e.g., one or more maltodextrins (each and/or collectively) having a DEV value of about 15 to about 20).

In some embodiments, inoculant compositions of the present disclosure comprise one or more sugar alcohols in an amount/concentration of about 0.001 to about 95% or more (by weight) of the inoculant composition. In some embodiments, the sugar alcohol(s) (e.g., arabitol, mannitol, sorbitol and/or xylitol) comprise(s) about 0.001 to about 1%, about 0.25 to about 5%, about 1 to about 10%, about 5 to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more sugar alcohols (e.g., arabitol, mannitol, sorbitol and/or xylitol).

In some embodiments, inoculant compositions of the present disclosure comprise one or more humic acids in an amount/concentration of about 0.001 to about 95% or more (by weight) of the inoculant composition. In some embodiments, the humic acid(s) (e.g., potassium humate) comprise(s) about 0.001 to about 1%, about 0.25 to about 5%, about 1 to about 10%, about to about 25%, about 10% to about 30%, about 20% to about 40%, about 25% to about 50%, about 50 to about 75%, or about 75 to about 95% (by weight) of the inoculant composition. For example, inoculant compositions of the present disclosure may comprise about/at least/less than 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more humic acids (e.g., potassium humate and/or sodium humate).

In some embodiments, inoculant compositions of the present disclosure comprise one or more UV protectants in an amount/concentration of about 0.0001 to about 5% or more (by weight) of the inoculant composition. In some embodiments, the UV protectant(s) (e.g., calcium lignosulfate and/or sodium lignosulfate) comprise(s) about 0.0001 to about 0.001, about 0.001 to about 1%, about 0.25 to about 5%, (by weight) of the inoculant composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% or more (by weight) of one or more UV protectants (e.g., calcium lignosulfate and/or sodium lignosulfate).

In some embodiments, inoculant compositions of the present disclosure comprise one or more oxidation control components in an amount/concentration of about 0.0001 to about 5% or more (by weight) of the composition. For example, inoculant compositions of the present disclosure may comprise about/at least/less than 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.75, 1, 1.25, 1.5, 2, 2.5, 3, 3.5, 4, 4.5, 5% of one or more oxidation control components. In some embodiments, the amount/concentration of oxidation control components is about 0.005 to about 2% (by weight) of the composition. In some embodiments, the oxidation control component(s) is/are present in a concentration ranging from about $1\times10^{-20}$ M to about $1\times10^{-1}$ M. For example, one or more oxidation control components may be added at a concentration of about/at least/less than $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M. In some embodiments, inoculant compositions of the present disclosure comprise one or more commercial antioxidants used in accordance with the manufacturer's recommended amounts/concentrations. In some embodiments, inoculant compositions of the present disclosure comprise one or more commercial oxygen scavengers used in accordance with the manufacturer's recommended amounts/concentrations.

In some embodiments, inoculant compositions of the present disclosure comprise one or more stabilizing compounds in an amount/concentration sufficient to ensure vegetative cells therein remain viable following:
  storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  desiccation by about 5, 10, 15, 20, 25, 30, 35, 40, 45, 50, 55, 60, 65, 70, 75, 80, 85, 90, 95% or more;
  desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or
foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more stabilizing compounds in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of any vegetative cells therein remain viable following:
  storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  desiccation by about 5, 10, 15, 20, 25, 30, 35, 40, 45, 50, 55, 60, 65, 70, 75, 80, 85, 90, 95% or more;
  desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;
  application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more stabilizing compounds in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units of any vegetative cells therein remain viable per gram and/or milliliter of inoculant composition following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, inoculant compositions of the present disclosure comprise one or more stabilizing compounds in an amount/concentration sufficient to ensure the deliquescence relative humidity (DRH) of the inoculant composition is less than 5, 10, 15, 20, 25, 30, 35, 40, 45, 50, 55, 60, 65, 70, 75, 80, 85 or 90 at the temperature(s) at which the composition is to be stored (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C.).

In some embodiments, inoculant compositions of the present disclosure comprise two or more stabilizing compounds that synergistically enhance the stability and/or survival of vegetative cells therein.

Stabilizing compounds may be incorporated into inoculant compositions of the present disclosure in any suitable ratio(s).

In some embodiments, inoculant compositions of the present disclosure comprise one or more maltodextrins and one or more monosaccharides, disaccharides, sugar alcohols and/or humic acids in a maltodextrin:(monosaccharide, disaccharide, sugar alcohol and/or humic acid) ratio of about 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5. For example, inoculant compositions of the present disclosure may comprise one or more maltodextrins (e.g., one or more maltodextrins (each and/or collectively) having a DEV of about 15 to about 20) and one or more sugar alcohols (e.g., sorbitol and/or xylitol) and/or humic acids (e.g., potassium humate) in a maltodextrin:(sugar alcohol/humic acid) ratio of about 5:95, about 15:85, about 25:75 or about 50:50.

In some embodiments, inoculant compositions of the present disclosure comprise one or more biostimulants in an amount/concentration of about 0.0001 to about 5% or more (by weight) of the inoculant composition. In some embodiments, the biostimulant(s) (e.g., glycine and/or seaweed extract) comprise(s) about about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of one or more biostimulants (e.g., glycine and/or seaweed extract).

In some embodiments, inoculant compositions of the present disclosure comprise one or more microbial extracts in an amount/concentration of about 0.0001 to about 5% or more (by weight) of the inoculant composition. In some embodiments, the microbial extract(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of one or more microbial extracts.

In some embodiments, inoculant compositions of the present disclosure comprise one or more nutrients in an amount/concentration of about 0.0001 to about 5% or more (by weight) of the inoculant composition. In some embodiments, the nutrient(s) (e.g., phosphorous, boron, chlorine, copper, iron, manganese, molybdenum and/or zinc) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of one or more the nutrients (e.g., phosphorous, boron, chlorine, copper, iron, manganese, molybdenum and/or zinc).

In some embodiments, inoculant compositions of the present disclosure comprise one or more pest attractant(s) and/or feeding stimulant(s) in an amount/concentration of about 0.0001 to about 5% or more (by weight) of the inoculant composition. In some embodiments, the pest attractant(s) and/or feeding stimulant(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of one or more pest attractants and/or feeding stimulants.

In some embodiments, inoculant compositions of the present disclosure comprise one or more LCOs at a concentration of about $1\times10^{-15}$ M to about $1\times10^{-10}$ M, about $1\times10^{-14}$ M to about $1\times10^{-8}$ M, about $1\times10^{-4}$ M to about $1\times10^{-16}$ M, about $1\times10^{-18}$ M to about $1\times10^{-17}$ M, about $1\times10^{-12}$ M to about $1\times10^{-16}$ M, about $1\times10^{-15}$ M to about $1\times10^{-16}$ M, or about $1\times10^{-1}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-4}$ M, $1\times10^{-1}$ M, $1\times10^{-12}$ M, $1\times10^{-11}$ M, $1\times^{-10}$ M, $10^{-9}$M, $1\times10^{-10}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more LCOs (e.g., one, two, three, four or more of the LCOs described above).

In some embodiments, inoculant compositions of the present disclosure comprise one or more chitin oligosaccharides at a concentration of about $1\times10^{-15}$ M to about $1\times10^{-10}$ M, about $1\times10^{-14}$ M to about $1\times10^{-6}$ M, about $1\times10^{-12}$ M to about $1\times10^{-6}$ M, about $1\times10^{-12}$ M to about $1\times10^{-10}$ M, about $1\times10^{-12}$ M to about $1\times10^{-6}$ M, about $1\times10^{-10}$ M to about $1\times10^{-6}$ M, or about $1\times10^{-19}$ M to about $1\times10^{-2}$ M. For example, inoculant compositions of the present disclosure may comprise about $1\times10^{-20}$ M, $1\times10^{-19}$M, $1\times10^{-18}$ M, $1\times10^{-17}$M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$M, $1\times10^{-9}$ M, $1\times10^{-8}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitin oligosaccharides (e.g., one, two, three, four or more of the chitin oligosaccharides described above).

In some embodiments, inoculant compositions of the present disclosure comprise one or more chitosan oligosaccharides at a concentration of about $1\times10^{-1}$ M to about $1\times10^{-10}$ M, about $1\times10^{-14}$ M to about $1\times10^{-1}$ M, about $1\times10^{-14}$ M to about $1\times10^{-6}$ M, about $1\times10^{-2}$ M to about $1\times10^{-1}$ M, about $1\times10^{-12}$ M to about $1\times10^{-6}$ M, about $1\times10^{-1}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$M, $1\times10^{-18}$ M, $1\times10^{-17}$M, $1\times10^{-16}$1M, $1\times10^{-15}$ M, $1\times10^{-14}$M, $1\times10^{-13}$M, $1\times10^{-12}$M, $1\times10^{-11}$ M, $1\times10^{-11}$M, $1\times10{-9}$ M, $1\times10^{-1}$ M, $1\times10^{-7}$ M, $1\times10^{-6}$ M, $1\times10^{-5}$ M, $1\times10^{-4}$ M, $1\times10^{-1}$ M, $1\times10^{-2}$ M, $1\times10^{-1}$ M or more of one or more chitosan oligosaccharides.

In some embodiments, inoculant compositions of the present disclosure comprise one or more chitins at a concentration of about $1\times10^{-15}$ M to about $1\times10^{-10}$ M, about $1\times10^{-14}$ M to about $1\times10^{-8}$ M, about $1\times10^{-14}$ M to about $1\times10^{-6}$ M, about $1\times10^{-12}$ M to about $1\times10^{-8}$ M, about $1\times10^{-12}$ M to about $1\times10^{-6}$ M, about $1\times10^{-10}$ M to about $1\times10^{-6}$ M, or about $1\times10^{-8}$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$ M, $1\times10^{-13}$ M, $1\times10^{-12}$ M, $1\times10^{-11}$ M, $1\times10^{-10}$ M, $1\times10^{-9}$ M, $1\times10^{-1}$ M, $1\times10^{-7}$ M, $1\times10^{-6}$ M, $1\times10^{-5}$ M, $1\times10^{-4}$ M, $1\times10^{-3}$ M, $1\times10^{-2}$ M, $1\times10^{-1}$ M or more of one or more chitins.

In some embodiments, inoculant compositions of the present disclosure comprise one or more chitosans at a concentration of about $1\times10^{-15}$ M to about $1\times10^{-11}$ M, about $1\times10^{-14}$ M to about $1\times10^{-8}$ M, about $1\times10^{-4}$ M to about $1\times10^{-6}$ M, about $1\times10^{-12}$ M to about $1\times10^{-8}$ M, about $1\times10^{-12}$ M to about $1\times10.6$ M, about $1\times10^{-1}$ M to about $1\times10.6$ M, or about $1\times10.0$ M to about $1\times10^{-2}$ M. For example, inoculant compositions of the present disclosure may comprise about $1\times10^{-20}$ M, $1\times10^{-19}$ M, $1\times10^{-18}$ M, $1\times10^{-17}$ M, $1\times10^{-16}$ M, $1\times10^{-15}$ M, $1\times10^{-14}$M, $1\times10^{-13}$ M, $1\times10^{-12}$ M, $1\times10^{-11}$ M, $1\times10^{-10}$M, $1\times10^{-9}$M, $\times10^{-8}$ M, $1\times10^{-7}$M, $1\times10^{-6}$M, $1\times10^{-5}$M, $1\times10^{-4}$M, $1\times10^{-3}$M, $1\times10^{-2}$ M, $1\times10^{-1}$ M or more of one or more chitosans.

In some embodiments, inoculant compositions of the present disclosure comprise one or more flavonoids in an amount/concentration of about 0.0001 to about 5% or more (by weight) of the inoculant composition. In some embodiments, the flavonoid(s) (e.g., one or more flavones and/or flavanones) comprise(s) about about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of one or more flavonoids (e.g., one or more flavones and/or flavanones).

In some embodiments, inoculant compositions of the present disclosure comprise one or more dispersants in an amount/concentration of about 0.001 to about 25% or more (by weight) of the inoculant composition. In some embodiments, the dispersant(s) comprise(s) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20% or more (by weight) of one or more dispersants (e.g., one or more surfactants and/or wetting agents).

In some embodiments, inoculant compositions of the present disclosure comprise one or more drying agents in an amount/concentration of about 0.001 to about 95% or more (by weight) of the inoculant composition. In some embodiments, the drying agent(s) comprise(s) about) 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5, 6, 7, 8, 9 or 10 to about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20% (by weight) of the inoculant composition. For example, inoculant compositions of the present disclosure may comprise about 0.01, 0.02, 0.03, 0.04, 0.05, 0.06, 0.07, 0.08, 0.09, 0.1, 0.2, 0.3, 0.4, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95% or more (by weight) of one or more drying agents (e.g., talc).

In some embodiments, the inoculant compositions of the present disclosure comprise about 0.5 to about 10 grams of drying powder per liter of inoculant composition. For example, inoculant compositions of the present disclosure may comprise about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder per liter of inoculant composition.

In some embodiments, inoculant compositions of the present disclosure comprise one or more buffers in an amount/concentration of about 0.0001 to about 5% or more (by weight) of the inoculant composition. In some embodiments, the buffer(s) comprise(s) about 0.0001, 0.0002, 0.0003, 0.0004, 0.0005, 0.0006, 0.0007, 0.0008, 0.0009, 0.001, 0.0015, 0.002, 0.0025, 0.003, 0.0035, 0.004, 0.0045, 0.005, 0.0055, 0.006, 0.0065, 0.007, 0.0075, 0.008, 0.0085, 0.009, 0.0095, 0.01, 0.015, 0.02, 0.025, 0.03, 0.035, 0.04, 0.045, 0.05, 0.06, 0.07, 0.08, 0.09, 0.1, 0.02, 0.3, 0.4, 0.5, 0.6, 0.7, 0.8, 0.9, 1 to about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% (by weight) of the inoculant composition. For example, inoculant compositions of the present disclosure may comprise about 0.0005, 0.00075, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of one or more buffers (e.g., potassium phosphate monobasic and/or potassium phosphate dibasic).

In some embodiments, inoculant compositions of the present disclosure comprise one or more commercial antioxidants, oxygen scavengers, hygroscopic polymers, UV protectants, biostimulants, microbial extracts, nutrients, pest attractants and/or feeding stimulants, pesticides, plant signal molecules, disperants, drying agents, anti-freezing agents, buffers and/or adhesives used in accordance with the manufacturer's recommended amounts/concentrations.

Inoculant compositions of the present disclosure may be formulated as any suitable type of composition, including, but not limited to, foliar inoculants, seed coatings and soil inoculants.

In some embodiments, inoculant compositions of the present disclosure are formulated as non-aqueous formulations in which at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial cells/spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure are formulated such that at least about 5, 6, 7, 8, 9, 10, 11, 12, 13, 14, 15, 16, 17, 18, 19, 20, 25, 30, 35, 40, 45, 50, 55, 60, 65, 70% or more of the microorganisms therein survive when the inoculant composition is coated on a seed and stored at 20, 21, 22, 23, 24, 25, 26, 27, 28, 29 and/or 30° C. and 50, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as non-aqueous formulations in which at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/gram or more of the microbial cells/spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as non-aqueous formulations in which at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/ml or more of the microbial cells/spores therein survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as non-aqueous formulations in which at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ cfu/seed or more of the microorganisms therein survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure are formulated as amorphous liquids.

In some embodiments, inoculant compositions of the present disclosure comprise no water.

In some embodiments, inoculant compositions of the present disclosure comprise a trace amount of water.

In some embodiments, inoculant compositions of the present disclosure comprise less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

In some embodiments, inoculant compositions of the present disclosure are formulated to have a pH of about 4.5 to about 9.5. In some embodiments, inoculant compositions of the present disclosure have a pH of about 6 to about 7.5. In some embodiments, inoculant compositions of the present disclosure have a pH of about 5, 5.5, 6, 6.5, 7, 7.5, 8 or 8.5.

It is to be understood that inoculant compositions of the present disclosure are non-naturally occurring compositions.

According to some embodiments, the inoculant composition comprises one or more non-naturally occurring components. According to some embodiments, the inoculant composition comprises a non-naturally occurring combination of naturally occurring components.

Inoculant compositions of the present disclosure exhibit numerous beneficial properties, including, but not limited to, the capability of enhancing both the stability and survival of microbial cells/spores therein.

In some embodiments, inoculant compositions of the present disclosure improve the stability of one or more microbial cells/spores contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure).

For example, inoculant compositions of the present disclosure may improve one or more of the microbial stability characteristics of one or more of the microbial cells/spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that it lacks one or more of the paraffin oils and/or waxes and/or comprises a reduced amount of one or more of the paraffin oils and/or waxes.

In some embodiments, microbial cells/spores remain viable in inoculant compositions of the present disclosure for at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more (e.g., at least 12, 16, 20, 24, 28, 32, 36, 40, 44, 48, 52, 56, 60, 64, 68, 72, 76, 80, 84, 88, 92, 96, 100, 104 weeks or more when stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity).

In some embodiments, inoculant compositions of the present disclosure improve the survival rate of one or more microbial cells/spores contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, inoculant compositions of the present disclosure may improve the survival rate of one or more of the microbial cells/spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that it lacks one or more of the paraffin oils and/or waxes and/or comprises a reduced amount of one or more of the paraffin oils and/or waxes.

In some embodiments, inoculant compositions of the present disclosure improve the survival of one or more of the microbial cells/spores contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial cells/spores survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial cells/spores contained therein to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microbial cells/spores survive when the inoculant composition is stored at 10, 11, 12, 13, 14, 15, 16, 17, 18, 19, 20, 21, 22, 23, 24, 25, 26, 27, 28, 29 and/or 30° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microbial cells/spores contained therein to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial cells/spores survive when the inoculant composition is desiccated by about 5, 10, 15, 20, 25, 30, 35, 40, 45, 50, 55, 60, 65, 70, 75, 80, 85, 90, 95% or more and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial cells/spores contained therein to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microbial cells/spores survive when the inoculant composition is coated on a seed, dried and stored at 10, 11, 12, 13, 14, 15, 16, 17, 18, 19, 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microbial cells/spores contained therein to the extent that at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/gram or milliliter or more of the microbial cells/spores survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial cells/spores contained therein to the extent that at least $1 \times 10^4$, $1 \times 10^5$, $1 \times 10^6$, $1 \times 10^7$ cfu/seed or more of the microbial cells/spores survive when the inoculant composition is stored at 10, 11, 12, 13, 14, 15, 16, 17, 18, 19, 20, 21, 22, 23, 24, 25, 26, 27, 28, 29 and/or 30° for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve the survival of one or more of the microbial cells/spores contained therein to the extent that at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/gram or milliliter or more of the microbial cells/spores survive when the inoculant composition is desiccated by about 5, 10, 15, 20, 25, 30, 35, 40, 45, 50, 55, 60, 65, 70, 75, 80, 85, 90, 95% or more and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, inoculant compositions of the present disclosure improve the survival of one or more of the microbial cells/spores contained therein to the extent that at least $1 \times 10^4$, $1 \times 10^5$, $1 \times 10^6$, $1 \times 10^7$ cfu/seed or more of the microbial cells/spores survive when the inoculant composition is coated on a seed, dried and stored at 10, 11, 12, 13, 14, 15, 16, 17, 18, 19, 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, inoculant compositions of the present disclosure improve both the survival rate and one, two, three, four, five, six, seven, eight, nine, ten or more microbial stability characteristics of the microbial spore(s) contained therein.

In some embodiments, inoculant compositions of the present disclosure improve the dispersion of one or more microbial cells/spores contained therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure).

For example, inoculant compositions of the present disclosure may improve the dispersion of one or more of the microbial cells/spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that it lacks one or more of the paraffin oils and/or waxes and/or comprises a reduced amount of one or more of the paraffin oils and/or waxes.

In some embodiments, inoculant compositions of the present disclosure improve the dispersion of one or more of the microbial cells/spores contained therein to the extent that at least about 50, 55, 60, 65, 70, 75, 80, 85, 90, 95% or more of the microbial cells/spores are present as single cells/spores (rather than as members of a clump comprising two or more cells/spores).

Inoculant compositions of the present disclosure may be used to improve any suitable microbial stability characteristic(s), including, but not limited to, the ability of microbial cells/spores therein to enhance plant yield after being coated on a seed and stored for a defined period of time prior to planting the seed. For example, in some embodiments, inoculant compositions of the present disclosure improve the ability of the microbial cells/spores therein to propagate and increase yield after being coated on a plant propagation material (e.g., seed) and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

As noted above, inoculant compositions of the present disclosure may comprise agriculturally beneficial constituents, such as biostimulants, microbial extracts, nutrients, pesticides and plant signal molecules. It is to be understood that agriculturally beneficial constituents may also be used in conjunction with inoculant compositions of the present disclosure. Thus, the present disclosure extends to systems and methods of using inoculant compositions of the present disclosure in conjunction with compositions comprising one or more agriculturally beneficial constituents (e.g., a second composition comprising one or more LCOs and/or chitin oligomers, a third composition comprising one or more fungicides, herbicides, insecticides and/or nematicides, etc.).

The present disclosure extends to kits comprising, consisting essentially of, or consisting of two or more containers, each comprising one or more components of an inoculant compositon of the present disclosure. For example, the microbial cells/spores and the carrier may be housed in separate containers for long-term storage, then combined prior to applying the inoculant composition to a target medium (e.g., a plant or plant propagation material). Optional constituents, such as stabilizing compounds, pesticides and plant signaling molecules, may be added to either of the two containers or housed in one or more separate containers for long-term storage. In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The containers may comprise any suitable material(s), including, but not limited to, materials that reduce the amount of light, moisture and/or oxygen that contact the coated plant propagation material when the container is sealed. In some embodiments, the containers comprise, consist essentially of, or consist of a material having light permeability of less than about 1, 2, 3, 4, 5, 6, 7, 8, 9, 10, 15, 20, 25, 30, 35, 40, 45, 50, 55, 60, 65, 70 or 75%. In some embodiments, the containers comprise, consist essentially of, or consist of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$·day (as measured in accordance with ASTM D3985).

In some embodiments, the containers reduce the amount of ambient light, moisture and/or oxygen that reaches said coated plant propagation material by about 5, 10, 15, 20, 25, 30, 35, 40, 45, 50, 55, 60, 65, 70, 75, 80, 85, 90, 95 or 100% when sealed.

Inoculant compositions of the present disclosure may be applied to any plant type, including, but not limited to, row crops and vegetables. In some embodiments, inoculant compositions of the present disclosure are formulated for the treatment of one or more plants selected from the families Amaranthaceae (e.g., chard, spinach, sugar beet, *quinoa*), Asteraceae (e.g., artichoke, asters, chamomile, chicory, chrysanthemums, dahlias, daisies, *echinacea*, goldenrod, guayule, lettuce, marigolds, safflower, sunflowers, zinnias), Brassicaceae (e.g., arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, *Arabidopsis thaliana*), Cucurbitaceae (e.g., cantaloupe, cucumber, honeydew, melon, pumpkin, squash (e.g., acorn squash, butternut squash, summer squash), watermelon, zucchini), Fabaceae (e.g., alfalfa, beans, carob, clover, guar, lentils, mesquite, peas, peanuts, soybeans, tamarind, tragacanth, vetch), Malvaceae (e.g., cacao, cotton, durian, hibiscus, kenaf, kola, okra), Poaceae (e.g., bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, wheat and other cereal crops, Polygonaceae (e.g., buckwheat), Rosaceae (e.g., almonds, apples, apricots, blackberry, blueberry, cherries, peaches, plums, quinces, raspberries, roses, strawberries), Solanaceae (e.g., bell peppers, chili peppers, eggplant, *petunia*, potato, tobacco, tomato) and Vitaceae (e.g., grape). In some embodiments, inoculant compositions of the present disclosure are formulated for the treatment of one or more plants with which the microbial cells/spores are not naturally associated (e.g., one or more plants that does not naturally exist in the geographical location(s) in which the microbial cells/spores naturally exist). In some embodiments, inoculant compositions of the present disclosure are formulated for the treatment of one or more acaricide-, fungicide-, gastropodicide-, herbicide-, insecticide-, nematicide-, rodenticide- and/or virucide-resistant plants (e.g., one or more plants resistant to acetolactate synthase inhibitors (e.g., imidazolinone, pryimidinyoxy (thio)benzoates, sulfonylaminocarbonyltriazolinone, sulfonylurea, triazolopyrimidines), bialaphos, glufosinate, glyphosate, hydroxyphenylpyruvatedioxygenase inhibitors and/or phosphinothricin). Non-limiting examples of plants that may be treated with inoculant compositions of the present disclosure include plants sold by Monsanto Company (St. Louis, MO) under the BOLLGARD II®, DROUGHTGARD®, GENUITY®, INTACTA, INTACTA RR2 PRO, RIB COMPLETE®, ROUNDUP READY®, ROUNDUP READY 2 YIELD®, ROUNDUP READY 2 EXTEND™, SMARTSTAX®, VT DOUBLE PRO®, VT TRIPLE PRO®, YIELDGARD®, YIELDGARD VT ROOTWORM/RR2®, YIELDGARD VT TRIPLE® and/or XTENDFLEX™ tradenames.

Inoculant compositions of the present disclosure may be applied to any part/portion of a plant. In some embodiments, inoculant compositions of the present disclosure are formulated for the treatment of plant propagation materials (e.g., cuttings, rhizomes, seeds and tubers). In some embodiments, inoculant compositions of the present disclosure are formulated for the treatment of plant roots. In some embodiments, inoculant compositions of the present disclosure are formulated for the treatment of plant foliage. In some embodiments, inoculant compositions of the present disclosure are formulated for the treatment of both the roots and the foliage of a plant. In some embodiments, inoculant compositions of the present disclosure are formulated for the treatment of plant propagation materials and the plants that grow from said plant propagation materials.

Inoculant compositions of the present disclosure may be applied to any plant growth medium, including, but not limited to, soil.

Inoculant compositions of the present disclosure may be applied to plants, plant parts and/or plant growth media in any suitable manner, including, but not limited to, on-seed application, in-furrow application and foliar application.

Inoculant compositions of the present disclosure may be applied using any suitable method(s), including, but not limited to, coating, dripping, dusting, encapsulating, immersing, spraying and soaking. Batch systems, in which predetermined batch sizes of material and inoculant composition are delivered into a mixer, may be employed. Continuous treatment systems, which are calibrated to apply inoculant composition at a predefined rate in proportion to a continuous flow of material, may also be employed.

In some embodiments, inoculant compositions of the present disclosure are applied directly to plant propagation material (e.g., seeds). According to some embodiments, plant propagation materials are soaked in an inoculant composition of the present disclosure for at least 0.1, 0.2, 0.3, 0.4, 0.5, 0.6, 0.7, 0.8, 0.9, 1, 1.25, 1.5, 1.75, 2, 3, 4, 5, 6, 9, 12, 15, 18, 21, 24, 36, 48 hours.

According to some embodiments, plant propagation materials are coated with an inoculant composition of the present disclosure.

Plant propagation materials may be coated with one or more additional layers (e.g., one or more protective layers that serves to further enhance the stability and/or survival of microbial spores and/or vegetative cells in the inoculant composition and/or one or more sequestration layers comprising substances that may reduce the stability and/or survival of microbial spores and/or vegetative cells in the inoculant composition if included in same layer as said microbial spores and/or vegetative cells). In some embodiments, the coating comprises, consists essentially of, or consists of an inoculant composition of the present disclosure and a drying powder.

In some embodiments, inoculant compositions of the present disclosure are applied directly to a plant growth medium (e.g., a soil). According to some embodiments, inoculant compositions of the present disclosure are applied in the vicinity of a plant propagation material (e.g., a seed). According to some embodiments, inoculant compositions of the present disclosure are applied to the root zone of a plant. According to some embodiments, inoculant compositions of the present disclosure are applied using a drip irrigation system.

In some embodiments, inoculant compositions of the present disclosure are applied directly to plants. According to some embodiments, inoculant compositions of the present disclosure are sprayed and/or sprinkled on the plant(s) to be treated.

In some embodiments, inoculant compositions of the present disclosure are freeze- spray- or spray-freeze-dried and then applied to plants/plant parts. For examples, in some embodiments, an inoculant composition comprising one or more paraffin oils and/or waxes as well as one or more stabilizing components (e.g., one or more maltodextrins having a DEV of about 15 to about 20) is freeze- spray- or spray-freeze-dried, mixed with a drying powder (e.g., a drying powder comprising calcium stearate, attapulgite clay, montmorillonite clay, graphite, magnesium stearate, silica (e.g., fumed silica, hydrophobically-coated silica and/or precipitated silica) and/or talc), then coated on seed that was been pre-treated with one or more adhesives (e.g., an adhesive composition comprising one or more maltodextrins, one or more mono-, di- or oligosaccharides, one or more peptones, etc.), one or more pesticides and/or one or more plant signal molecules (e.g., one or more LCOs).

Inoculant compositions of the present disclosure may be applied to plants, plant parts and/or plant growth media in any suitable amount(s)/concentration(s).

In some embodiments, inoculant compositions of the present disclosure are applied at a rate of about 0.05 to about 100 milliliters and/or grams of inoculant composition per kilogram of plant propagation material. According to some embodiments, one or more inoculant compositions of the present disclosure is/are applied in an amount sufficient to ensure the plant propagation materials are coated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant compositions per kilogram of plant propagation material. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each seed.

In some embodiments, inoculant compositions of the present disclosure are applied at a rate of about 0.5 to about 100 milliliters and/or grams of inoculant composition per plant. According to some embodiments, one or more inoculant compositions of the present disclosure is/are applied in an amount sufficient to ensure each plant is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each plant.

In some embodiments, inoculant compositions of the present disclosure are applied at a rate of about 0.5 to about 100 milliliters and/or grams of inoculant composition per acre of treated crops. According to some embodiments, one or more inoculant compositions of the present disclosure is/are applied in an amount sufficient to ensure each acre of treated crops is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each acre of treated crops.

In some embodiments, inoculant compositions of the present disclosure are applied at a rate of about 0.5 to about 100 milliliters and/or grams of inoculant composition per acre of plant growth media. According to some embodiments, one or more inoculant compositions of the present disclosure is/are applied in an amount sufficient to ensure each acre of plant growth media is treated with about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10, 20, 30, 40, 50, 60, 70, 80, 90 or 100 milliliters and/or grams of inoculant composition. According to some embodiments, one or more inoculant compositions of the present disclosure is/are applied in an amount sufficient to ensure that an average of about/at least 0.05, 0.1, 0.125, 0.15, 0.175, 0.2, 0.225, 0.2.5, 0.275, 0.3, 0.325, 0.35, 0.375, 0.4, 0.425, 0.45, 0.475, 0.5, 0.55, 0.6, 0.65, 0.7, 0.75, 0.8, 0.85, 0.9, 0.95, 1, 1.25, 1.5, 1.75, 2, 2.25, 2.5, 2.75, 3, 3.25, 3.5, 3.75, 4, 4.25, 4.5, 4.75 or 5 milliliters and/or grams of inoculant composition is applied to each acre of plant growth media.

In some embodiments, inoculant compositions of the present disclosure are applied in an amount sufficient to ensure the plant propagation materials are coated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores per kilogram of plant propagation material. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores are applied to each seed.

In some embodiments, inoculant compositions of the present disclosure are applied in an amount sufficient to ensure each plant is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores are applied to each plant.

In some embodiments, inoculant compositions of the present disclosure are applied in an amount sufficient to ensure each acre of treated crops is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores are applied to each acre of treated crops.

In some embodiments, inoculant compositions of the present disclosure are applied in an amount sufficient to ensure each acre of plant growth media is treated with about/at least $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores. According to some embodiments, one or more inoculant compositions of the present disclosure is/are applied in an amount sufficient to ensure that an average of about/at least $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ microbial cells/spores are applied to each acre of plant growth media.

Inoculant compositions of the present disclosure may be applied to plants, plant parts and/or plant growth media at any time, including, but not limited to, prior to planting, at the time of planting, after planting, prior to germination, at the time of germination, after germination, prior to seedling emergence, at the time of seedling emergence, after seedling emergence, prior to the vegetative stage, during the vegetative stage, after the vegetative stage, prior to the reproductive stage, during the reproductive stage, after the reproductive stage, prior to flowering, at the time of flowering, after flowering, prior to fruiting, at the time of fruiting, after fruiting, prior to ripening, at the time of ripening, and after ripening. In some embodiments, an inoculant composition of the present disclosure is applied to plant propagation materials (e.g., seeds) about/at least 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks prior to planting.

In some embodiments, an inoculant composition of the present disclosure is applied to plant propagation materials (e.g., seeds) at the time of planting.

In some embodiments, an inoculant composition of the present disclosure is applied to plant propagation materials (e.g., seeds) after planting but before germination.

In some embodiments, an inoculant composition of the present disclosure is applied to plants following emergence.

The present disclosure extends to plants and plant parts (e.g., coated plant propagation materials) that have been treated with an inoculant composition of the present disclosure, to plants that grow from plant parts (e.g., coated plant propagation materials) that have been treated with an inoculant composition of the present disclosure, to plant parts harvested from plants that have been treated with an inoculant composition of the present disclosure, to plant parts harvested from plants that grow from plant parts (e.g., coated plant propagation materials) that have been treated with an inoculant composition of the present disclosure, to processed products derived from plants that have been treated with an inoculant composition of the present disclosure, to processed products derived from plants that grow from plant parts (e.g., coated plant propagation materials) that have been treated with an inoculant composition of the present disclosure, to crops comprising a plurality of plants that have been treated with an inoculant composition of the present disclosure, and to crops comprising a plurality of plants that grow from plant parts (e.g., coated plant propagation materials) that have been treated with an inoculant composition of the present disclosure.

In some embodiments, the present disclosure provides coated plant propagation materials comprising, consisting essentially of, or consisting of a plant propagation material and a coating that covers at least a portion of the outer surface of the plant propagation material, said coating comprising, consisting essentially of, or consisting of an inoculant composition of the present disclosure.

In some embodiments, the coating comprises two, three, four, five or more layers. According to some embodiments, the coating comprises an inner layer that contains an inoculant composition of the present disclosure and one or more outer layers free or substantially free of microorganisms. In some embodiments, the coating comprises an inner layer that is an inoculant composition of the present disclosure and an outer layer that is equivalent to an inoculant composition of the present disclosure except that it does not contain microbial cells/spores.

In some embodiments, the coating comprises, consists essentially of, or consists of an inoculant composition of the present disclosure and a drying powder. Drying powders may be applied in any suitable amount(s)/concentration(s). The absolute value of the amount/concentration that is/are sufficient to cause the desired effect(s) may be affected by factors such as the type, size and volume of material to which the composition will be applied, the type(s) of microorganisms in the composition, the number of microorganisms in the composition, the stability of the microorganisms in the composition and storage conditions (e.g., temperature, relative humidity, duration). Those skilled in the art will understand how to select an effective amount/concentration using routine dose-response experiments after studying the present disclosure. Guidance for the selection of appropriate amounts/concentrations can be found, for example, in International Patent Application Nos. PCT/US2016/050529 and PCT/US2016/050647 and U.S. Provisional Patent Application Nos. 62/296,798; 62/271,857; 62/347,773; 62/343,217; 62/296,784; 62/271,873; 62/347,785; 62/347,794; and 62/347,805. In some embodiments, the drying powder is applied in an amount ranging from about 0.5 to about 10 grams of drying powder per kilogram of plant propagation material. For example, in some embodiments, about 0.5, 1, 1.25, 1.5, 1.75, 2, 2.25, 2.5, 2.75, 3, 3.25, 3.5, 3.75, 4, 4.25, 4.5, 4.75, 5, 5.5, 6, 6.5, 7, 7.5, 8, 8.5, 9, 9.5, 10 grams or more of drying powder (e.g., drying powder comprising magnesium stearate, magnesium sulfate, powdered milk, silica, and/or talc) is applied per kilogram of seed. In some embodiments, a drying powder comprising calcium stearate, attapulgite clay, montmorillonite clay, graphite, magnesium stearate, silica (e.g., fumed silica, hydrophobically-coated silica and/or precipitated silica) and/or talc is applied to seeds coated with an inoculant composition of the present disclosure at a rate of about 1, 1.25, 1.5, 1.75, 2, 2.25, 2.5, 2.75, or 3 grams per kilogram of seed.

In some embodiments, the coating completely covers the outer surface of the plant propagation material.

In some embodiments, the average thickness of the coating is at least 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 4, 4.5, 5 µm or more. In some embodiments, the average thickness of the coating is about 1.5 to about 3.0 µm.

The present disclosure extends to kits comprising, consisting essentially of, or consisting of one or more plants and/or plant parts (e.g., coated plant propagation materials) that have been treated with or an inoculant composition of the present disclosure and a container housing the treated plant(s) and/or plant part(s). In some embodiments, the kit further comprises one or more oxygen scavengers, such as activated carbon, ascorbic acid, iron powder, mixtures of ferrous carbonate and metal halide catalysts, sodium chloride and/or sodium hydrogen carbonate.

The container may comprise any suitable material(s), including, but not limited to, materials that reduce the amount of light, moisture and/or oxygen that contact the coated plant propagation material when the container is sealed. In some embodiments, the container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%. In some embodiments, the container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 $cm^3/m^2$ day (as measured in accordance with ASTM D3985).

In some embodiments, the container reduces the amount of ambient light, moisture and/or oxygen that reaches said coated plant propagation material by about 5, 10, 15, 20, 25, 30, 35, 40, 45, 50, 55, 60, 65, 70, 75, 80, 85, 90, 95 or 100% when sealed.

In some embodiments, kits of the present disclosure comprise 1, 2, 3, 4, 5 or more additional containers. The additional containers may comprise any suitable component(s) or composition(s), including, but not limited to, agriculturally beneficial microorganisms, biostimulants, drying agents, nutrients, oxidation control components and pesticides. Examples of agriculturally beneficial microorganisms, biostimulants, drying agents, nutrients, oxidation control components and pesticides that may be included in the additional containers are described above.

The present disclosure extends to animal feed compositions comprising, consisting essentially of or consisting of a food component and a microbial component, said microbial component comprising, consisting essentially of, or consisting of an inoculant composition of the present disclosure.

Animal feed compositions of the present disclosure may comprise any suitable food component, including, but not limited to, fodder (e.g., grains, hay, legumes, silage and/or straw) and forage (e.g., grass).

Animal feed compositions of the present disclosure may be fed to any suitable animal, including, but not limited to, farm animals, zoo animals, laboratory animals and/or companion animals. In some embodiments, the animal feed composition is formulated to meet the dietary needs of birds (e.g., chickens, ducks, quails and/or turkeys), bovids (e.g., antelopes, bison, cattle, gazelles, goats, impala, oxen, sheep and/or wildebeests), canines, cervids (e.g., caribou, deer, elk and/or moose), equines (e.g., donkeys, horses and/or zebras), felines, fish, pigs, rabbits, rodents (e.g., guinea pigs, hamsters, mice and/or rats) and the like.

The present disclosure extends to methods and uses for inoculant compositions of the present disclosure.

In some embodiments, methods and uses of the present disclosure comprise, consist essentially of or consist of applying an inoculant composition of the present disclosure to a plant or plant part (e.g., plant propagation material). As noted above, inoculant compositions of the present disclosure may be applied to any type of plant, to any part/portion of a plant, in any suitable manner, in any suitable amount(s)/concentration(s) and at any suitable time(s). According to some embodiments, methods and uses of the present disclosure comprise, consist essentially of or consist of applying an inoculant composition of the present disclosure to a monocotyledonous plant or plant part (e.g., a cereal or pseudocereal plant or plant part, optionally, barley, buckwheat, corn, millet, oats, *quinoa*, rice, rye, sorghum or wheat). According to some embodiments, methods and uses of the present disclosure comprise, consist essentially of or consist of applying an inoculant composition of the present disclosure to a dicotyledonous plant or plant part (e.g., a leguminous plant or plant part, optionally, alfalfa, beans, lentils, peas, peanuts or soybeans).

In some embodiments, methods and uses of the present disclosure comprise, consist essentially of or consist of applying an inoculant composition of the present disclosure to a plant growth medium. As noted above, inoculant compositions of the present disclosure may be applied to any plant growth medium, in any suitable manner, in any suitable amount(s)/concentration(s) and at any suitable time(s).

In some embodiments, methods and uses of the present disclosure comprise, consist essentially of or consist of introducing a plant or plant part (e.g., plant propagation material) that has been treated with an inoculant composition of the present disclosure into a plant growth medium (e.g., a soil). Such methods may further comprise introducing one or more nutrients (e.g., nitrogen and/or phosphorous) into the plant growth medium. Any suitable nutrient(s) may be added to the growth medium, including, but not limited to, rock phosphate, monoammonium phosphate, diammonium phosphate, monocalcium phosphate, super phosphate, triple super phosphate, ammonium polyphosphate, fertilizers comprising one or more phosphorus sources, and combinations thereof.

In some embodiments, methods and uses of the present disclosure comprise, consist essentially of or consist of growing a plant from a plant propagation material that has been treated with an inoculant composition of the present disclosure.

The present disclosure extends to methods of enhancing the stability and/or survival of microbial cells/spores in a composition, said methods comprising, consisting essentially of or consisting of adding one or more paraffin oils and/or waxes to said composition in an amount effective to enhance the stability and/or survival of microbial cells/spores therein.

Paraffin oils and/or waxes may be used to improve any suitable microbial stability characteristic(s) of the microbial cells/spores in a composition, including, but not limited to, the ability of the microbial cells/spores in a composition to enhance plant yield after being coated on a seed and stored for a defined period prior to planting the seed. For example, in some embodiments, the addition of one or more paraffin oils and/or waxes to a composition enhances the ability of the microbial cells/spores therein to propagate and increase yield after being coated on a plant propagation material (e.g., seed) and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more paraffin oils and/or waxes to a composition improves the stability of one or more microbial cells/spores therein by at least about 0.1, 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition (e.g., a control composition that is identical to the inoculant composition of the present disclosure except that it lacks one or more of the components found in the inoculant composition and/or contains one or more components not found in the inoculant composition of the present disclosure). For example, the addition of one or more paraffin oils and/or waxes to a composition may improve the survival rate of one or more of the microbial cells/spores contained therein by at least about 5, 10, 15, 20, 25, 30, 35, 40, 45, 50, 55, 60, 65, 70, 75, 80, 85, 90, 95, 100, 105, 110, 115, 120, 125, 150, 175, 200% or more as compared to a control composition that is identical to the inoculant composition except that lacks one or more paraffin oils and/or waxes and/or comprises a reduced amount one or more paraffin oils and/or waxes.

In some embodiments, the addition of one or more paraffin oils and/or waxes to a composition improves the survival of one or more of the microbial cells/spores in an inoculant composition to the extent that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of the microbial cells/spores survive when the inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the addition of one or more paraffin oils and/or waxes to a composition improves the survival of one or more of the microbial cells/spores in an inoculant composition to the extent that at least about 5, 6, 7, 8, 9, 10, 11, 12, 13, 14, 15, 16, 17, 18, 19, 20, 25, 30, 35, 40, 45, 50, 55, 60, 65, 70% or more of the microbial cells/spores survive when the inoculant composition is coated on a seed, dried and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more paraffin oils and/or waxes to a composition improves the survival of one or more of the microbial cells/spores in an inoculant composition to the extent that at least $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ cfu/seed or more of the microbial cells/spores survive when the inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more. In some embodiments, the addition of one or more paraffin oils and/or waxes to a composition improves the survival of one or more of the microbial cells/spores in an inoculant composition to the extent that at least $1 \times 10^1$, $1 \times 10^2$, $1 \times 10^3$, $1 \times 10^4$, $1 \times 10^5$, $1 \times 10^6$, $1 \times 10^7$ cfu/seed or more of the microbial cells/spores survive when the inoculant composition is coated on a seed and stored at 20, 21, 22, 23, 24, 25, 26, 27, 28, 29 and/or 30° C. and 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

In some embodiments, the addition of one or more paraffin oils and/or waxes to a composition improves both the survival rate and one, two, three, four, five, six, seven, eight, nine, ten or more microbial stability characteristics of the microbial spore(s) contained therein.

The absolute value of the amount/concentration/dosage of one or more paraffin oils and/or waxes that must be added to the composition to enhance the stability and/or survival of microbial cells/spores therein may be affected by factors such as the type, size and volume of the composition, the inherent stability of the microbial cells/spores in the composition, the identity and amounts/concentrations of other components in the inoculant composition (e.g., monosaccharides, disaccharides, sugar alcohols, oxidation control components) and the storage conditions (e.g., temperature, relative humidity, duration). Those skilled in the art will understand how to select an effective amount/concentration/dosage using routine dose-response experiments after studying the present disclosure.

In some embodiments, one or more of the paraffin oils and/or waxes is/are added to the composition until it comprises about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.5% or more (by weight) of said composition, optionally about 1 to about 99%, about 5 to about 95%, about 10 to about 95%, about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60% to about 95%, about 65% to about 95%, about 70 to about 95%, about 75 to about 95%, about 80 to about 95% or about 80 to about 95%, about 5 to about 90%, about 10 to about 90%, about 15 to about 90%, about 20 to about 90%, about 25 to about 90%, about 30 to about 90%, about 35 to about 90%, about 40 to about 90%, about 45 to about 90%, about 50 to about 90%, about 55 to about 90%, about 60% to about 90%, about 65% to about 90%, about 70 to about 90%, about 75 to about 90%, about 80 to about 90% or about 80 to about 90% (by weight) of said composition.

In some embodiments, a combination of two, three, four or more paraffin oils and/or waxes is added to the composition until it comprises about 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, 99.5% or more (by weight) of said composition, optionally about 1 to about 99%, about 5 to about 95%, about 10 to about 95%, about 15 to about 95%, about 20 to about 95%, about 25 to about 95%, about 30 to about 95%, about 35 to about 95%, about 40 to about 95%, about 45 to about 95%, about 50 to about 95%, about 55 to about 95%, about 60% to about 95%, about 65% to about 95%, about 70 to about 95%, about 75 to about 95%, about 80 to about 95% or about 80 to about 95%, about 5 to about 90%, about 10 to about 90%, about 15 to about 90%, about 20 to about 90%, about 25 to about 90%, about 30 to about 90%, about 35 to about 90%, about 40 to about 90%, about 45 to about 90%, about 50 to about 90%, about 55 to about 90%, about 60% to about 90%, about 65% to about 90%, about 70 to about 90%, about 75 to about 90%, about 80 to about 90% or about 80 to about 90% (by weight) of said composition.

Paraffin oils and/or waxes may be added to the composition in any suitable ratio(s). In some embodiments, two, three, four or more paraffin oils and/or waxes are added to the composition in one of the ratios described above with respect to inoculant compositions of the present disclosure.

In some embodiments, one or more paraffin oils and/or waxes is added to the composition in an amount/concentration sufficient to ensure microbial cells/spores remain viable therein following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, one or more paraffin oils and/or waxes is added to the composition in an amount/concentration sufficient to ensure at least 0.01, 0.05, 0.1, 0.5, 1, 2, 3, 4, 5, 10, 15, 20, 25, 30, 35, 40, 45, 50, 55, 60, 65, 70, 75, 80, 85, 90, 95% of the microbial cells/spores therein remain viable following:

storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, one or more paraffin oils and/or waxes is added to the composition in an amount/concentration sufficient to ensure at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$ or more colony-forming units of the microbial cells/spores therein remain viable per gram and/or milliliter of composition following: storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

desiccation by about 5, 10, 15, 20, 25, 30, 35, 40, 45, 50, 55, 60, 65, 70, 75, 80, 85, 90, 95% or more;

desiccation by about 5, 10, 15, 20, 25, 30, 35, 40, 45, 50, 55, 60, 65, 70, 75, 80, 85, 90, 95% or more and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

cryopreservation at or below −80° C. for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more;

application to plant propagation material (optionally, seed), optionally application to plant propagation material and desiccation by about 5, 10, 15, 20, 25, 30, 35, 40, 45, 50, 55, 60, 65, 70, 75, 80, 85, 90, 95% or more and/or application to a plant propagation material and storage at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 0, 5, 10, 15, 20, 25, 30, 35, 40, 45, 50, 55, 60, 65, 70, 75, 80, 85, 90, 95% or more relative humidity for a period of 1, 2, 3, 4, 5, 6, 7, 8, 9, 10, 11, 12, 13, 14, 15, 16, 17, 18, 19, 20, 21, 22, 23, 24, 28, 32, 36, 40, 44, 48, 52, 56, 60, 64, 68, 72, 76, 80, 84, 88, 92, 96, 100, 104 weeks or more; and/or foliar application, optionally foliar application and desiccation by about 5, 10, 15, 20, 25, 30, 35, 40, 45, 50, 55, 60, 65, 70, 75, 80, 85, 90, 95% or more and/or foliar application and exposure to temperatures of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and relative humidities of 0, 5, 10, 15, 20, 25, 30, 35, 40, 45, 50, 55, 60, 65, 70, 75, 80, 85, 90, 95% or more for a period of 0.1, 0.2, 0.25, 0.5, 0.75, 1, 1.5, 2, 2.5, 3, 3.5, 4, 4.5, 5, 6, 7, 8, 9, 10, 11, 12, 13, 14, 15, 16, 17, 18, 19, 20, 21 days or more.

In some embodiments, two, three, four or more paraffin oils and/or waxes are added to the composition in amounts/concentrations sufficient to synergistically enhance the stability and/or survival of the microbial cells/spores therein.

The present disclosure also provides systems and methods of using inoculant compositions of the present disclosure in conjunction with additional compositions comprising one or more agriculturally beneficial constituents. The additional composition(s) may comprise any suitable agriculturally beneficial constituent(s), including, but not limited to, the agriculturally beneficial constituents described above.

In some embodiments, inoculant compositions of the present disclosure are used in conjunction with one or more on-seed compositions, one or more in-furrow compositions and/or one or more foliar-applied compositions.

In some embodiments, inoculant compositions of the present disclosure are used as part of an integrated disease and/or pest management system.

Particular embodiments of the present disclosure are described in the following numbered paragraphs:

1. An inoculant composition, comprising, consisting essentially of, or consisting of: microbial cells/spores and a carrier that comprises, consists essentially of or consists of one or more paraffin oils and/or waxes.
2. The inoculant composition of any one of the preceding paragraphs, wherein said microbial cells/spores comprise about 0.1% to about 50% (by weight) of said inoculant composition, optionally about 5 to about 15% (by weight) of said composition, optionally about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% (by weight) of said inoculant composition.
3. The inoculant composition of any one of the preceding paragraphs, wherein said microbial cells/spores are present in said inoculant composition in a concentration ranging from about $1\times10^1$ to about $1\times10^{20}$ colony-forming units per gram and/or milliliter of said inoculant composition, optionally $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$ or more colony-forming units per gram and/or milliliter of said inoculant composition.
4. The inoculant composition of any one of the preceding paragraphs, wherein said microbial cells/spores comprise, consist essentially of, or consist of spores of one or more diazotrophic microorganisms.
5. The inoculant composition of any one of the preceding paragraphs, wherein said microbial cells/spores comprise, consist essentially of, or consist of spores of one or more strains of *Bacillus*, optionally one or more strains of *Bacillus circulans, Bacillus licheniformis, Bacillus macerans, Bacillus megaterium, Bacillus polymyxa* and/or *Bacillus pumilus*.

6. The inoculant composition of any one of the preceding paragraphs, wherein said microbial cells/spores comprise, consist essentially of, or consist of spores of one or more phosphate-solubilizing microorganisms.

7. The inoculant composition of any one of the preceding paragraphs, wherein said microbial cells/spores comprise, consist essentially of, or consist of spores of one or more strains of *Penicillium*, optionally one or more strains of *P. bilaiae* and/or *P. gaestrivorus*.

8. The inoculant composition of any one of the preceding paragraphs, wherein said microbial cells/spores comprise, consist essentially of, or consist of spores of one or more strains of *Trichoderma*, optionally one or more strains of T. asperellum, T. atroviride, T fertile, T. gamsii, *T. hamatum, T. harzianum, T. reesi, T. virens* and/or T. viridae.

9. The inoculant composition of any one of the preceding paragraphs, wherein said microbial cells/spores comprise, consist essentially of, or consist of spores of one or more mycorrhizal fungi.

10. The inoculant composition of any one of the preceding paragraphs, wherein said microbial cells/spores comprise, consist essentially of, or consist of spores of one or more strains of *Gliocladium*, optionally one or more strains of *Gliocladium virens*, one or more strains of *Glomus*, optionally one or more strains of *Glomus intraradices*, and/or one or more strains of Metarhizium, optionally, one or more strains of Metarhizium anisopliae.

11. The inoculant composition of any one of the preceding paragraphs, wherein said microbial cells/spores comprise, consist essentially of, or consist of spores of one or more strains of *Bacillus*, optionally *B. amyloliquefaciens* D747, *B. amyloliquefaciens* NRRL B-50349, *B. amyloliquefaciens* TJ1000, *B. amyloliquefaciens* FZB24, *B. amyloliquefaciens* FZB42, *B. amyloliquefaciens* IN937a, *B. amyloliquefaciens* IT-45, *B. amyloliquefaciens* Ti1000, *B. amyloliquefaciens* MB1600, *B. amyloliquefaciens* BS27 (deposited as NRRL B-5015), *B. amyloliquefaciens* BS2084 (deposited as NRRL B-50013), *B. amyloliquefaciens* 15AP4 (deposited as ATCC PTA-6507), *B. amyloliquefaciens* 3AP4 (deposited as ATCC PTA-6506), *B. amyloliquefaciens* LSSA01 (deposited as NRRL B-50104), *B. amyloliquefaciens* ABP278 (deposited as NRRL B-50634), *B. amyloliquefaciens* 1013 (deposited as NRRL B-50509), *B. amyloliquefaciens* 918 (deposited as NRRL B-50508), *B. amyloliquefaciens* 22CP1 (deposited as ATCC PTA-6508) and *B. amyloliquefaciens* BS18 (deposited as NRRL B-50633), *B. cereus* I-1562, *B. firmus* I-1582, B. lichenformis BA842 (deposited as NRRL B-50516), B. lichenformis BL21 (deposited as NRRL B-50134), *B. mycoides* NRRL B-21664, *B. pumilus* NRRL B-21662, *B. pumilus* NRRL B-30087, *B. pumilus* ATCC 55608, *B. pumilus* ATCC 55609, *B. pumilus* GB34, *B. pumilus* KFP9F, *B. pumilus* QST 2808, *B. subtilis* ATCC 55078, *B. subtilis* ATCC 55079, *B. subtilis* MBI 600, *B. subtilis* NRRL B-21661, *B. subtilis* NRRL B-21665, *B. subtilis* CX-9060, *B. subtilis* GB03, *B. subtilis* GB07, *B. subtilis* QST-713, *B. subtilis* FZB24, *B. subtilis* D747, *B. subtilis* 3BP5 (deposited as NRRL B-50510), *B. thuringiensis* ATCC 13367, *B. thuringiensis* GC-91, *B. thuringiensis* NRRL B-21619, *B. thuringiensis* ABTS-1857, *B. thuringiensis* SAN 401 I, *B. thuringiensis* ABG-6305, *B. thuringiensis* ABG-6346, *B. thuringiensis* AM65-52, *B. thuringiensis* SA-12, *B. thuringiensis* SB4, *B. thuringiensis* ABTS-351, *B. thuringiensis* HD-1, *B. thuringiensis* EG 2348, *B. thuringiensis* EG 7826, Bacil B. lus *thuringiensis* EG 7841, *B. thuringiensis* DSM 2803, *B. thuringiensis* NB-125 and/or *B. thuringiensis* NB-176.

12. The inoculant composition of any one of the preceding paragraphs, wherein said microbial cells/spores comprise, consist essentially of, or consist of spores of one or more strains of *Gliocladium*, optionally *G. virens* ATCC 52045 and/or *G. virens* GL-21, one or more strains of *Glomus*, optionally *G. intraradices* RTI-801, one or more strains of Metarhizium, optionally M. anisopliae F52, *Penicillium*, optionally *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* NRRL 67154, *P. bilaiae* NRRL 67155, *P. bilaiae* NRRL 67156, *P. bilaiae* NRRL 67157, *P. bilaiae* NRRL 67158, *P. bilaiae* NRRL 67159, *P. bilaiae* RS7B-SD1, P. brevicompactun AgRF 18, *P. canescens* ATCC 10419, *P. expansum* ATCC 24692, *P. expansum* YT02, P. fellatanum ATCC 48694, P. gaestrivorus NRRL 50170, *P. glabrum* DAOM 239074, *P. glabrum* CBS 229.28, *P. janthinellum* ATCC 10455, P. lanosocoeruleum ATCC 48919, P. *radicum* ATCC 201836, P. *radicum* FRR 4717, P. *radicum* FRR 4719, P. *radicum* N93/47267 and/or P. raistrickii ATCC 10490, and/or one or more strains of *Trichoderma*, optionally T. asperellum SKT-1, T. asperellum ICC 012, T. atroviride LC52, T. atroviride CNCM 1-1237, T. fertile JM41R, T. gamsii ICC 080, *T. hamatum* ATCC 52198, *T. harzianum* ATCC 52445, *T. harzianum* KRL-AG2, *T. harzianum* T-22, *T. harzianum* TH-35, *T. harzianum* T-39, *T. harzianum* ICCO12, T. reesi ATCC 28217, *T virens* ATCC 57678, *T. virens* G1-3, T. *virens* GL-21, *T. virens* G-41, T. viridae ATCC 52440, T. viridae ICC080 and/or T. viridae TV1.

13. The inoculant composition of any one of the preceding paragraphs, wherein said microbial cells/spores comprise, consist essentially of, or consist of spores of one or more strains having a genomic sequence that is at least 75, 80, 85, 90, 95, 96, 97, 98, 99% or more identical to any of the strains recited in paragraph 11 on the basis of 16S rDNA sequence identity.

14. The inoculant composition of any one of the preceding paragraphs, wherein said microbial cells/spores comprise, consist essentially of, or consist of spores of one or more strains having a genomic sequence that is at least 75, 80, 85, 90, 95, 96, 97, 98, 99% or more identical to any of the strains recited in paragraph 12 on the basis of internal transcribed spacer (ITS) and/or cytochrome c oxidase (CO1) sequence identity.

15. The inoculant composition of any one of the preceding paragraphs, wherein said microbial cells/spores comprises, consists essentially of, or consists of spores of one or more biopesticides, optionally one or more biofungicides, one or more bioinsecticides and/or one or more bionematicides.

16. The inoculant composition of any one of the preceding paragraphs, wherein said carrier comprises about 50 to about 99% (by weight) of said inoculant composition, optionally about 75 to about 95% (by weight) of said composition, optionally about 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5 or 90% (by weight) of said inoculant composition.
17. The inoculant composition of any one of the preceding paragraphs, wherein said carrier comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5%, 0.55%, 0.6%, 0.65%, 0.7%, 0.75%, 0.8%. 0.85%, 0.9%, 0.95% or 1% water by weight, based upon the total weight of the composition.
18. The inoculant composition of any one of the preceding paragraphs, wherein said carrier comprises no water.
19. The inoculant composition of any one of the preceding paragraphs, wherein said carrier comprises, consists essentially of or consists of a seed- and/or soil-compatible carrier.
20. The inoculant composition of any one of the preceding paragraphs, wherein said carrier further comprises one or more oils, optionally one or more mineral oils, nut oils and/or vegetable oils.
21. The inoculant composition of any one of the preceding paragraphs, wherein said carrier further comprises one or more PEGs, optionally PEG 200, PEG 300 and/or PEG 400.
22. The inoculant composition of any one of the preceding paragraphs, wherein said carrier further comprises one or more PPGs, optionally PPG-9, PPG-10, PPG-17, PPG-20 and/or PPG-26.
23. The inoculant composition of any one of the preceding paragraphs, further comprising one or more stabilizing compounds.
24. The inoculant composition of paragraph 23, wherein said one or more stabilizing compounds comprise about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.
25. The inoculant composition of any one of paragraphs 23-24, wherein said one or more stabilizing compounds comprises one or more hygroscopic polymers, optionally one or more albumins, alginates, celluloses, gums (e.g., cellulose gum, guar gum, gum arabic, gum combretum, xanthan gum), methyl celluloses, nylons, pectins, polyacrylic acids, polycarbonates, PEGs, PEIs, polylactides, PMAs, polyurethanes, PVAs, PVPs, propylene glycols, sodium carboxymethyl celluloses and/or starches.
26. The inoculant composition of any one of paragraphs 23-25, wherein said one or more stabilizing compounds comprises one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid), one or more oxygen scavengers, optionally ascorbic acid and/or sodium hydrogen carbonate, and/or one or more film-forming agents, optionally PVP/VA.
27. The inoculant composition of any one of the preceding paragraphs, further comprising one or more dispersants, optionally one or more of the dispersants expressly set forth above.
28. The inoculant composition of paragraph 27, wherein said one or more dispersants comprise about 0.01 to about 5% (by weight) of said composition, optionally about 0.1 to about 5% (by weight) of said composition, optionally about 0.1, 0.2, 0.3, 0.4, 0.5, 0.6, 0.7, 0.8, 0.9, 1, 1.5, 2, 2.5, 3, 3.5, 4, 4.5 or 5% (by weight) of said composition.
29. The inoculant composition of any one of the preceding paragraphs, further comprising one or more pesticides, optionally one or more of the acaricides, fungicides, herbicides, insecticides and/or nematicides expressly set forth above.
30. The inoculant composition of any one of the preceding paragraphs, further comprising one or more LCOs, optionally one or more LCOs represented by formulas I-IV.
31. The inoculant composition of any one of paragraphs 1-29, further comprising one or more LCOs, optionally one or more of the LCOs represented by structures V-XXXIII.
32. The inoculant composition of any one of the preceding paragraphs, further comprising one or more chitin oligosaccharides, optionally one or more chitin oligosaccharides represented by formulas XXXIV-XXXV.
33. The inoculant composition of any one of paragraphs 1-31, further comprising one or more chitin oligosaccharides, optionally one or more chitin oligosaccharides represented by structures XXXVI-LXXXIII.
34. The inoculant composition of any one of the preceding paragraphs, further comprising one or more chitinous compounds, optionally one or more chitins and/or one or more chitosans.
35. The inoculant composition of any one of the preceding paragraphs, further comprising one or more flavonoids, optionally one or more of the anthocyanidins, anthoxanthins, flavanones, flavanonols, isoflavonoids, neoflavonoids, and/or pterocarpans expressly set forth above.
36. The inoculant composition of any one of the preceding paragraphs, further comprising jasmonic acid and/or one or more derivatives thereof.
37. The inoculant composition of any one of the preceding paragraphs, further comprising linoleic acid and/or one or more derivatives thereof.
38. The inoculant composition of any one of the preceding paragraphs, further comprising linolenic acid and/or one or more derivatives thereof.
39. The inoculant composition of any one of the preceding paragraphs, further comprising one or more karrakins, optionally one or more karrakins represented by formula LXXXIV.
40. The inoculant composition of any one of the preceding paragraphs, further comprising one or more biostimulants, optionally one or more seaweed extracts, one or more humic acids, one or more fulvic acids, myo-inositol and/or glycine.
41. The inoculant composition of any one of the preceding paragraphs, further comprising one or more microbial extracts, optionally one or more extracts from media comprising one or more diazotrophic, phosphophosphate-solubilizing and/or biopesticidal microorganisms.

42. The inoculant composition of any one of the preceding paragraphs, further comprising one or more nutrients, optionally one or more vitamins (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin $B_{12}$, choline) vitamin C, vitamin D, vitamin E, vitamin K, carotenoids ($\alpha$-carotene, $\beta$-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine).

43. The inoculant composition of any one of the preceding paragraphs, further comprising one or more anti-freezing agents, optionally ethylene glycol, glycerin, propylene glycol and/or urea.

44. The inoculant composition of any one of the preceding paragraphs, wherein said inoculant composition comprises a trace amount of water.

45. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial cells/spores remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

46. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial cells/spores remain viable when said inoculant composition is coated on a plant propagation material.

47. The inoculant composition of any one of the preceding paragraphs, wherein at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said one or more microbial cells/spores remain viable when said inoculant composition is coated on a plant propagation material and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

48. The inoculant composition of any one of the preceding paragraphs, wherein at least about $1\times10^1$ to about $1\times10^{10}$ colony-forming units of said one or more microbial cells/spores per gram and/or milliliter of said inoculant composition remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1\times10^4$, $1\times10^5$, $1\times10^6$, $1\times10^7$ or more colony-forming units per gram and/or milliliter of said inoculant composition.

49. The inoculant composition of any one of the preceding paragraphs, wherein at least about $1\times10^1$ to about $1\times10^{10}$ colony-forming units of said one or more microbial cells/spores per seed remain viable when said inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 5, 10, 15, 20, 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^4$, $1\times10^5$, $1\times10^6$, $1\times10^7$ or more colony-forming units per seed.

50. A coated plant propagation material, comprising, consisting essentially of, or consisting of: a plant propagation material; and a coating that covers at least a portion of an outer surface of said seed, said coating comprising, consisting essentially of, or consisting of the inoculant composition of any one of claims 1-49.

51. The coated plant propagation material paragraph 50, wherein said coating comprises, consists essentially of, or consists of an inner coating layer that comprises said microbial cells/spores and an outer coating layer that is devoid of said microbial cells/spores.

52. The coated plant propagation material of any one of paragraphs 50-51, wherein said coating comprises about $1\times10^1$ to about $1\times10^{15}$ colony-forming units of said microbial cells/spores, optionally $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units.

53. The coated plant propagation material any one of paragraphs 50-52, wherein said plant propagation material is a seed.

54. The coated plant propagation material of paragraph 53, wherein said seed is a monocot.

55. The coated plant propagation material of paragraph 53, wherein said seed is a dicot.

56. The coated plant propagation material of paragraph 53, wherein said seed is leguminous.

57. The coated plant propagation material of paragraph 53, wherein said seed is non-leguminous.

58. The coated plant propagation material of any one of paragraphs 50-53, wherein said plant propagation material is of the family Amaranthaceae, optionally chard, spinach, sugar beet, or *quinoa*.

59. The coated plant propagation material of any one of paragraphs 50-53, wherein said plant propagation material is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.

60. The coated plant propagation material of any one of paragraphs 50-53, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*.

61. The coated plant propagation material of any one of paragraphs 50-53, wherein said plant propagation material is of the family Cucurbitaceae, optionally cantaloupe, cucumber, honeydew, melon, pumpkin, squash (e.g., acorn squash, butternut squash, summer squash), watermelon, or zucchini.

62. The coated plant propagation material of any one of paragraphs 50-53, wherein said plant propagation material is of the family Fabaceae, optionally alfalfa, beans, carob, clover, guar, lentils, mesquite, peas, peanuts, soybeans, tamarind, tragacanth, or vetch.

63. The coated plant propagation material of any one of paragraphs 50-53, wherein said plant propagation material is of the family Malvaceae, optionally cacao, cotton, durian, hibiscus, kenaf, kola, or okra.

64. The coated plant propagation material of any one of paragraphs 50-53, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat.

65. The coated plant propagation material of any one of paragraphs 50-53, wherein said plant propagation material is of the family Polygonaceae, optionally buckwheat.

66. The coated plant propagation material of any one of paragraphs 50-53, wherein said plant propagation material is of the family Rosaceae, optionally almonds, apples, apricots, blackberry, blueberry, cherries, peaches, plums, quinces, raspberries, roses, or strawberries.

67. The coated plant propagation material of any one of paragraphs 50-53, wherein said plant propagation material is of the family Solanaceae, optionally bell peppers, chili peppers, eggplant, *petunia*, potato, tobacco, or tomato.

68. The coated plant propagation material of any one of paragraphs 50-53, wherein said plant propagation material is of the family Vitaceae, optionally grape.

69. A kit, comprising: the coated plant propagation material of any one of paragraphs 50-68; and a container housing said coated plant propagation material.

70. The kit of claim 69, wherein said container reduces the amount of ambient light that reaches said coated plant propagation material by about 5, 10, 15, 20, 25, 30, 35, 40, 45, 50, 55, 60, 65, 70, 75, 80, 85, 90, 95 or 100% when sealed.

71. The kit of any one of paragraphs 69-70, wherein said container reduces the amount of ambient oxygen that reaches said plant propagation material by about 5, 10, 15, 20, 25, 30, 35, 40, 45, 50, 55, 60, 65, 70, 75, 80, 85, 90, 95 or 100% when sealed.

72. The kit of any one of paragraphs 69-71, wherein said container comprises, consists essentially of, or consists of a material having light permeability of less than about 1, 2, 3, 4, 5, 6, 7, 8, 9, 10, 15, 20, 25, 30, 35, 40, 45, 50, 55, 60, 65, 70 or 75%.

73. The kit of any one of paragraphs 69-72, wherein said container comprises, consists essentially of, or consists of a material having an oxygen transmission rate of less than about 5, 10, 15, 20, 25, 30, 35, 40, 45, 50, 60, 70, 80, 90, 100, 125, 150, 175, 200, 225, 250, 275, 300, 325, 350, 375, 400, 425, 450, 475, or 500 cm$^3$/m$^2$ day (as measured in accordance with ASTM D3985).

74. The kit of any one of paragraphs 69-73, wherein said kit further comprises one or more oxygen-absorbing compounds, optionally activated carbon, iron powder, sodium chloride, ferrous carbonate, one or more metal halide catalysts and/or sodium hydrogen carbonate.

75. A plant treated with the inoculant composition of any one of paragraphs 1-49.

76. A plant germinated from the coated plant propagation material of any one of paragraphs 50-68.

77. A plant part harvested from the plant of any one of paragraphs 75-76.

78. A processed product produced from the plant part of paragraph 77.

79. A crop comprising, consisting essentially of, or consisting of a plurality of the plant or plant part of any one of paragraphs 75-77.

80. A method, comprising, consisting essentially of, or consisting of: applying the inoculant composition of any one of paragraphs 1-49 to a plant propagation material.

81. The method of paragraph 80, further comprising planting said plant propagation material in a growth medium, optionally soil.

82. The method of paragraph 81, wherein said plant propagation material is planted in soil in which plants of the same genus were cultivated in at least one of the three years prior to said planting, optionally in each of the one, two or three years immediately preceding said planting.

83. The method of any one of paragraphs 80-82, wherein said inoculant composition is applied to the plant propagation material at the time of planting.

84. The method of any one of paragraphs 80-82, wherein said inoculant composition is applied to the plant propagation material at least 1, 2, 3, 4, 5, 6, 7, 8, 9, 10, 11, 12, 15, 18, 21, 24, 27, 30, 33, 36, 39, 42, 45, 48 hours or more prior to planting.

85. The method of any one of paragraphs 80-82, wherein said inoculant composition is applied to the plant propagation material at least 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more prior to planting.

86. The method of any one of paragraphs 80-82, wherein said inoculant composition is applied to the plant propagation material about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 months or more prior to planting 87. The method of any one of paragraphs 80-86, wherein said plant propagation material is a seed.

88. The method of any one of paragraphs 80-87, wherein said plant propagation material is a monocot.

89. The method of any one of paragraphs 80-87, wherein said plant propagation material is a dicot.

90. The method of any one of paragraphs 80-87, wherein said plant propagation material is leguminous.

91. The method of any one of paragraphs 80-87, wherein said plant propagation material is non-leguminous.

92. The method of any one of paragraphs 80-87, wherein said plant propagation material is of the family Amaranthaceae, optionally chard, spinach, sugar beet, or *quinoa*.

93. The method of any one of paragraphs 80-87, wherein said plant propagation material is of the family Asteraceae, optionally artichoke, asters, chamomile, chicory, chrysanthemums, dahlias, daisies, *echinacea*, goldenrod, guayule, lettuce, marigolds, safflower, sunflowers, or zinnias.
94. The method of any one of paragraphs 80-87, wherein said plant propagation material is of the family Brassicaceae, optionally arugula, broccoli, bok choy, Brussels sprouts, cabbage, cauliflower, canola, collard greens, daikon, garden cress, horseradish, kale, mustard, radish, rapeseed, rutabaga, turnip, wasabi, watercress, or *Arabidopsis thaliana*.
95. The method of any one of paragraphs 80-87, wherein said plant propagation material is of the family Cucurbitaceae, optionally cantaloupe, cucumber, honeydew, melon, pumpkin, squash (e.g., acorn squash, butternut squash, summer squash), watermelon, or zucchini.
96. The method of any one of paragraphs 80-87, wherein said plant propagation material is of the family Fabaceae, optionally alfalfa, beans, carob, clover, guar, lentils, mesquite, peas, peanuts, soybeans, tamarind, tragacanth, or vetch.
97. The method of any one of paragraphs 80-87, wherein said plant propagation material is of the family Malvaceae, optionally cacao, cotton, durian, hibiscus, kenaf, kola, or okra.
98. The method of any one of paragraphs 80-87, wherein said plant propagation material is of the family Poaceae, optionally bamboo, barley, corn, fonio, lawn grass (e.g., Bahia grass, Bermudagrass, bluegrass, Buffalograss, Centipede grass, Fescue, or *Zoysia*), millet, oats, ornamental grasses, rice, rye, sorghum, sugar cane, triticale, or wheat.
99. The method of any one of paragraphs 80-87, wherein said plant propagation material is of the family Polygonaceae, optionally buckwheat.
100. The method of any one of paragraphs 80-87, wherein said plant propagation material is of the family Rosaceae, optionally almonds, apples, apricots, blackberry, blueberry, cherries, peaches, plums, quinces, raspberries, roses, or strawberries.
101. The method of any one of paragraphs 80-87, wherein said plant propagation material is of the family Solanaceae, optionally bell peppers, chili peppers, eggplant, *petunia*, potato, tobacco, or tomato.
102. The method of any one of paragraphs 80-87, wherein plant propagation material seed is of the family Vitaceae, optionally grape.
103. A method comprising, consisting essentially of, or consisting of: planting the coated plant propagation material of any one of paragraphs 50-68 in a growth medium, optionally soil.
104. The method of any one of paragraphs 80-103, further comprising applying the inoculant composition of any one of paragraphs 1-49 to the plant that grows from the plant propagation material.
105. A method of enhancing the stability and/or survivability of one or more microorganisms in a composition that comprises one or more paraffin oils and/or waxes, said method comprising, consisting essentially of, or consisting of: adding one or more stabilizing compounds to said composition.
106. The method of paragraph 105, wherein said one or more stabilizing compounds comprises, consists essentially of, or consists of:
one or more hygroscopic polymers, optionally one or more albumins, alginates, celluloses, gums (e.g., cellulose gum, guar gum, gum arabic, gum combretum, xanthan gum), methyl celluloses, nylons, pectins, polyacrylic acids, polycarbonates, PEGs, PEIs, polylactides, PMAs, polyurethanes, PVAs, PVPs, propylene glycols, sodium carboxymethyl celluloses and/or starches; and/or
oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid), one or more oxygen scavengers, optionally ascorbic acid and/or sodium hydrogen carbonate, and/or one or more film-forming agents, optionally PVP/VA.
107. The method of any one of paragraphs 105-106, wherein said one or more stabilizing compounds is added until it comprises about 0.0001 to about 10% (by weight) of said composition, optionally about 2 to about 6% (by weight) of said composition, optionally about 0.0005, 0.001, 0.002, 0.003, 0.004, 0.005, 0.0075, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 1, 1.5, 2, 2.5, 3, 3.5, 4, 4.5, 5, 5.5, 6, 7, 7.5, 8, 8.5, 9, 9.5 or 10% (by weight) of said composition.
108. The method of any one of paragraphs 105-107, wherein said one or more stabilizing compounds is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial cells/spores remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.
109. The method of any one of paragraphs 105-108, wherein said one or more stabilizing compounds is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial cells/spores remain viable when said inoculant composition is coated on a plant propagation material.
110. The method of any one of paragraphs 105-109, wherein said one or more stabilizing compounds is added in an amount sufficient to ensure that at least about 0.01, 0.05, 0.1, 0.5, 1, 2, 3, 4, 5, 10, 15, 20, 25, 30, 35, 40, 45, 50, 55, 60, 65, 70, 75, 80, 85, 90, 95% or more of said microbial cells/spores remain viable when said inoculant composition is coated on a plant propagation material and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more.

111. The method of any one of paragraphs 105-110, wherein said one or more stabilizing compounds is added in an amount sufficient to ensure that at least about $1\times10^1$ to about $1\times10^{15}$ colony-forming units of said microbial cells/spores per gram and/or milliliter of said inoculant composition remain viable when said inoculant composition is stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally at least $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$ or more colony-forming units per gram and/or milliliter of said inoculant composition.

112. The method of any one of paragraphs 105-111, wherein said one or more stabilizing compound is added in an amount sufficient to ensure that at least about $1\times10^1$ to about $1\times10^1$s colony-forming units of said microbial cells/spores per seed remain viable when said inoculant composition is coated on a seed and stored at 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40° C. and 25, 30, 35, 40, 45, 50, 55, 60, 65, 70, 75, 80, 85% or more relative humidity for a period of 1, 2, 3, 4, 5, 6, 7, 8, 9, 10, 11, 12, 13, 14, 15, 16, 17, 18, 20, 21, 22, 23, 24, 28, 32, 36, 40, 44, 48, 52, 56, 60, 64, 68, 72, 76, 80, 84, 88, 92, 96, 100, 104 weeks or more, optionally $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, or more colony-forming units per seed.

113. The method of any of paragraphs 105-112, further comprising adding one or more dispersants to said composition.

114. The method of paragraph 113, wherein said one or more dispersants comprises one or more anionic surfactants, optionally one or more of the anionic surfactants expressly set forth above; one or more cationic surfactants, optionally one or more of the cationic surfactants expressly set forth above; one or more non-ionic surfactants, optionally one or more of the non-ionic surfactants expressly set forth above; and/or one or more wetting agents, optionally one or more of the wetting agents expressly set forth above.

115. The inoculant composition of any one of paragraphs 113-114, wherein said one or more dispersants comprises one or more polyoxyethylene alkyl ethers, one or more acrylic copolymers, one or more polyoxyethylene sorbitan trioleates and/or one or more secondary alcohol ethoxylates.

116. The method of any one of claims 105-115, further comprising adding one or more non-aqueous microbial extracts to said composition.

117. The method of paragraph 116, wherein said one or more non-aqueous microbial extracts comprises:

one or more *Bacillus* extracts, optionally an extract of media comprising *B. amyloliquefaciens* D747, *B. amyloliquefaciens* NRRL B-50349, *B. amyloliquefaciens* TJ1000, *B. amyloliquefaciens* FZB24, *B. amyloliquefaciens* FZB42, *B. amyloliquefaciens* IN937a, *B. amyloliquefaciens* IT-45, *B. amyloliquefaciens* TJ1000, *B. amyloliquefaciens* MBI600, *B. amyloliquefaciens* BS27 (deposited as NRRL B-5015), *B. amyloliquefaciens* BS2084 (deposited as NRRL B-50013), *B. amyloliquefaciens* 15AP4 (deposited as ATCC PTA-6507), *B. amyloliquefaciens* 3AP4 (deposited as ATCC PTA-6506), *B. amyloliquefaciens* LSSA01 (deposited as NRRL B-50104), *B. amyloliquefaciens* ABP278 (deposited as NRRL B-50634), *B. amyloliquefaciens* 1013 (deposited as NRRL B-50509), *B. amyloliquefaciens* 918 (deposited as NRRL B-50508), *B. amyloliquefaciens* 22CP1 (deposited as ATCC PTA-6508) and *B. amyloliquefaciens* BS18 (deposited as NRRL B-50633), *B. cereus* I-1562, *B. firmus* I-1582, B. lichen formis BA842 (deposited as NRRL B-50516), B. lichenformis BL21 (deposited as NRRL B-50134), *B. mycoides* NRRL B-21664, *B. pumilus* NRRL B-21662, *B. pumilus* NRRL B-30087, *B. pumilus* ATCC 55608, *B. pumilus* ATCC 55609, *B. pumilus* GB34, *B. pumilus* KFP9F, *B. pumilus* QST 2808, *B. subtilis* ATCC 55078, *B. subtilis* ATCC 55079, *B. subtilis* MBI 600, *B. subtilis* NRRL B-21661, *B. subtilis* NRRL B-21665, *B. subtilis* CX-9060, *B. subtilis* GB03, *B. subtilis* GB07, *B. subtilis* QST-713, *B. subtilis* FZB24, *B. subtilis* D747, *B. subtilis* 3BP5 (deposited as NRRL B-50510), *B. thuringiensis* ATCC 13367, *B. thuringiensis* GC-91, *B. thuringiensis* NRRL B-21619, *B. thuringiensis* ABTS-1857, *B. thuringiensis* SAN 401 I, *B. thuringiensis* ABG-6305, *B. thuringiensis* ABG-6346, *B. thuringiensis* AM65-52, *B. thuringiensis* SA-12, *B. thuringiensis* SB4, *B. thuringiensis* ABTS-351, *B. thuringiensis* HD-1, *B. thuringiensis* EG 2348, *B. thuringiensis* EG 7826, *B. thuringiensis* EG 7841, *B. thuringiensis* DSM 2803, *B. thuringiensis* NB-125 and/or *B. thuringiensis* NB-176;

one or more *Bradyrhizobium* extracts, optionally an extract of media comprising *B. elkanii* SEMIA 501, *B. elkanii* SEMIA 587, *B. elkanii* SEMIA 5019, *B. japonicum* NRRL B-50586 (also deposited as NRRL B-59565), *B. japonicum* NRRL B-50587 (also deposited as NRRL B-59566), *B. japonicum* NRRL B-50588 (also deposited as NRRL B-59567), *B. japonicum* NRRL B-50589 (also deposited as NRRL B-59568), *B. japonicum* NRRL B-50590 (also deposited as NRRL B-59569), *B. japonicum* NRRL B-50591 (also deposited as NRRL B-59570), *B. japonicum* NRRL B-50592 (also deposited as NRRL B-59571), *B. japonicum* NRRL B-50593 (also deposited as NRRL B-59572), *B. japonicum* NRRL B-50594 (also deposited as NRRL B-50493), *B. japonicum* NRRL B-50608, *B. japonicum* NRRL B-50609, *B. japonicum* NRRL B-50610, *B. japonicum* NRRL B-5061 I, *B. japonicum* NRRL B-50612, *B. japonicum* NRRL B-50726, *B. japonicum* NRRL B-50727, *B. japonicum* NRRL B-50728, *B. japonicum* NRRL B-50729, *B. japonicum* NRRL B-50730, *B. japonicum* SEMIA 566, *B. japonicum* SEMIA 5079, *B. japonicum* SEMIA 5080, *B. japonicum* USDA 6, *B. japonicum* USDA 110, *B. japonicum* USDA 122, *B. japonicum* USDA 123, *B. japonicum* USDA 127, *B. japonicum* USDA 129 and/or *B. japonicum* USDA 532C;

one or more *Rhizobium* extracts, optionally an extract of media comprising *R. leguminosarum* SOl2A-2;

one or more *Sinorhizobium* extracts, optionally an extract of media comprising *S. fredii* CCBAU114 and/or *S. fredii* USDA 205;

one or more *Penicillium* extracts, optionally an extract of media comprising *P. bilaiae* ATCC 18309, *P. bilaiae* ATCC 20851, *P. bilaiae* ATCC 22348, *P. bilaiae* NRRL 50162, *P. bilaiae* NRRL 50169, *P. bilaiae* NRRL 50776, *P. bilaiae* NRRL 50777, *P. bilaiae* NRRL 50778, *P. bilaiae* NRRL 50777, *P. bilaiae* NRRL 50778, *P. bilaiae* NRRL 50779, *P. bilaiae* NRRL 50780, *P. bilaiae* NRRL 50781, *P. bilaiae* NRRL 50782, *P. bilaiae* NRRL 50783, *P. bilaiae* NRRL 50784, *P. bilaiae* NRRL 50785, *P. bilaiae* NRRL 50786, *P. bilaiae* NRRL 50787, *P. bilaiae* NRRL 50788, *P. bilaiae* RS7B-SD1, P. brevicompactum AgRF18, *P. canescens* ATCC 10419, *P. expansum* ATCC 24692, *P. expansum* YT02, P. fellatanum ATCC 48694, P. gaestrivorus NRRL 50170, *P. glabrum* DAOM 239074, *P. glabrum* CBS 229.28, *P. janthinellum* ATCC 10455, P. lanosocoeruleum ATCC 48919, P. *radicum* ATCC 201836, P. *radicum* FRR 4717, P. *radicum* FRR 4719, P. *radicum* $N_{93/47267}$ and/or P. raistrickii ATCC 10490; one or more *Streptomyces* extracts, optionally an extract of media comprising *Streptomyces* NRRL B-30145, *Streptomyces* M1064, *S. galbus* NRRL 30232, S, *lydicus* WYEC 108 (ATCC 55445), *S. violaceusniger* YCED 9 (ATCC 55660) and/or *Streptomyces* WYE 53 (ATCC 55750); and/or one or more *Trichoderma* extracts, optionally an extract of media comprising T. asperellum SKT-1 (ECO-HOPE®, Kumiai Chemical Industry Co., Ltd., Japan), T atroviride LC52 (SENTINEL®, Agrimm Technologies Ltd, NZ), *T. harzianum* T-22 (PLANTSHIELD®, der *Firma* BioWorks Inc., USA), *T. harzianum* TH-35 (ROOT PRO®, from Mycontrol Ltd., Israel), *T. harzianum* T-39 (TRICHODEX®, Mycontrol Ltd., Israel; T. 2000®, Makhteshim Ltd., Israel), *T. harzianum* ICC012 and *T. viride* TRICHOPEL (Agrimm Technologies Ltd, NZ), *T harzianum* ICC012 and *T viride* ICC080 (REMEDIER® WP, Isagro Ricerca, Italy), *T. polysporum* and *T. harzianum* (BINAB®, BINAB Bio-Innovation AB, Sweden), T. stromaticum TRICO-VAB® (C.E.P.L.A.C., Brazil), *T. virens* GL-21 (SOIL-GARD®, Certis LLC, USA), *T. virens* G 1-3, ATCC 57678, *T. virens* G 1-21 (Thermo Trilogy Corporation, Wasco, CA), *T. virens* G1-3 and *Bacillus amyloliquefaciens* FZB2, *T. virens* G1-3 and *Bacillus amyloliquefaciens* NRRL B-50349, *T. virens* G1-3 and *Bacillus amyloliquefaciens* TJ1000, *T. virens* G1-21 and *Bacillus amyloliquefaciens* FZB24, *T. virens* G1-21 and *Bacillus amyloliquefaciens* NRRL B-50349, *T. virens* G1-21 and *Bacillus amyloliquefaciens* TJ1000, *T. viride* TRIECO® (Ecosense Labs. (India) Pvt. Ltd., Indien, BIO-CURE® F from T. Stanes & Co. Ltd., Indien), *T. viride* TV 1 (Agribiotec sri, Italy), *T. viride* ICC080.

118. The inoculant composition of any one of paragraphs 116-117, wherein said one or more non-aqueous microbial extracts comprises less than 0.01, 0.02, 0.03, 0.04, 0.05, 0.06, 0.07, 0.08, 0.09, 0.1, 0.15, 0.2, 0.25, 0.3, 0.35, 0.4, 0.45, 0.5% water by weight, based upon the total weight of the composition.

119. The method of any one of paragraphs 116-118, wherein said one or more non-aqueous microbial extracts is added until it comprises about 0.1 to about 5% (by weight) of said composition, optionally about 0.1 to about 2% (by weight) of said composition, optionally about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4., 4.5, 4.6, 4.7, 4.8, 4.9, 5% or more (by weight) of said composition.

120. A method, comprising, consisting essentially of or consisting of applying the inoculant composition of any one of paragraphs 1-49 and a second composition to a seed and/or to the plant that grows from said seed, said second composition comprising:

one or more agriculturally beneficial microorganisms, optionally one or more diazotrophs, one or more phosphate-solubilizing microorganisms, one or more mycorrhizal fungi and/or one or more biopesticides, optionally one or more biofungicides, one or more bioinsecticides and/or one or more bionematicides;

one or more biostimulants, optionally one or more seaweed extracts, one or more humic acids, one or more fulvic acids, myo-inositol and/or glycine;

one or more nutrients, optionally one or more vitamins (e.g., vitamin A, vitamin B complex (i.e., vitamin $B_1$, vitamin $B_2$, vitamin $B_3$, vitamin $B_5$, vitamin $B_6$, vitamin $B_7$, vitamin $B_8$, vitamin $B_9$, vitamin B 12, choline) vitamin C, vitamin D, vitamin E, vitamin K, carotenoids (α-carotene, α-carotene, cryptoxanthin, lutein, lycopene and/or zeaxanthin), macrominerals (e.g., calcium, iron, magnesium, nitrogen, phosphorous, potassium and/or sodium), trace minerals (e.g., boron, cobalt, chloride, chromium, copper, fluoride, iodine, iron, manganese, molybdenum, selenium and/or zinc) and/or organic acids (e.g., acetic acid, citric acid, lactic acid, malic acid and/or taurine);

one or more acaricides, optionally one or more of the acaricides expressly set forth above;

one or more fungicides, optionally one or more of the fungicides expressly set forth above;

one or more herbicides, optionally one or more of the herbicides expressly set forth above;

one or more insecticides, optionally one or more of the insecticides expressly set forth above;

one or more nematicides, optionally one or more of the nematicides expressly set forth above;

one or more LCOs, optionally one or more of the LCOs represented by formulas I-IV and/or one or more of the LCOs represented by structures V-XXXIII;

one or more chitooligosaccharides, optionally one or more of the chitin oligosaccharides represented by formulas XXXIV-XXXV and/or one or more of the chitin oligosaccharides represented by structures XXXVI-LXXXIII, one or more chitinous compounds, optionally one or more chitins and/or one or more chitosans;

one or more flavonoids, optionally one or more of the anthocyanidins, anthoxanthins, flavanones, flavanonols, isoflavonoids, neoflavonoids, and/or pterocarpans expressly set forth above;

jasmonic acid and/or one or more derivatives thereof;

linoleic acid and/or one or more derivatives thereof;

linolenic acid and/or one or more derivatives thereof;

one or more karrakins, optionally one or more karrakins represented by formula LXXXIV;

gluconolactone; and/or one or more oxidation control components, optionally one or more antioxidants (e.g., ascorbic acid, ascorbyl palmitate, ascorbyl stearate, calcium ascorbate, one or more carotenoids, lipoic acid, one or more phenolic compounds (e.g., one or more flavonoids, flavones and/or flavonols), potassium ascorbate, sodium ascorbate, one or more thiols (e.g., glutathione, lipoic acid and/or N-acetyl cysteine), one or more tocopherols, one or more tocotrienols, ubiquinone and/or uric acid)

and/or one or more oxygen scavengers, optionally ascorbic acid and/or sodium hydrogen carbonate.

EXAMPLES

The following examples are not intended to be a detailed catalogue of all the different ways in which the present disclosure may be implemented or of all the features that may be added to the present disclosure. Subjects skilled in the art will appreciate that numerous variations and additions to the various embodiments may be made without departing from the present disclosure. Hence, the following descriptions are intended to illustrate some particular embodiments of the invention and not to exhaustively specify all permutations, combinations and variations thereof.

Example 1

Paraffin Oil Enhances *Penicillium* Survival

Liquid inoculant compositions comprising *P. bilaiae* spores were prepared as set forth in Table I and coated on corn seeds pretreated with a commercially available pesticide. Control seeds were prepared using a commercially available *P. bilaiae* inoculant in accordance with the manufacturers specifications. The coated seeds were stored at 30° C. and 65% relative humidity for 0, 29 or 75 days and then assayed for on-seed survivability. The survivability of *P. bilaiae* spores was enhanced in each of the SUN AG® 7N compositions. FIG. 1.

TABLE 1

*P. bilaiae* spores in a liquid composition comprising SUN AG ® 7N (95% w/w) + ATLOX ™ 4912 (5% w/w)
*P. bilaiae* spores in a liquid composition comprising SUN AG ® 7N (85% w/w) + ATLOX ™ 4912 (5% w/w) + tung oil (10% w/w)
*P. bilaiae* spores in a liquid composition comprising SUN AG ® 7N (90% w/w) + SUNWAX ™ DP 116 (10% w/w)
*P. bilaiae* spores in a liquid composition comprising SUN AG ® 7N (80% w/w) + SUNWAX ™ DP 116 (10% w/w) + tung oil (10% w/w)
*P. bilaiae* spores in a liquid composition comprising SUN AG ® 7N (88% w/w) + SUNWAX ™ DP 116 (10% w/w) + SiO$_2$ (2% w/w)
*P. bilaiae* spores in a liquid composition comprising SUN AG ® 7N (78% w/w) + SUNWAX ™ DP 116 (10% w/w) + SiO$_2$ (2% w/w) + tung oil (10% w/w)

Example 2

Paraffin Wax Enhances *Penicillium* Survival

Figure 2:
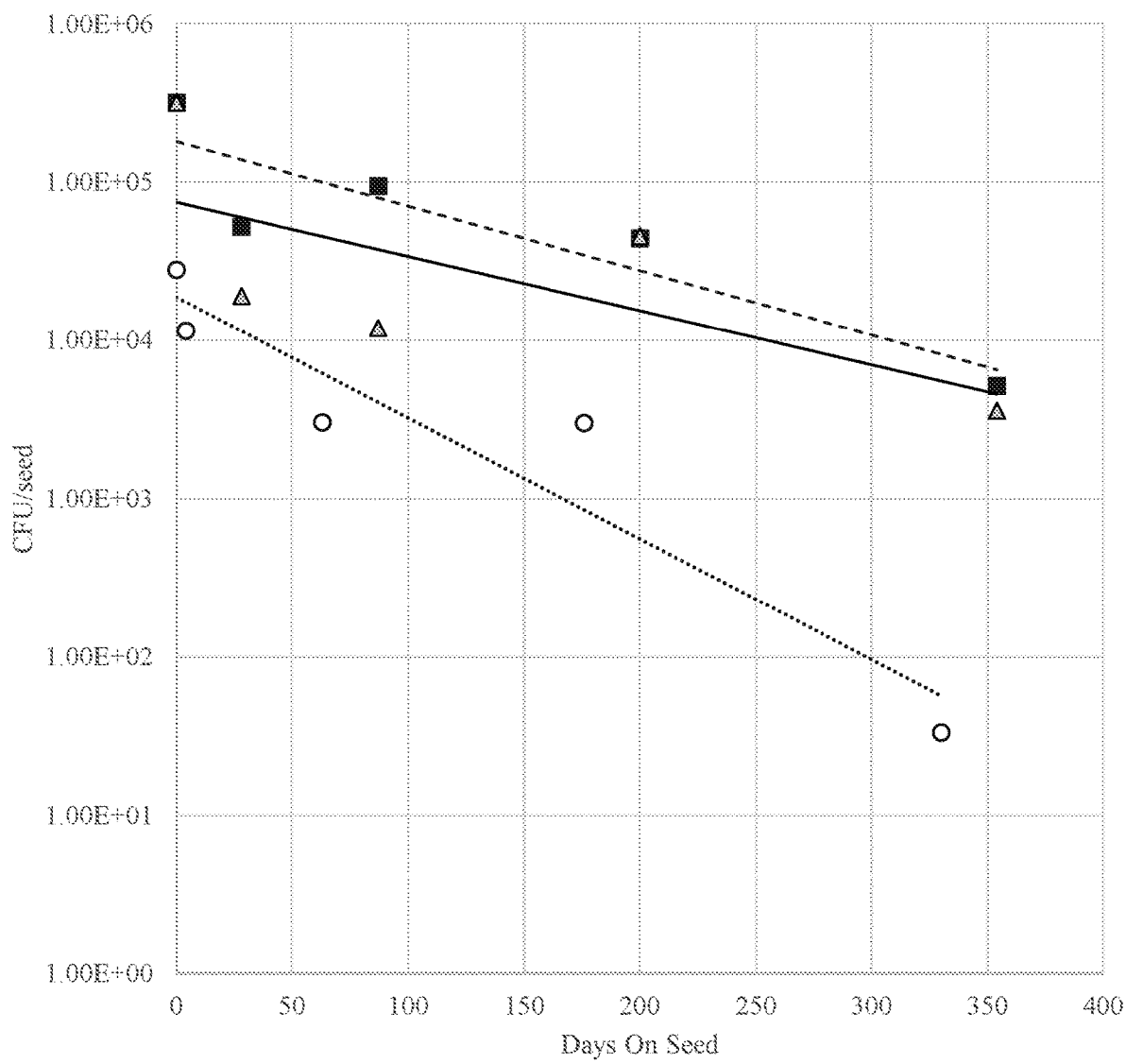
FIG. 2 is a graph showing the on-seed survivability of P. bilaiae spores at 10° C. and 50% relative humidity in SUN AG® 7N (black squares, dashed black trend line) or SUN AG® 7N supplemented with tung oil (gray triangles, solid black trend line), as compared to a commercially available inoculant comprising P. bilaiae spores (white diamonds, dotted black trend line).

Liquid inoculant compositions comprising *P. bilaiae* spores (10% w/w) and ATLOX™ 4912 (4.5% w/w) in SUN AG® 7N (85.5% w/w) or SUN AG® 7N (76.5% w/w) supplemented with tung oil (9% w/w) were coated on corn seeds pretreated with a commercially available pesticide. Control seeds were prepared using a commercially available *P. bilaiae* inoculant in accordance with the manufacturers specifications. The coated seeds were stored at 10° C. and 50% relative humidity for up to 354 days and then assayed for on-seed survivability. The survivability of *P. bilaiae* spores was enhanced in each of the SUN AG® 7N compositions. FIG. 2.

Example 3

Paraffin Wax Enhances *Penicillium* Survival

Liquid inoculant compositions comprising *P. bilaiae* spores (10% w/w) and ATLOX™ 4912 (4.5% w/w) in SUN AG® 7N (85.5% w/w) or SUN AG® 7N (76.5% w/w) supplemented with tong oil (9% w/w) were coated on corn seeds pretreated with a commercially available pesticide. Control seeds were prepared using a commercially available *P. bilaiae* inoculant in accordance with the manufacturers specifications. The coated seeds were stored at 25° C. and 65% relative humidity for up to 354 days and then assayed for on-seed survivability. The survivability of *P. bilaiae* spores was enhanced in each of the SUN AG® 7N compositions.

Example 4

Paraffin Oil Enhances *Bradyrhizobium* Survival

Inoculant compositions are prepared by combining 0.5 g spray dried *Bradyrhizobium japonicum* with 9.5 g of a formulation comprising SUN AG® 7N, SUN AG® 7N (85, 90 or 95% w/w) and ATLOX™ 4912 (15, 10 or 5% w/w), SUN AG® 7N (85, 90 or 95% w/w) and tung oil (15, 10 or 5% w/w), or SUN AG® 7N (80 or 90% w/w) and ATLOX™ 4912 (10 or 5% w/w) and tung oil (10 or 5% w/w). Comparative formulations containing spray dried *Bradyrhizobium japonicum* without the paraffin oil are also prepared. The formulations are sealed in containers and stored at 10, 20 or 30° C. and 50% relative humidity for up to 365 days. Bradyrhizzobium *japonicum* survival is enhanced by each of the paraffin oil formulations.

Example 5

Paraffin Wax Enhances *Bradyrhizobium* Survival

Inoculant compositions are prepared by combining 0.5 g spray dried *Bradyrhizobium japonicum* with 9.5 g of a formulation comprising SUNWAX™ DP 116, SUNWAX™ DP 116 (85, 90 or 95% w/w) and ATLOX™ 4912 (15, 10 or 5% w/w), SUNWAX™ DP 116 (85, 90 or 95% w/w) and tung oil (15, 10 or 5% w/w), or SUNWAX™ DP 116 (80 or 90% w/w) and ATLOX™ 4912 (10 or 5% w/w) and tung oil (10 or 5% w/w). Comparative formulations containing spray dried *Bradyrhizobium japonicum* without the paraffin wax are also prepared. The formulations are sealed in containers and stored at 10, or 30° C. and 50% relative humidity for up to 365 days. Bradyrhizzobiumjaponicum survival is enhanced by each of the paraffin wax formulations.

Example 6

Paraffin Oil Enhances *Pseudomonas* Survival

Inoculant compositions are prepared by combining 0.5 g spray dried *Pseudomonas fluorescens* with 9.5 g of a formulation comprising SUN AG® 7N, SUN AG® 7N (85, 90 or 95% w/w) and ATLOX™ 4912 (15, 10 or 5% w/w), SUN AG® 7N (85, 90 or 95% w/w) and tung oil (15, 10 or 5% w/w), or SUN AG® 7N (80 or 90% w/w) and ATLOX™ 4912 (10 or 5% w/w) and tung oil (10 or 5% w/w). Comparative formulations containing spray dried *Pseudomonas fluorescens* without the paraffin oil are also prepared. The formulations are sealed in containers and stored at 10, 20 or 30° C. and 50% relative humidity for up to 365 days. *Pseudomonas fluorescens* survival is enhanced by each of the paraffin oil formulations.

Example 7

Paraffin Wax Enhances *Pseudomonas* Survival

Inoculant compositions are prepared by combining spray dried *Pseudomonas fluorescens* with SUNWAX™ DP 116, SUNWAX™ DP 116 (85, 90 or 95% w/w) and ATLOX™ 4912 (15, 10 or 5% w/w), SUNWAX™ DP 116 (85, 90 or 95% w/w) and tung oil (15, 10 or 5% w/w), or SUNWAX™ DP 116 (80 or 90% w/w) and ATLOX™ 4912 (10 or 5% w/w) and tung oil (10 or 5% w/w). Comparative formulations containing spray dried *Pseudomonas fluorescens* without the paraffin wax are also prepared. The formulations are sealed in containers and stored at 10, 20 or 30° C. and 50% relative humidity for up to 365 days. *Pseudomonas fluorescens* survival is enhanced by each of the paraffin wax formulations.

Example 8

Paraffin Oil Enhances *Bacillus* Survival

Inoculant compositions are prepared by combining 1 g of *B. pumilus* spores with 9 g of a composition comprising SUN AG® 7N, SUN AG® 7N (85, 90 or 95% w/w) and ATLOX™ 4912 (15, 10 or 5% w/w), SUN AG® 7N (85, 90 or 95% w/w) and tung oil (15, 10 or 5% w/w), or SUN AG® 7N (80 or 90% w/w) and ATLOX™ 4912 (10 or 5% w/w) and tung oil (10 or 5% w/w). Comparative formulations containing *B. pumilus* spores without the paraffin oil are also prepared. The formulations are applied to PARAFILM® discs (2.5 cm diameter) at room temperature (20-23° C.) and ambient humidity under ambient light (five 2 l drops per disc). Treated discs are dried at room temperature under ambient humidity and ambient light and then assayed for survivability. Treated discs are stored at 10, 20 or 30° C. and 32%, 54%, 65%, 75% or 100% relative humidity under ambient light for up to 3 days and then assayed for survivability. *B. pumilus* survival is enhanced by each of the paraffin oil formulations.

Example 9

Paraffin Wax Enhances *Bacillus* Survival

Inoculant compositions are prepared by combining 1 g of *B. pumilus* spores with 9 g of a composition comprising SUNWAX™ DP 116, SUNWAX™ DP 116 (85, 90 or 95% w/w) and ATLOX™ 4912 (15, 10 or 5% w/w), SUNWAX™ DP 116 (85, 90 or 95% w/w) and tung oil (15, 10 or 5% w/w), or SUNWAX™ DP 116 (80 or 90% w/w) and ATLOX™ 4912 (10 or 5% w/w) and tung oil (10 or 5% w/w). Comparative formulations containing *B. pumilus* spores without the paraffin wax are also prepared. The formulations are applied to PARAFILM® discs (2.5 cm diameter) at room temperature (20-23° C.) and ambient humidity under ambient light (five 2 µl drops per disc). Treated discs are dried at room temperature under ambient humidity and ambient light and then assayed for survivability. Treated discs are stored at 10, 20 or 30° C. and 32%, 54%, 65%, 75% or 100% relative humidity under ambient light for up to 3 days and then assayed for survivability. *B. pumilus* survival is enhanced by each of the paraffin oil formulations.

Example 8

Paraffin Oil Enhances *Yersinia* Survival

Inoculant compositions are prepared by combining 1 g of a *Yersinia* entomaphaga fermentate with 9 g of a composition comprising SUN AG® 7N, SUN AG® 7N (85, 90 or 95% w/w) and ATLOX™ 4912 (15, 10 or 5% w/w), SUN AG® 7N (85, 90 or 95% w/w) and tung oil (15, 10 or 5% w/w), or SUN AG® 7N (80 or 90% w/w) and ATLOX™ 4912 (10 or 5% w/w) and tung oil (10 or 5% w/w). Comparative formulations containing *Yersinia* entomaphaga fermentate without the paraffin oil are also prepared. The formulations are applied to PARAFILM® discs (2.5 cm diameter) at room temperature (20-23° C.) and ambient humidity under ambient light (five 2 µl drops per disc). Treated discs are dried at room temperature under ambient humidity and ambient light and then assayed for survivability. Treated discs are stored at 10, 20 or 30° C. and 32%, 54%, 65%, 75% or 100% relative humidity under ambient light for up to 3 days and then assayed for survivability. *Yersinia* survival is enhanced by each of the paraffin oil formulations.

Example 9

Paraffin Wax Enhances *Yersinia* Survival

Inoculant compositions are prepared by combining 1 g of a *Yersinia* entomaphaga fermentate with 9 g of a composition comprising SUNWAX™ DP 116, SUNWAX™ DP 116 (85, 90 or 95% w/w) and ATLOX™ 4912 (15, 10 or 5% w/w), SUNWAX™ DP 116 (85, 90 or 95% w/w) and tung oil (15, 10 or 5% w/w), or SUNWAX™ DP 116 (80 or 90% w/w) and ATLOX™ 4912 (10 or 5% w/w) and tung oil (10 or 5% w/w). Comparative formulations containing *Yersinia* entomaphaga fermentate without the paraffin wax are also prepared. The formulations are applied to PARAFILM® discs (2.5 cm diameter) at room temperature (20-23° C.) and ambient humidity under ambient light (five 2 µl drops per disc). Treated discs are dried at room temperature under ambient humidity and ambient light and then assayed for survivability. Treated discs are stored at 10, 20 or 30° C. and 32%, 54%, 65%, 75% or 100% relative humidity under ambient light for up to 3 days and then assayed for survivability. *Yersinia* survival is enhanced by each of the paraffin oil formulations.

Appendix A

*Acinetobacter*, Actinomycetes. Aegerita, *Agrobacterium* (e.g., *A. radiobacter* strains such as K1026 and K84), Akanthomyces, *Alcaligenes, Alternaria*, Aminobacter (e.g., *A. aganoensis, A. aminovorans, A. anthyllidis, A. ciceronei, A. lissarensis, A. niigataensis*), *Ampelomyces* (e.g., *A. quisqualis* strains such as M-10), *Anabaena* (e.g., *A. aequalis, A. affinis, A. angstumalis angstumalis, A. angstumalis marchita, A. aphanizomendoides, A. azollae, A. bornetiana, A. catenula, A. cedrorum, A. circinalis, A. confervoides, A. constricta, A. cyanobacterium, A. cycadeae, A. cylindrica, A. echinispora, A. felisii, A. fos-aquae fos-aquae, A. fos-aquae minor, A. flos-aquae treleasei, A. helicoidea, A. inaequalis, A. lapponica, A. laxa, A. lemmermannii, A. levanderi, A. limnetica, A. macrospora macrospora, A. macrospora robusta, A. monticulosa, A. nostoc, A. ascillarioides, A. planctonica, A. raciborski, A. scheremetievi, A. sphaerica, A. spiroides crassa, A. spiroides* spreoides, *A. subcylindrica*,

*A. torulosa, A. unispora, A. variabilis, A. verrucosa, A. viguieri, A. wisconsinense, A. zierlingii*), Arthrobacter, Arthrobotrys (e.g., *A. aggregata, A. alaskana*, A. ameropora, A. *anomala*, A. apscheronica, A. arthrobotryoides, A. *azerbaijanica*, A. bakunika, A. botryospora, A. brochopaga, A. chazarica, A. *chilensis*, A. cladodes, A. calvispora, *A. compacta*, A. conoides, A. constringens, *A. cylindrospora, A. dactyloides*, A. defectans, A. dendroides, A. doliiformis, A. *drechsleri, A. elegans*, A. ellipsospora, A. entomopaga, *A. ferox*, A. foliicola, A. *fruticulosa*, A. globospora. A. hatospora, A. hertziana, *A. indica, A. irregularis, A. javanica*, A. kirghizica, A. *longa*, A. longiphora, A. longiramulifera, A. longispora, A. mangrovispora, A. megaspora, A. mnicroscaphoides, A. *microspora*, A. multisecundaria, A. musiformis, A. nematopaga, A. nonseptata, A. oligospora, A. oudemansii, A. *oviformis*, A. perpasta, A. *polycephala*, A. pseudoclavata, A. pyriformis, A. *recta, A. robusta, A. rosea, A. scaphoides*, A. sclerohypha, A. shahriari, A. shizishanna, *A. sinensis*, A. soprunovii. A. stilbacea, A. straminicola, A. superba, A. tabrizica, A. *venusta*, A. vermicola, A. *yunnanensis*), Aschersonia, Ascophaera, *Aspergillus* (e.g., *A. flavus* strains such as NRRL 21882, *A. parasiticus*), Aulosira (e.g., A. aenigmatica, *A. africana*, A. bohemensis, A. bombayensis, A. confluens, A. fertilissima, A. fertilissma var. tenius, A. fritschii, A. godoyana, A. implexa, *A. laxa*, A. plantomca, A. prolifica, A. pseuodoramosa, A. schauinslandii, A. *striata, A. terrestris, A. thermalis*), Aureobacterium, *Aureobasidium* (e.g., *A. pullulans* strains such as DSM 14940 and DSM 14941), Azobacter, *Azorhizobium* (e.g., *A. caulinodans, A. doebereinerae, A. oxalatiphilum*), Azospirillum (e.g., A. amazonense strains such as BR 11140 (SpY2T), A. brasilense strains such as INTA Az-39, AZ39, XOH, BR 11002, BR 11005, Ab-V5 and Ab-V6, A. canadense, A. doebereinerae, A.*formosense*, A. halopraeferans, A. irakense, A. largimobile, A. lipoferum strains such as BR 11646, A. melinis, A. oryzae, A. picis, A. rugosum, A. thiophilum, A. zeae), Azotobacter (e.g., *A. agilis, A. armeniacus*, A. sp. AR, *A. beijerinckii, A. chroococcum*, A. DCU26, A. FA8, *A. nigricans, A. paspali, A. salinestris, A. tropicalis, A. vinelandii*), Bacillus (e.g., *B. amyloliquefaciens* strains such as D747, NRRL B-50349, TJ1000 (also known as 1BE, isolate ATCC BAA-390), FZB24, FZB42, IN937a, IT-45, TJ1000, MBI600, BS27 (deposited as NRRL B-5015), BS2084 (deposited as NRRL B-50013), 15AP4 (deposited as ATCC PTA-6507), 3AP4 (deposited as ATCC PTA-6506), LSSA01 (deposited as NRRL B-50104), ABP278 (deposited as NRRL B-50634), 1013 (deposited as NRRL B-50509), 918 (deposited as NRRL B-50508), 22CP 1 (deposited as ATCC PTA-6508) and BS18 (deposited as NRRL B-50633), *B. cereus* strains such as 1-1562, *B. firmus* strains such as 1-1582, *B. laevolacticus*, B. lichenformis strains such as BA842 (deposited as NRRL B-50516) and BL21 (deposited as NRRL B-50134), B. macerns, *B. firmus, B. mycoides* strains such as NRRL B-21664, *B. pasteurii, B. pumilus* strains such as NRRL B-21662, NRRL B-30087, ATCC 55608, ATCC 55609, GB34, KFP9F and QST 2808, *B. sphaericus, B. subtilis* strains such as ATCC 55078, ATCC 55079, MBI 600, NRRL B-21661, NRRL B-21665, CX-9060, GB03, GB07, QST 713, FZB24, D747 and 3BP5 (deposited as NRRL B-50510), *B. thuringiensis* strains such as ATCC 13367, GC-91, NRRL B-21619, ABTS-1857, SAN 401 I, ABG-6305, ABG-6346, AM65-52, SA-12, SB4, ABTS-351, HD-1, EG 2348, EG 7826, EG 7841, DSM 2803, NB-125 and NB-176), *Beijerinckia, Beauveria* (e.g., *B. bassiana* strains such as ATCC 26851, ATCC 48023, ATCC 48585, ATCC 74040, ATCC-74250, DSM 12256 and PPRI 5339), *Beijerinckia*, Blastodendrion, Bosea (e.g., B.

eneae, B. *lathyri*, *B. lupini*, *B. massiliensis*, B. minatitlaneneae, B. robiniae, B. thiooxidans, B. vestrisii), *Bradyrhizobium* (e.g., *B. arachidis, B. bete, B. canariense, B. cvtisi, B. daqingense, B. denitrificans, B. diazoefficiens, B. elkanii* strains such as SEMIA 501, SEMIA 587 and SEMIA 5019, *B. ganzhouense, B. huanghuauhaiense, B. icense, B. ingae, B. iriomotense, B. japonicum* strains such as NRRL B-50586 (also deposited as NRRL B-59565), NRRL B-50587 (also deposited as NRRL B-59566), NRRL B-50588 (also deposited as NRRL B-59567), NRRL B-50589 (also deposited as NRRL B-59568), NRRL B-50590 (also deposited as NRRL B-59569), NRRL B-50591 (also deposited as NRRL B-59570), NRRL B-50592 (also deposited as NRRL B-59571), NRRL B-50593 (also deposited as NRRL B-59572), NRRL B-50594 (also deposited as NRRL B-50493), NRRL B-50608, NRRL B-50609, NRRL B-50610, NRRL B-50611, NRRL B-50612, NRRL B-50726, NRRL B-50727, NRRL B-50728, NRRL B-50729, NRRL B-50730, SEMIA 566, SEMIA 5079, SEMIA 5080, USDA 6, USDA 110, USDA 122, USDA 123, USDA 127, USDA 129 and USDA 532C, B. *jicamae, B. lablabi, B. liaoningense, B. manausense, B. neotropicale, B. oligotrophicum, B. ottawaense, B. pachyrhizi, B. paxilaeri, B. retamae, B. rifense, B. valentinum, B. yuanmingense*), *Burkholderia* (e.g., *B. acidipaludis, B. ambifaria, B. andropogonis, B. anthina, B. arboris, B. bannensis, B. bryophila, B. caledonica, B. caribensis, B. caryophylli, B. cenocepacua, B. choica, B. cocovenenans, B. contaminans, B. denitrificans, B. diazotrophica, B. diffusa, B. dilworthii, B. dolosa, B. eburnea, B. endofungorum, B. ferrariae, B. fungorum, B. ginsengisoli, B. gladioli, B. glathei, B. glunae, B. graminis, B. grimmiae, B. heleia, B. hospital, B. humi, B. kururiensis, B. lata, B. latens, B. mallei, B. megapolitana, B. metallica, B. mimosarum, B. multivorans, B. nodosa, B. norimbergensis, B. oklahomensis, B. phenazinium, B. phenoliruptrix, B. phvmatum, B. phytofirmans, B. pickettii*, B. p/antarii, *B. pseudomallei, B. pseudomultivorans, B. pyrrocinia, B. rhizoxinica, B. rhynchosiae, B. sabiae, B. sacchari, B. sartisoli, B. sediminicola, B. seminalis, B. silvatlantica, B. singaporensis, B. soli*, B. sordidcola, B. sp. strains such as A396, *B. sprentiae, B. stabilis, B. symbiotica, B. telluris, B. terrae, B. terrestris, B. terricola, B. thailandensis, B. tropica, B. tuberum*, Bubonensis, *B. udeis, B. unamae*, B. vandii, *B. vietnamiensis, B. xenovorans, B. zhejiangensis*), *Brevibacillus, Burkholderia* (e.g., B. sp. A396 nov. rinojensis NRRL B-50319), Calonectria, *Candida* (e.g., *C. oleophila* such 1-182, *C. saitoana*), Candidatus (e.g., *C. Burkholderia* calva, *C. Burkholderia crenata*, *C. Burkholderia* hispidae, *C. Burkholderia* kirkii, *C. Burkholderia* mamillata, *C. Burkholderia* nigropunctata, *C. Burkholderia* rigidae, *C. Burkholderia* schumannianae, *C. Burkholderia* verschuerenii, *C. Burkholderia virens*, C. Phytoplasma allocasuarinae, C. Phytoplasma *americanum*, C. Phytoplasma asteris, C. Phytoplasma aurantifolia, C. Phytoplasma *australiense*, C. Phytoplasma balanitae, C. Phytoplasma brasiliense, C. Phytoplasma *caricae*, C. Phytoplasma castaneae, C. Phytoplasma cocosnigeriae, C. Phytoplasma cocostanzaniae, C. Phytoplasma convolvuli, C. Phytoplasma costaricanum, C. Phytoplasma cynodontis, C. Phytoplasma *fragariae*, C. Phytoplasma f-axini, C. Phytoplasma *graminis*, C. Phytoplasma *japonicum*, C. Phytoplasma luffae, C. Phytoplasma *lycopersici*, C. Phytoplasma malasianum, C. Phytoplasma *mali*, C. Phytoplasma omanense, C. Phytoplasma *oryzae*, C. Phytoplasma palmae, C. Phytoplasma *palmicola*, C. Phytoplasma phoenicium, C. Phytoplasma *pini*, C. Phytoplasma *pruni*, C. Phytoplasma prunorum, C. Phytoplasma pyri, C. Phytoplasma rhamni, C. Phytoplasma *rubi*, C. Phytoplasma solani, C. Phytoplasma spartii, C. Phytoplasma sudamericanum, C. Phytoplasma tamaricis, C. Phytoplasma *trifolii*, C. Phytoplasma *ulmi*, C. Phytoplasma *vitis*, C. Phytoplasma ziziphi), Chromobacterium (e.g., C. subtsugae NRRL B-30655 and PRAA4-1, C. vaccinia strains such as NRRL B-50880, C. *violaceum*), Chryseomonas, Clavibacter, Clonostachys (e.g., C. *rosea* f. *catenulata* (also referred to as *Gliocladium catenulatum*) strains such as J1446), Clostridium, Coelemomyces, Coelomycidium, *Colletotrichum* (e.g., C. *gloeosporioides* strains such as ATCC 52634), Comomonas, Conidiobolus, *Coniothyrium* (e.g., C. *minitans* strains such as CON/M/91-08), Cordyceps, Corynebacterium, Couchia, Cyphonectria (e.g., C. *parasitica*), *Cryptococcus* (e.g., C. *albidus*), Cryptophlebia (e.g., C. leucotreta), Culicinomyces, *Cupriavidus* (e.g., C. *alkaliphilus*, C. *basilensis*, C. *campinensis*, C. *gilardii*, C. *laharis*, C. *metallidurans*, C. *numazuensis*, C. *oxalaticus*, C. *pampae*, C. *pauculus*, C. *pinatubonensis*, C. *respiraculi*, C. *taiwanensis*), Curtobacterium, *Cydia* (e.g., C. *pomonella* strains such as V03 and V22), Dactvlaria (e.g., D. *candida*), Delftia (e.g., D. acidovorans strains such as RAY209), Desulforibtio, Desulfovibrio, Devosia (e.g., D. neptuniae), Dilophosphora (e.g., D. alopecuri), Engyodontium, Enterobacter, Entomophaga, Entomophthora, Erynia, *Escherichia* (e.g., *E. intermedia*), Eupenicillium, Exiguobacaterium, Filariomyces, Filobasidiella, *Flavobacterium* (e.g., F. H492 NRRL B-50584), Frankia (e.g., *F. alni*), Fusarium (e.g., F. laterium, *F. oxysporum, F. solani*), Gibellula, Gigaspora (e.g., G. margarita), Gliocladium (e.g., *G. virens* strains such as ATCC 52045 and GL-21), Glomus (e.g., *G. aggregatum, G. brasilianum*, G. clarnn,*G. deserticola, G. etunicatum, G. fasciculatum, G. intraradices* strains such as RTI-801, *G. monosporum, G. mosseae*), Gluconobacter, Halospirulina, Harposporium (e.g., H. anguillulae), Hesperomyces, Hirsutella (e.g., H. minnesotensis, H. rhossiliensis, H. *thomsonii* strains such as ATCC 24874), Hydrogenophage, Hymenoscyphous (e.g., H. ericae), Hymenostilbe, Hvpocrella, Isaria (e.g., L fumosorosea strains such as Apopka-97 (deposited as ATCC 20874)), Klebsiella (e.g., *K. pneumoniae. K. oxytoca*), Kluyvera, Laccaria (e.g., *L. bicolor*, L. laccata), Lactobacillus, Lagenidium, Lecanicillium (e.g., L. lecanii strains such as KVO1, L. *longisporum* strains such as KV42 and KV71), Leptolegnia, Lysobacter (e.g., *L. antibioticus* strains such as 13-1 and HS124, L. enzymogenes strains such as 3.1T8), Massospora, Meristacrum (e.g., M. asterospermum), Mesorhizobium (e.g., M. abyssinicae, M. albiziae, M. alhagi, M. amorphae, M. australicum, M. camelthorni, M. caraganae, M. *chacoense*, M. ciceri, M. gobiense, M. hawassense, M. *huakuii, M. loti*, M *mediterraneum, M. metallidurans*, M. muleiense, M. opportunistum, M. plurifarium, M. qingshengii, M. robiniae, M sangaii, M. *septentrionale*, M. shangrilense, M. shonense, M. silamurunense, M. tamadayense, M. tarimense, M. temperatum, M. thiogangeticum, M. *tianshanense*), Metarhizium (e.g., M. anisopliae (also referred to as M. *brunneum*, Metarrhizium anisopliae, and green muscadine) strains such as IMI 330189, FI-985, FI-1045, F52 (deposited as DSM 3884, DSM 3885, ATCC 90448, SD 170 and ARSEF 7711) and ICIPE 69), M. flavoviride strains such as ATCC 32969), *Methylobacterium* (e.g., *M. adhaesivum, M aerolatum, M. aminovorans, M. aquaticum, M. brachiatum, M. brachythecii, M. bullatum, M. cerastii, M. chloromethanicum, M. dankookense, M. dichloromethanicum, M. extorquens, M. fujisawaense, M. gnaphalii, M goesingense, M. gossipiicola, M. gregans, M. haplocladii, M. hispanicum, M. iners, M. isbiliense, M. jeotgali, M. komagatae, M. longum, M. lusitanum, M. marchantiae, M mesophilicum, M. nodulans, M. organophilum, M. oryzae, M. oxalidis, M. persicinum, M. phyllosphaerae, M. platani, M. podarium, M populi, M. radiotolerans, M. rhodesianum, M. rhodinum, M. salsuginis, M. soli, M. suomiense, M. tardum, M. tarhaniae, M. thiocyanatum, M. thurigiense, M. trifolii, M. variabile, M. zatmanii*), Metschnikowia (e.g., M. fructicola), *Microbacterium* (e.g., M. laevaniformans), Microdochium (e.g., M. dimerum), Microsphaeropsis (e.g., M. *ochracea* P130A), Microvirga (e.g., M. aerilata, M. aerophila, M. flocculans, M. guangxiensis, M. lotononidis, *M. lupini, M. subterranea, M. vignae*, M. zambiensis), Monacrosporium (e.g., M. cionopagum), *Mucor, Muscodor* (e.g., *M. albus* such NRRL 30547, QST 20799 and SA-13, M. roseus strains such as NRRL 30548), Mycoderma, Myiophagus, Myriangium, *Myrothecium* (e.g., M. verrucaria), Nectria, Nematoctonus (e.g., N. geogenius, N. leiosporus), Neozygites, Nomuraea (e.g., N. *rileyi* strains such as SA86101, GU87401, SR86151, CG128 and VA9101), Nostoc (e.g., *N. azollae, N. caeruleum, N. carneum, N. comminutum, N. commune, N. ellipsosporum, N. flagelliforme, N. linckia, N. longstafli, N. microscopicum, N. muscorum, N. paludosum, N. pruniforme, N. punctifrome, N. sphaericum, N. sphaeroides, N. spongiaeforme, N. verrucosum*), Ochrobactrum (e.g., O. anthropi, O. cicero, O. cytisi, O. daejeonense, O. gallinifaecis, O. grigonense, O. guangzhouense, O. haematophilum, O. intermedium, O. lupini, O. oryzae, O. pectoris, O. pituitosum, O. pseudointermedium, O. pseudogrignonense, O. rhizosphaerae, O. thiophenivorans, O. tritici), Oidiodendron, Paecilomyces (e.g., P. jumosoroseus strains such as FE991 and FE 9901, *P. lilacinus* strains such as 251, DSM 15200 and BCP2), Paenibacillus (e.g., *P. alvei* strains such as NAS6G6, *P. azotofixans, P. polymyxa* strains such as ABP166 (deposited as NRRL B-50211)), Pandora, *Pantoea* (e.g., *P. agglomerans* strains such as NRRL B-21856, P. vagans strains such as C9-1), Paraglomus (e.g., P. brazilianum), Paraisaria, Pasteuria, Pasteuria (e.g., P. nishizawae strains such as Pn1, *P. penetrans*, P. ramose, P. sp. strains such as ATCC PTA-9643 and ATCC SD-5832, P. thornea, P. usage), Penicillium (e.g., *P. albidum*, P. aurantiogriseum, *P. bilaiae* strains such as ATCC 18309, ATCC 20851, ATCC 22348, NRRL 50162, NRRL 50169, NRRL 50776, NRRL 50777, NRRL 50778, NRRL 50777, NRRL 50778, NRRL 50779, NRRL 50780, NRRL 50781, NRRL 50782, NRRL 50783, NRRL 50784, NRRL 50785, NRRL 50786, NRRL 50787, NRRL 50788, NRRL 67154, NRRL 67155, NRRL 67156, NRRL 67157, NRRL 67158, NRRL 67159 and RS7B-SD1, P. brevicompactum strains such as AgRF18, *P. canescens* strains such as ATCC 10419, P. chyrsogenum, *P. citreonigrum, P. citrinum, P. digitatum, P. expansum* strains such as ATCC 24692 and YT02, P. fellatanum strains such as ATCC 48694, P. frequentas, P. fuscum, P. fussiporus, P. gaestrivorus strains such as NRRL 50170, *P. glabrum* strains such as DAOM 239074 and CBS 229.28, *P. glaucum*, P. griseojulvum, P. implicatum, *P. janthinellum* strains such as ATCC 10455, P. lanosocoeruleum strains such as ATCC 48919, P. lilacinum, P. minioluteum, P. montanense, *P. nigricans, P. oxalicum, P. pinetorum, P. pinophilum, P. purpurogenum, P. radicum* strains such as ATCC 201836, FRR 4717, FRR 4719 and N93/47267, P. raistrickii strains such as ATCC 10490, *P. rugulosum, P. simplicissimum. P. solitum, P. variabile, P. velutinum, P. viridicatum*), Phingobacterium, *Phlebiopsis* (e.g., *P. gigantea*), Photorhabdus, Phyllobacterium (e.g., *P. bourgognense, P. brassicacearum, P. catacumbae*, P. endophyticum, P. ifriqiyense, P. leguminum, P. *loti*, P. nvrsinacearum, P. sophorae, P. *trifolii*), *Pichia* (e.g., *P. anomala* strains such as WRL-076), Pisolithus (e.g., P. tinctorius), Planktothricoides, Plectonema, Pleurodesmospora, Pochonia (e.g., P. chlarnydopora), Podonectria, Polycephalomyces, Prochlorocoous (e.g., *P. marinus*), Prochloron (e.g., P. didemni), Prochlorothrix, Pseudogibellula, *Pseudomonas* (e.g., *P. agarici*, P. antartica, P. *aurantiaca*, *P. aureofaciens*, *P. azotifigens*, *P. azotoformans*, *P. balearica*, *P. blatchfordae*, *P. brassicacearum*, *P. brenneri*, *P. cannabina*, *P. cedrina*, *P. cepacia*, *P. chlororaphis* strains such as MA 342, *P. congelans*, *P. corrugata*, *P. costantinii*, *P. denitrificans*, *P. entomophila*, *P. fluorescens* strains such as ATCC 27663, CL 145A and A506, P. fragii, *P. fuscovaginae*, *P. fulva*, *P. gessardii*, *P. jessenii* strains such as PS06, *P. kilonensis*, *P. koreensis*, *P. libanensis*, P. li/i, *P. lundensis*, *P. lutea*, *P. luteola*, *P. mandelii*, *P. marginalis*, P. meditranea, P. meridana, *P. migulae*, *P. moraviensis*, *P. mucidolens*, *P. orientalis*, *P. oryzihabitans*, *P. palleroniana*, *P. panacis*, *P. paralulva*, *P. peli*, *P. pertucinogena*, *P. plecoglossicida*, *P. protogens*, *P. proteolytica*, *P. putida*, P. pyrocina strains such as ATCC15958, *P. rhodesiae*, P. sp. strains such as DSM 13134, *P. striata*, *P. stutzeri*, *P. syringae*, *P. synxantha*, *P. taetrolens*, *P. thisvervalensis*, *P. tolaasii*, *P. veronii*), Pseudozyma (e.g., P. flocculosa strains such as PF-A22 UL), *Pythium* (e.g., *P. oligandrum* strains such as DV 74), *Rhizobium* (e.g., *R. aggregatum*, *R. alamii*, *R. alkalisoli*, *P. alvei*, *P. azibense*, *P. borbori*, *R. calliandrae*, *R. cauense*, *R. cellosilyticum*, R. daejeonense, R. endolithicum, R. endophyticum, R. etli, *R. fabae*, *R. flavum*, *R. fredii*, *R. freirei*, *R. galegae*, *R. gallicum*, *R. giardinii*, *R. grahamii*, *R. hainanense*, R. halophytocola, R. *halotolerans*, R. helanshanense, R. herbae, *R. huautlense*, *R. indigoferae*, R. jaguaris, R. kunmingense, R. laguerreae, *R. larrymoorei*, *R. leguminosarum* strains such as SO$_{12}$A-2 (IDAC 080305-01), R. lemnae, R. leucaenae, *R. loessense*, *R. lupini*, *R. lusitanum*, R. mayense, R. mesoamericanum, R. mesosinicum, R. miluonense, *R. mongolense*, R. multihospitium, R. *naphthalenivorans*, R. nepotum, *R. oryzae*, *R. pakistanensis*, R. paknamense, R. paranaense, R. *petrolearium*, *R. phaseoli*, R. phenanthrenilyticum, *R. pisi*, R. pongamiae, R. *populi*, R. pseudoryzae, R. pusense, R. qilianshanese, r. *radiobacter, R. rhizogenes*, R. rhizoryzae, R. rozettiformans, *R. rubi*, R. selenitireeducens, R. skierneiwicense, R. smilacinae, R. *soli*, R. sophorae, R. sophoriradicis, R. sphaerophysae, R. straminoryzae, R. subbaraonis, *R. sullae*, R. taibaishanense, R. tarimense, R. tibeticum, *R. trifolii* strains such as RP113-7, *R. tropici* strains such as SEMIA 4080, R. tubonense, *R. undicola*, *R. vallis*, *R. viciae* strains such as PINP3Cst, SU303 and WSM 1455, R. *vignae*, *R. vitis*, R. vanglingense, R. yantingense), *Rhizoctonia*, *Rhizopogon* (e.g., R. amylopogon, R. fulvigleba, R. *luteolus*, R. villosuli), *Rhodococcus*, Saccharopolyspora (e.g., *S. spinosa*), *Scleroderma* (e.g., *S. cepa S. citrinum*), Septobasidium, Serratia, Shinella (e.g., *S. kummerowiae*), Sinorhizoium (e.g., S. abri, *S. adhaerens*, *S. americanum, S. arboris, S. chiapanecum, S. fredii* strains such as CCBAU114 and USDA 205, S. garamanticus, S. indiaense, *S. kostiense, S. kummerowiae, S. medicae, S. meliloti* strains such as MSDJ0848, *S. mexicanus*, S. numidicus, S. psoraleae, S. saheli, S. sesbaniae, S. *sojae*, S. terangae, S. *xinjiangense*), Sorosporella, Sphaerodes (e.g., S. mycoparasitica strains such as IDAC 301008-01), *Spodoptera* (e.g., *S. littoralis*), Sporodiniella, Steinernema (e.g., S. carpocapsae, S. feltiae, S. kraussei strains such as L137), *Stenotrophomonas, Streptomyces* (e.g., S. NRRL B-30145, S. M1064, S. WYE 53 (deposited as ATCC 55750), *S. cacaoi* strains such as ATCC 19093, *S. galbus* strains such as NRRL 30232, *S. griseoviridis* strains such as K61, *S. lydicus* strains such as WYEC 108 (deposited as ATCC 55445), *S. violaceusniger* strains such as YCED-9 (deposited as ATCC 55660)), Streptosporangium, Stillbella, Swaminathania, *Talaromyces* (e.g., *T aculeatus, T flavus* strains such as V117b), Tetranacrium, *Thiobacillus*, Tilachlidium, Tolvpocladium, Tolypothrix, Torrubiella, Torulospora, Trenomyces, *Trichoderma* (e.g. T asperellum strains such as SKT-1, T. atroviride strains such as LC52 and CNCM 1-1237, T. fertile strains such as JM41 R, T. gamsii strains such as ICC 080, *T. hamatum* strains such as ATCC 52198, *T harzianum* strains such as ATCC 52445, KRL-AG2, T-22, TH-35, T-39 and ICC012, *T. polysporum*, T. reesi strains such as ATCC 28217 T. stromaticum, *T. virens* strains such as ATCC 58678, GL-3, GL-21 and G-41, T. viridae strains such as ATCC 52440, ICC080 and TV1), Typhula, Ulocladium (e.g., U. oudemansii strains such as HRU3), Uredinella, Variovorax, *Verticillium* (e.g., V. *chlamydosporum*, V. lecanii strains such as ATCC 46578), *Vibrio, Xanthobacter, Xanthomonas*. Xenorhabdus, *Yersinia* (e.g., Y entomophaga strains such as 082KB8), Zoophthora

The invention claimed is:

1. An agrochemical inoculant composition comprising a powder or granule that comprises:
   dried bacterial cells and/or spores; and
   one or more paraffin oils and/or one or more paraffin waxes,
   said one or more paraffin oils and/or one or more paraffin waxes comprising about 75 to about 95% of said agrochemical inoculant composition, by weight, based upon the total weight of said agrochemical inoculant composition,
   wherein at least 50% of said bacterial cells and/or spores remain viable when said agrochemical inoculant composition is stored at 20-25° C. and 35-65% relative humidity for a period of 12 weeks.

2. The agrochemical inoculant composition of claim 1, said bacterial cells and/or spores comprising about 5 to about 20% of said agrochemical inoculant composition, by weight, based upon the total weight of said agrochemical inoculant composition.

3. The agrochemical inoculant composition of claim 1, said bacterial cells and/or spores comprising about $1 \times 10^4$ to about $1 \times 10^{15}$ colony-forming units per gram and/or milliliter of said agrochemical inoculant composition.

4. The agrochemical inoculant composition of claim 1, further comprising one or more dispersants.

5. The agrochemical inoculant composition of claim 4, said one or more dispersants comprising about 0.1 to about 5% of said agrochemical inoculant composition, by weight, based upon the total weight of said agrochemical inoculant composition.

6. The agrochemical inoculant composition of claim 1, wherein at least 50% of said bacterial cells and/or spores remain viable when said agrochemical inoculant composition is coated on a seed and then stored at 20-25° C. and 35-65% relative humidity for a period of 12 weeks.

7. A method, comprising applying the agrochemical inoculant composition of claim 1 to a plant propagation material.

8. A method, corn rising introducing the agrochemical inoculant composition of claim 1 into a plant growth medium.

9. A method, comprising applying the agrochemical inoculant composition of claim 1 to a plant.

10. The agrochemical inoculant composition of claim 1, said dried bacterial cells and/or spores comprising
    spray-dried, freeze-dried and/or spray-freeze-dried bacterial cells and/or spores.

11. The agrochemical inoculant composition of claim 1, wherein said bacterial spores and/or cells comprise one or more Gram negative bacterial strains.

12. The agrochemical inoculant composition of claim 1, wherein said bacterial spores and/or cells comprise one or more strains of *Bradyrhizobium*.

13. The agrochemical inoculant composition of claim 1, wherein said bacterial spores and/or cells comprise one or more strains of *Yersinia*.

14. The agrochemical inoculant composition of claim 1, said agrochemical inoculant composition comprising more than 0.5% water, by weight, based upon the total weight of said agrochemical inoculant composition.

15. The method of claim 7, wherein said agrochemical inoculant composition is coated on a plant seed.

16. The method of claim 9, wherein said bacterial spores and/or cells comprise one or more Gram negative bacterial strains.

17. The method of claim 9, wherein said bacterial spores and/or cells comprise one or more strains of *Yersinia*.

18. An agrochemical inoculant composition comprising a powder or granule that comprises:
    dried bacterial cells and/or spores; and
    one or more paraffin oils and/or one or more paraffin waxes,
    said one or more paraffin oils and/or one or more paraffin waxes comprising about 75 to about 95% of said agrochemical inoculant composition, by weight, based upon the total weight of said agrochemical inoculant composition,
    said agrochemical inoculant composition comprising no more than 0.5% water by weight, based upon the total weight of said agrochemical inoculant composition,
    wherein at least 50% of said bacterial cells and/or spores remain viable when said agrochemical inoculant composition is stored at 20-25° C. and 35-65% relative humidity for a period of 12 weeks.

19. A coated plant seed, comprising a plant seed and a coating that covers at least a portion of an outer surface of said seed, said coating comprising an agrochemical inoculant composition that comprises one or more paraffin oils and/or one or more paraffin waxes and a powder or granule comprising dried bacterial cells and/or spores, said one or more paraffin waxes comprising about 75 to about 95% of said agrochemical inoculant composition, by weight, based upon the total weight of said agrochemical inoculant composition, wherein at least 50% of said bacterial cells and/or spores remain viable when said coated plant seed is stored at 20-25° C. and 35-65% relative humidity for a period of 12 weeks.

20. A kit, comprising the coated plant seed of claim 19 and a container housing said coated plant seed.

* * * * *